United States Patent [19]

Farbood et al.

[11] Patent Number: 5,166,366

[45] Date of Patent: Nov. 24, 1992

[54] OCTALACTONE-CONTAINING COMPOSITION, FERMENTATION PROCESS FOR PRODUCING SAME AND ORGANOLEPTIC USES THEREOF

[75] Inventors: Mohamad I. Farbood, Holmdel; Lynda B. McLean, Matawan; James A. Morris, Howell; Henry A. Bondarovich, Holmdel, all of N.J.

[73] Assignee: International Flavors & Fragrances Inc., New York, N.Y.

[21] Appl. No.: 797,055

[22] Filed: Jan. 23, 1992

Related U.S. Application Data

[62] Division of Ser. No. 719,154, Jun. 21, 1991, Pat. No. 5,112,803.

[51] Int. Cl.$^5$ ............................................. C07C 307/32
[52] U.S. Cl. .................................... 549/273; 549/295; 549/326; 549/450; 435/134; 435/146
[58] Field of Search .............. 549/326, 295, 273, 450; 435/134, 146

[56] References Cited

U.S. PATENT DOCUMENTS

| | | | |
|---|---|---|---|
| 3,786,069 | 1/1974 | Aviron-Violet et al. | 549/295 |
| 4,396,715 | 8/1983 | Labows, Jr. et al. | 435/126 |
| 4,420,622 | 12/1983 | van de Moesdijk et al. | 549/326 |
| 4,540,665 | 9/1985 | Hasegawa et al. | 435/146 |
| 4,542,097 | 9/1985 | Labows, Jr. et al. | 435/126 |
| 4,960,597 | 10/1990 | Farbood et al. | 426/3 |
| 5,032,513 | 7/1991 | Page et al. | 435/146 |

FOREIGN PATENT DOCUMENTS

| | | | |
|---|---|---|---|
| 269351 | 1/1988 | European Pat. Off. | 512/11 |
| 89/12104 | 12/1989 | PCT Int'l Appl. | 512/11 |

OTHER PUBLICATIONS

Kutney et al., Helvetica Chimica Acta., vol. 65, Fasc. 5 (1982), No. 127, pp. 1343–1350, "127.Studies Related to Biological Detoxification of Kraft Pulp Mill Effluent IV. The Biodegradation of 14–Chlorodehydroabietic Acid with *Mortierella isabellina*".

Watanabe and Sato, Agr. Biol. Chem., vol. 34, No. 3, pp. 464–472, 1970, "Conversion of Some Saturated Fatty Acids, Aldehydes and Alcohols into Gamma and Delta-Lactones".

Holland et al., Canadian Journal of Chemistry, vol. 65, 502, (1987), "Side Chain Hydroxylation of Aromatic Compounds by Fungi. 1.Products and Stereochemistry".

Arctander, "Perfume and Flavor Chemicals (Aroma Chemicals)", vol. II, 1969, Monographs 2395 and 2403.

Furia and Bellanca, "Fenaroli's Handbook of Flavor Ingredients", Second Edition, vol. 2, published by CRC Press, Second Edition, 1975, pp. 440 and 439.

Institute for Fermentation, Osaka, "List of Cultures", 1988, p. 219.

*Primary Examiner*—James H. Reamer
*Attorney, Agent, or Firm*—Arthur L. Liberman

[57] ABSTRACT

Described is a process for the preparation of compositions of matter containing octalactones defined according to the structure:

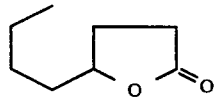

which includes the stereoisomers having the structures:

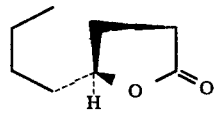

and

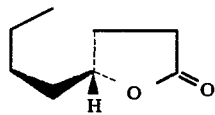

by means of the sequential steps of (i) fermentation of (Abstract continued on next page.)

caprylic acid or the ethyl ester of caprylic acid defined according to the generic structure:

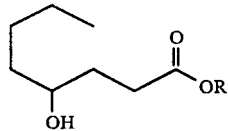

wherein R is hydrogen or ethyl using a microorganism selected from the group consisting of:
Mortierella isabellina, ATCC 44583;
Mortierella isabellina, ATCC 38063;
Syncephalastrum racemosum, NRRL A-5889;
Mortierella isabellina, IFO 7884;
Mortierella ramanniana var. angulispora, IFO 8187;
Mortierella isabellina, CBS 221.29; and
Mortierella isabellina, IFO 7873 whereby gamma hydroxy octanoic acid or ester thereof defined according to the structure:

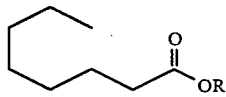

is formed; and (ii) lactonization of the resulting gamma hydroxy octanoic acid by means of simultaneous acidification and heating according to the reaction sequence:

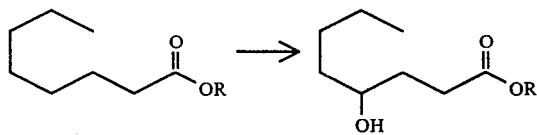

and

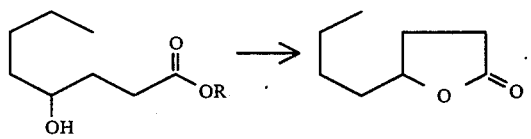

11 Claims, 28 Drawing Sheets

GLC PROFILE FOR EXAMPLE I(a).

GLC PROFILE FOR EXAMPLE I(b).

GLC PROFILE FOR EXAMPLE I(c).

GLC PROFILE FOR EXAMPLE I (d).

GLC PROFILE FOR EXAMPLE I(e).

GLC PROFILE FOR EXAMPLE I(f).

GLC PROFILE FOR EXAMPLE I(g).

GLC PROFILE FOR EXAMPLE III.

FIG. 12-a
MASS SPECTRUM FOR EXAMPLES II & III.

GLC PROFILE FOR EXAMPLE IV. FIRST & SECOND EXTRACTION.

GLC PROFILE FOR EXAMPLE IV.
THIRD EXTRACTION.

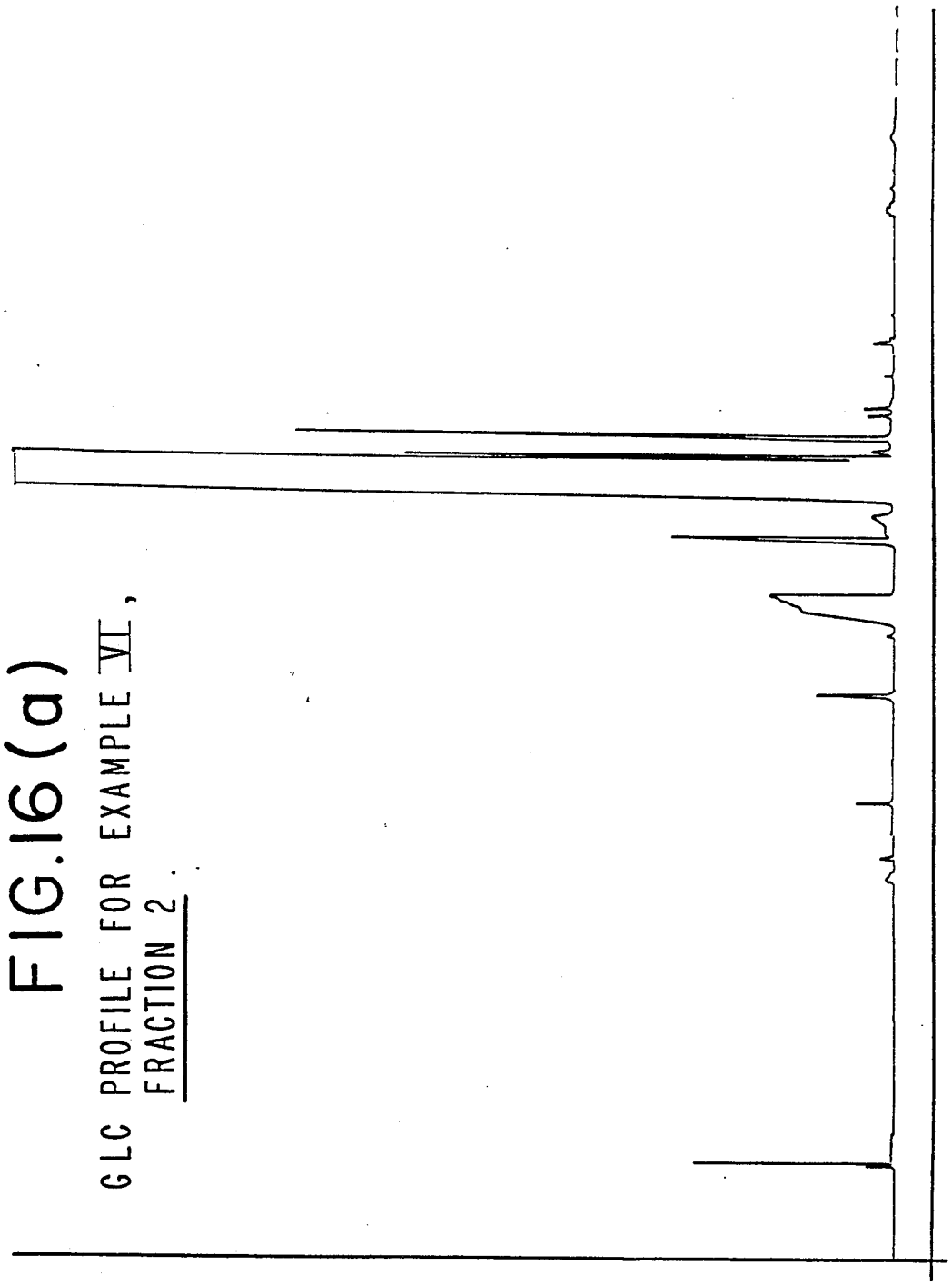

GLC PROFILE FOR EXAMPLE VI, FRACTION 2.

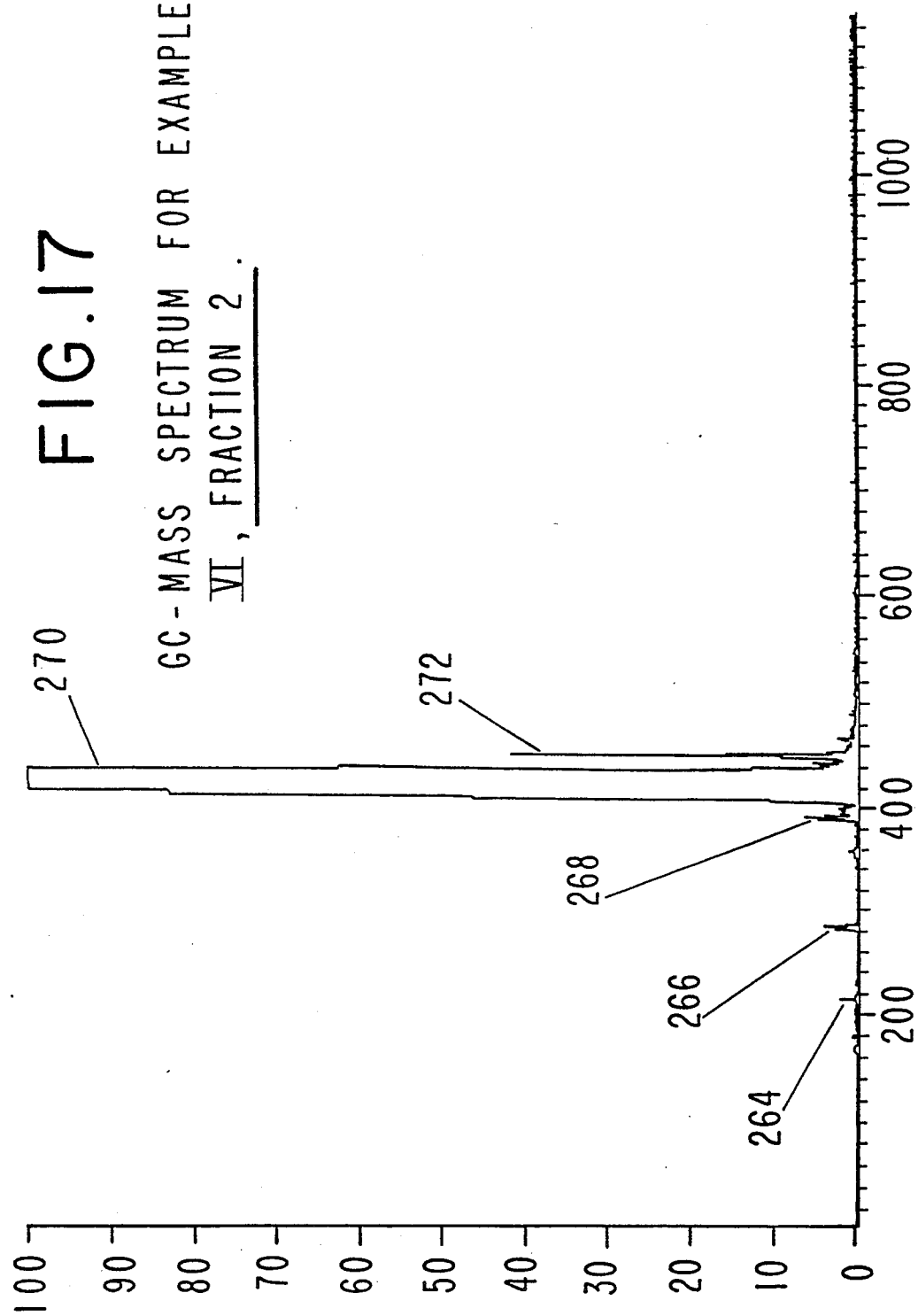

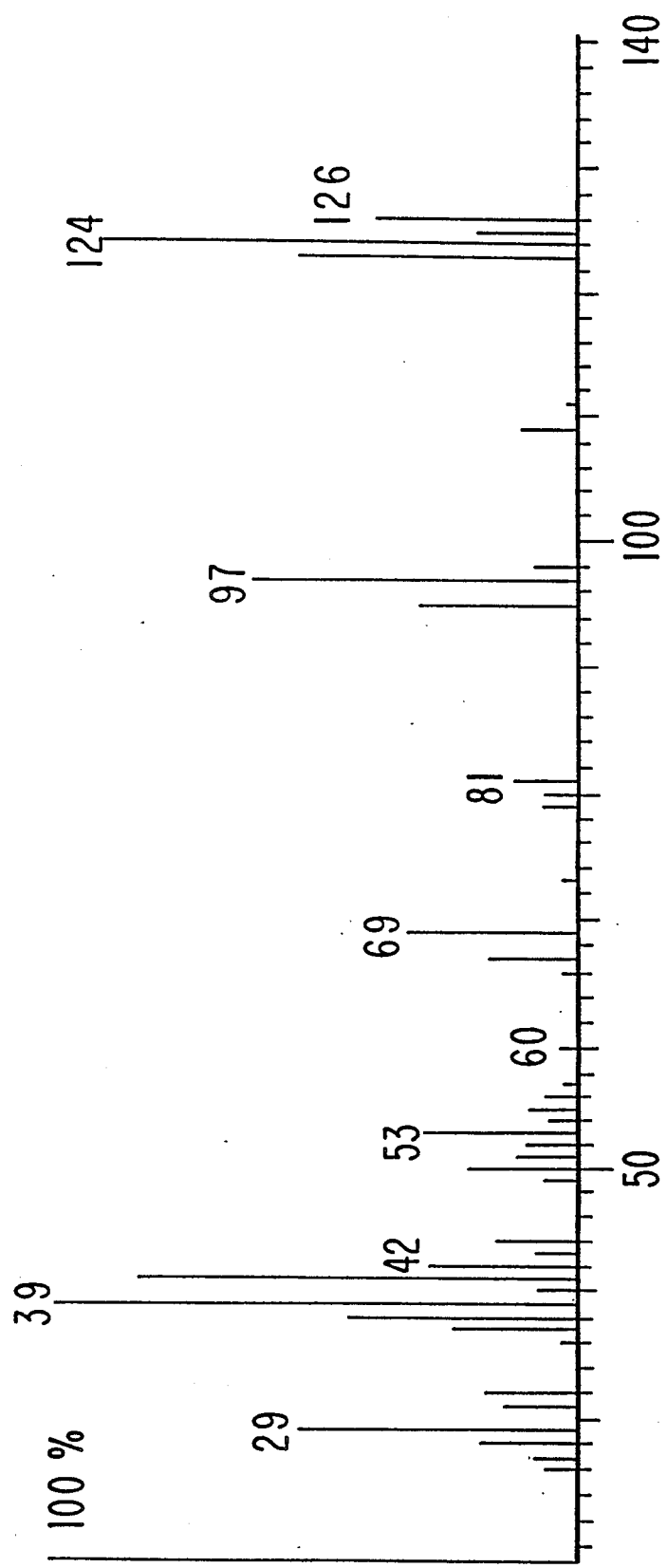
FIG. 18 MASS SPECTRUM FOR EXAMPLE VI, FRACTION 2.

GLC PROFILE FOR EXAMPLE VI, FRACTION 4.

GC-MASS SPECTRUM FOR EXAMPLE VI, FRACTION 4

GLC PROFILE FOR EXAMPLE VI, FRACTION 5.

GLC PROFILE FOR EXAMPLE VII (a).

GLC PROFILE FOR EXAMPLE VII (b).

GLC PROFILE FOR EXAMPLE VII (c).

OCTALACTONE-CONTAINING COMPOSITION, FERMENTATION PROCESS FOR PRODUCING SAME AND ORGANOLEPTIC USES THEREOF

This is a divisional of application Ser. No. 719,154, filed Jun. 21, 1991 now U.S. Pat. No. 5,112,803.

BACKGROUND OF THE INVENTION

This invention is concerned with a microbial process for the production of compositions of matter containing octalactone having the generic structure:

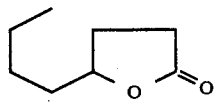

Considerable time and effort have been expended by microbiologists in the search for better processes for the production of saturated lactones; and more generally, lactones per se. U.S. Pat. No. 3,076,750 discloses a method for preparing certain optically active lactones and the corresponding hydroxycarboxylic acids by microbial reduction of ketocarboxylic acids. The metabolism of ricinoleic acid by some Candida strains was investigated by Okui, et al (J. Biochemistry, 54,536-540, 1963) who showed that gamma hydroxy decanoic acid was an intermediate in the oxidative degradation of ricinoleic acid. However, only trace amounts of gamma hydroxydecanoic acid were recovered from the fermentation medium due to the metabolysis of gamma hydroxydecanoic acid upon completion of the fermentation, and the toxicity of ricinoleic acid to the microorganism, which limits the amount of substrate that can be used.

U.S. Pat. No. 4,560,656 provided a method of producing optically active gamma hydroxydecanoic acid comprising culturing or incubating a microorganism capable of hydrolyzing castor oil, and effecting beta-oxidation of the resulting hydrolysate in the presence of castor oil, to produce gamma hydroxydecanoic acid.

U.S. Pat. No. 4,560,656 also provided a method of producing optically active gamma hydroxydecanoic acid comprising enzymatically hydrolyzing castor oil using lipase to form an enzymatic hydrolysate and culturing or incubating a microorganism capable of effecting beta-oxidation of the enzymatic hydrolysate in the presence of said hydrolysate to produce gamma hydroxydecanoic acid.

U.S. Pat. No. 4,560,656 also provided a method of producing optically active gamma hydroxydecanoic acid comprising culturing or incubating a microorganism capable of hydrolyzing castor oil and a microorganism capable of effecting beta-oxidation of castor oil hydrolysate in the presence of castor oil to produce gamma hydroxydecanoic acid.

European Published Patent Application 258993 published on Apr. 9, 1988 discloses a process for the production of optically active gamma hydroxydecanoic acid suitable for conversion to optically active gamma decalactone. The process covers steps of:

(a) culturing *sporobolomyces odorous*; and/or *rhodotorula glutinis* on a medium containing a ricinoleic acid sources at 15°-35° C. at a pH of 3-9 and, optionally;
(b) lactonizing the resulting gamma hydroxydecanoic acid to gamma decalactone.

Lion Corporation, European Published Patent Application No. 269,351 filed on Nov. 17, 1987 discloses a method for producing a fat containing gamma linolenic acid comprising the steps of culturing a microorganism belonging to the genus Absidia, the genus Mortierella, the genus Mucor, the genus Rhizopus or the genus Syncephalastrum with a fatty acid or an ester thereof as the carbon source, and converting the fatty acid or the ester thereof to gamma linolenic acid. The microorganisms exemplified are *Absidia corymbifera*, IFO 4010, *Mortierella isabellina*, IFO 7873, Rhizopus oryzae, IFO 5418 and *Syncephalastrum racemosum*, IFO 4816. Fatty acids or esters exemplified are set forth in paragraph 5, on page 3 of European Application 269,351, to wit, fatty acids having 8 to 22 carbon atoms, particularly 8 to 18 carbon atoms, as exemplified by n-capric acid, n-caprylic acid, lauric acid, myristic acid, palmitic acid, stearic acid, oleic acid and linoleic acid.

PCT Application 89/12104 (BASF Corporation) discloses a process for the preparation of gamma and delta lactones from organic carboxylic acids or derivatives thereof by means of cultivating, under aerobic conditions, a fungus of the genus Mucor in a suitable medium containing the carboxylic acid or a derivative thereof. Examples of the Mucor fungus are the following strains: *M. subtillissimus, M. mucedo, M. miehei, M. circinelloides, M. luteus, M. flavus, M. corticolus* and *M. albo-ater*. Furthermore, Example 2 of PCT Application No. 89/12104 indicates that when using *Mucor circinelloides* and using an ethyl octanoate substrate, the resulting product recovered is 49.4% gamma octalactone having the structure:

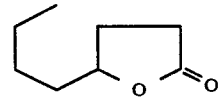

having a specific rotation (alpha$_d$ of $-39.8$).

Kutney, et al, Helvetica Chimica Acta., Volume 65, Pasc. 5 (1982) No. 127, at pages 1343-1350, discloses the use of *Mortierella isabellina* in carrying out a gamma hydroxylation of the compound having the structure:

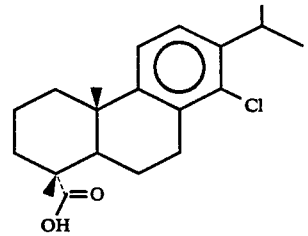

to form the compound having the structure:

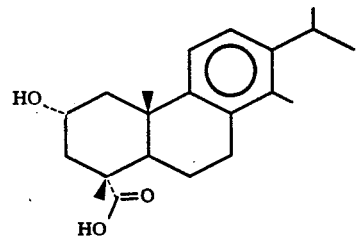

according to the reaction:

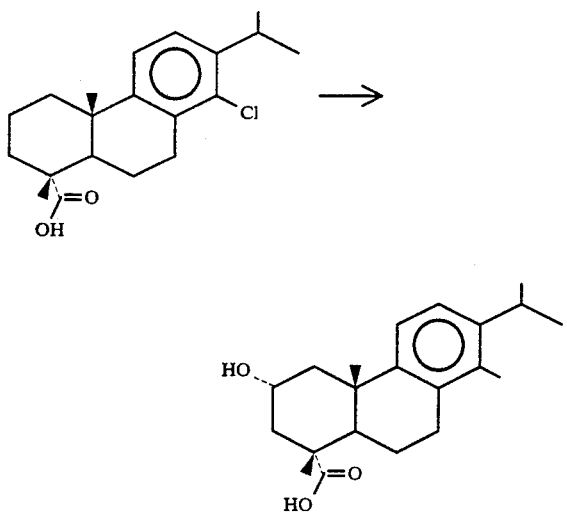

U.S. Pat. No. 4,960,597 issued on Oct. 2, 1990 described a process for the preparation of compositions of matter containing both saturated and unsaturated lactones including the saturated gamma decalactone. Thus, U.S. Pat. No. 4,960,597 described a process for the preparation of compositions of matter defined according to the generic structure:

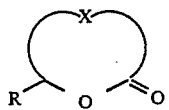

wherein R represents $C_6$ alkyl or alkenyl, and X represents $C_2$, $C_4$ or $C_6$ alkylene or alkylene; with the proviso that R is $C_6$ alkyl when X is alkenylene and R is $C_6$ alkenyl when X is alkenylene by means of the sequential steps of (i) fermentation of castor oil or ricinoleic acid using a microorganism selected from the group consisting of:

Candida petrophilum, ATCC 20226;
Candida oleophila, ATCC 20177;
Candida sp., ATCC 20504; and
Candida sake, ATCC 28137 whereby gamma hydroxydecanoic acid and a mixture of other acids defined according to the generic structure:

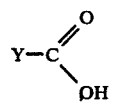

is formed wherein Y represents an oxo-saturated, oxo-unsaturated or di-unsaturated $C_9$, $C_{11}$ or $C_{13}$ moiety according to the reaction:

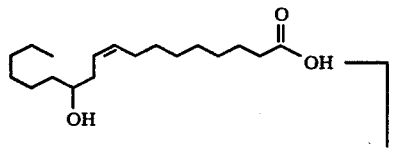

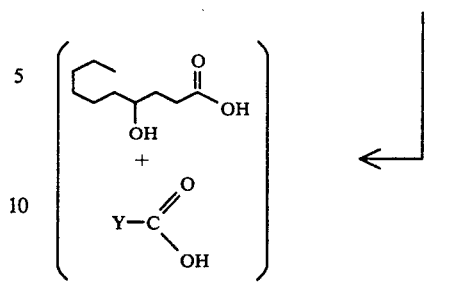

(ii) lactonization of the resulting gamma hydroxydecanoic acid by means of simultaneous acidification and heating according to the reaction:

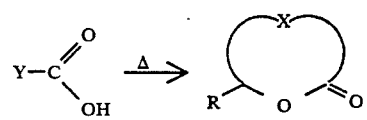

and (iii) lactonization (via distillation) of one or more of the resulting acids defined according to the structure:

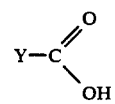

according to the reaction:

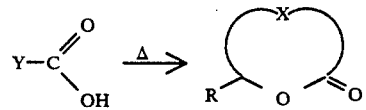

wherein the sum of the number of carbon atoms in the X moiety and in the R moiety is equal to the number of carbon atoms in the Y moiety minus 1.

In the flavor and fragrance art, a need has arisen for the development and efficient production of naturally occurring lactones which have heretofore been found to be useful and necessary in the creation of flavor formulations used in augmenting or enhancing the aroma or taste of foodstuffs, chewing gums, toothpastes, medicinal products, chewing tobaccos and smoking tobaccos and also useful in augmenting or enhancing the aroma of perfume compositions, colognes and perfumed articles (e.g., solid or liquid anionic, cationic, nonionic or zwitterionic detergents, perfumed polymers, fabric softener compositions, fabric softener articles, hair preparations, cosmetic powders and the like).

Gamma octalactone defined according to the structure:

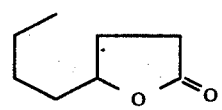

particularly its optical isomers having the structures:

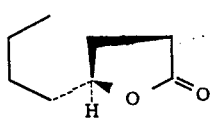

and

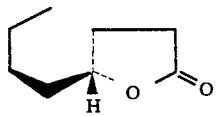

is useful particularly for forming butter flavors for use in flavoring products which cannot contain any natural butter due to health reasons. Thus, compounds having the structures:

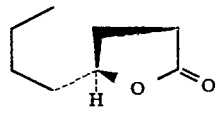

and

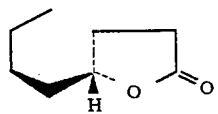

are found to be highly useful in producing butter flavored margarine. Furthermore, the combination of the compounds having the structures:

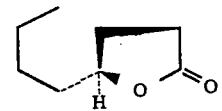

and

taken further together with other naturally occurring materials produced via fermentation including but not limited to, for example, the compounds having the structures:

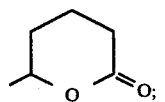 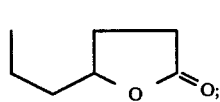

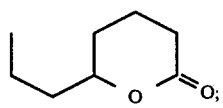 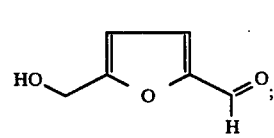

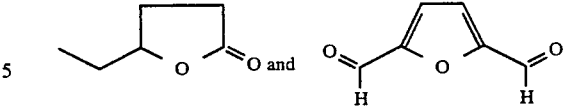

has been found to be highly useful in the production of butter flavors as well as in the production of perfumery materials, colognes and perfumed articles.

Nothing in the prior art however discloses the ability by means of fermentation to create novel mixtures of lactones together with other furan derivatives for use in augmenting or enhancing the organoleptic properties of consumable materials.

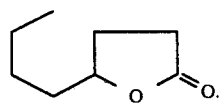

Figure 2:
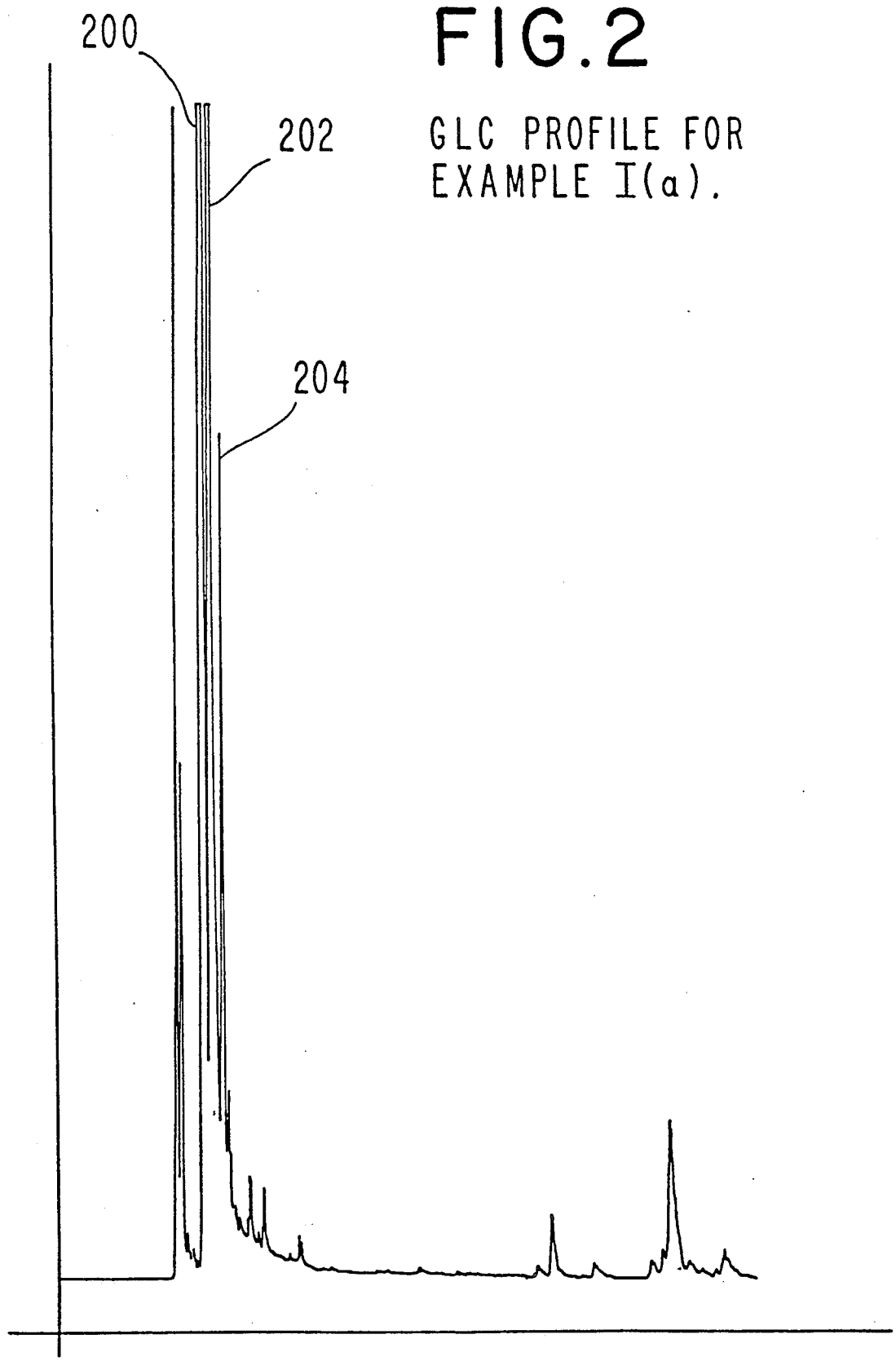

FIG. 2 is a GLC profile for the reaction product of Example I (a) containing the compound having the structure:

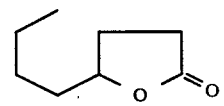

(Conditions: OV-1 column (50 meters×0.31 mm programmed from 75°–225° C. at 2.0° C. per minute).

Figure 3:
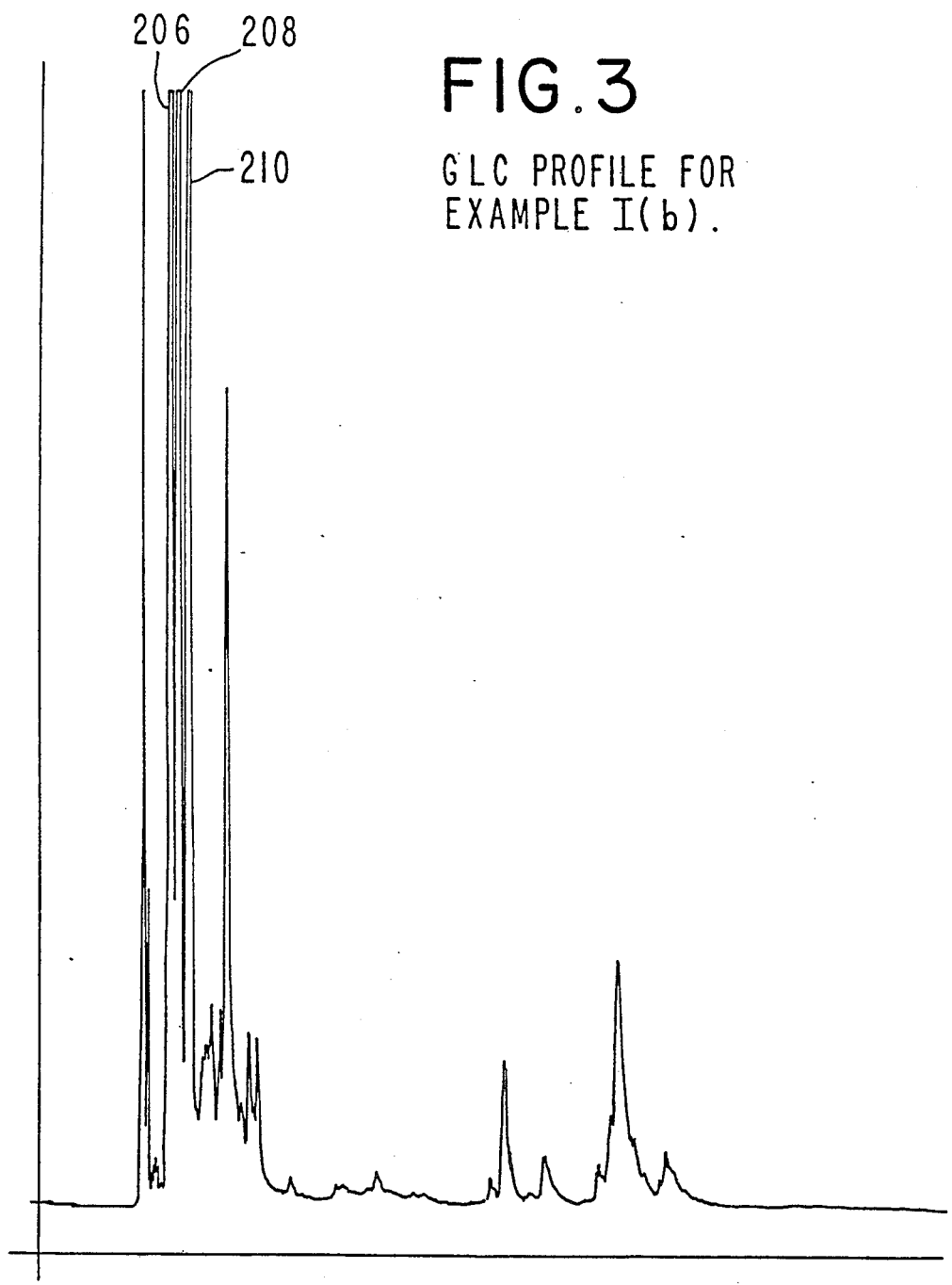

FIG. 3 is the GLC profile for the reaction product of Example I (b) containing the compound having the structure:

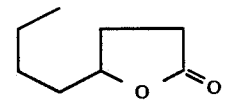

(Conditions: 50 m×0.31 mm OV-1 column programmed from 75°–225° C. at 2.0° C. per minute).

Figure 4:
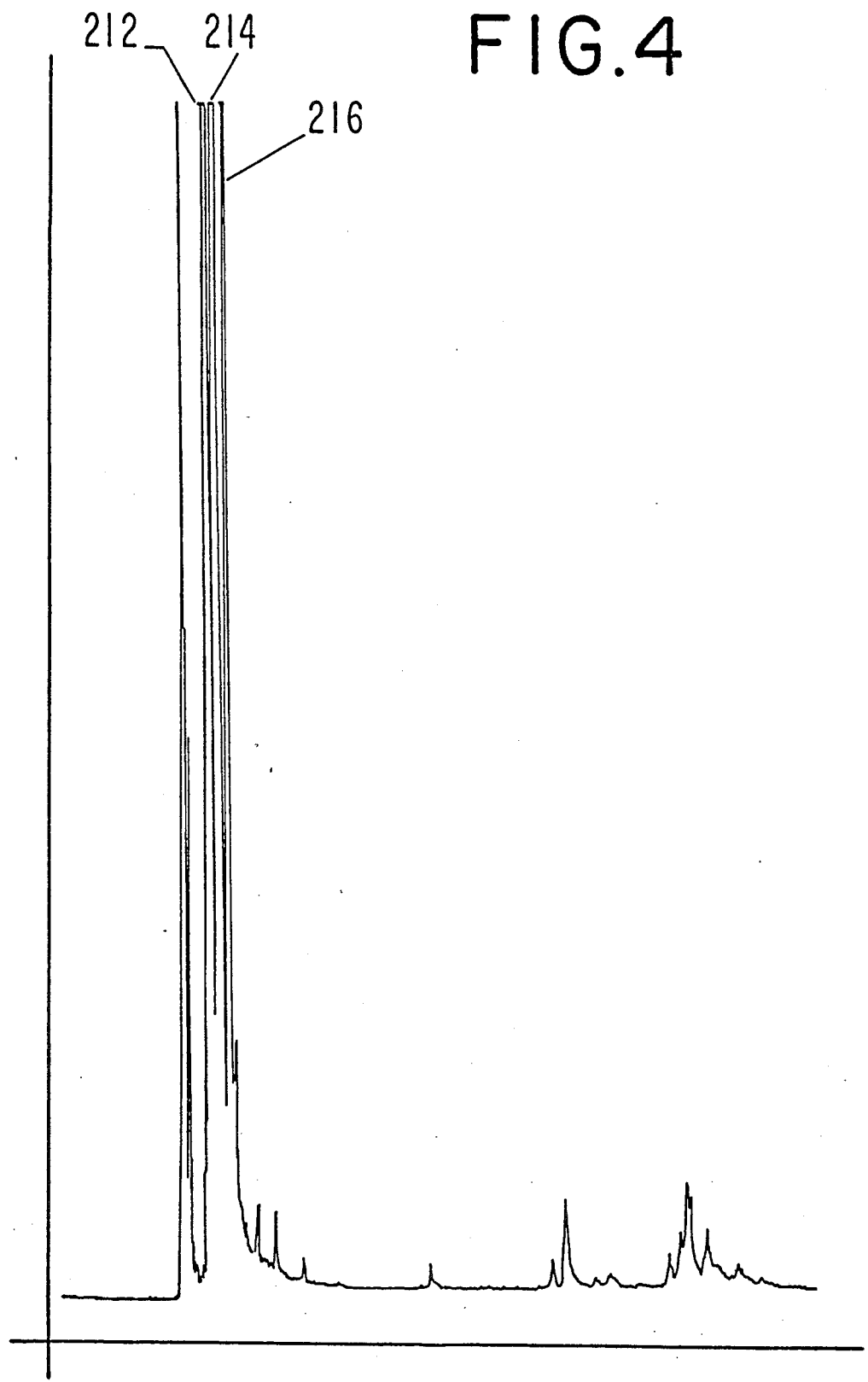

FIG. 4 is the GLC profile for the reaction product of Example I (c) containing the compound having the structure:

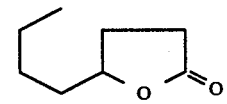

(Conditions: 50 m×0.31 mm OV-1 column programmed from 75°–225° C. at 2.0° C. per minute).

Figure 5:
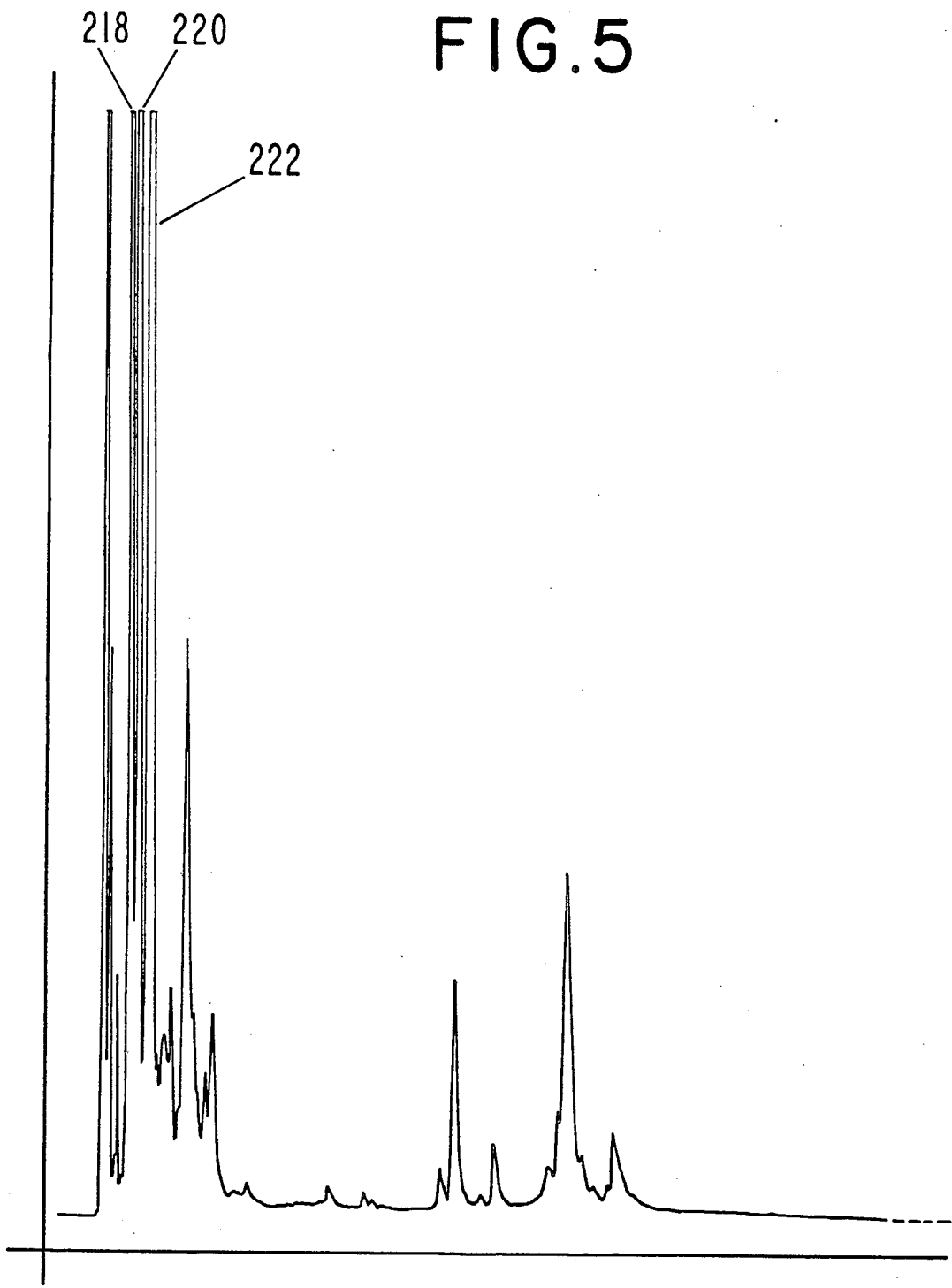

FIG. 5 is the GLC profile for the reaction product of Example I (d) containing the compound having the structure:

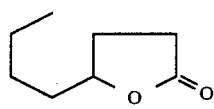

(Conditions: 50 m×0.31 mm OV-1 column programmed from 75°-225° C. at 2.0° C. per minute).

Figure 6:
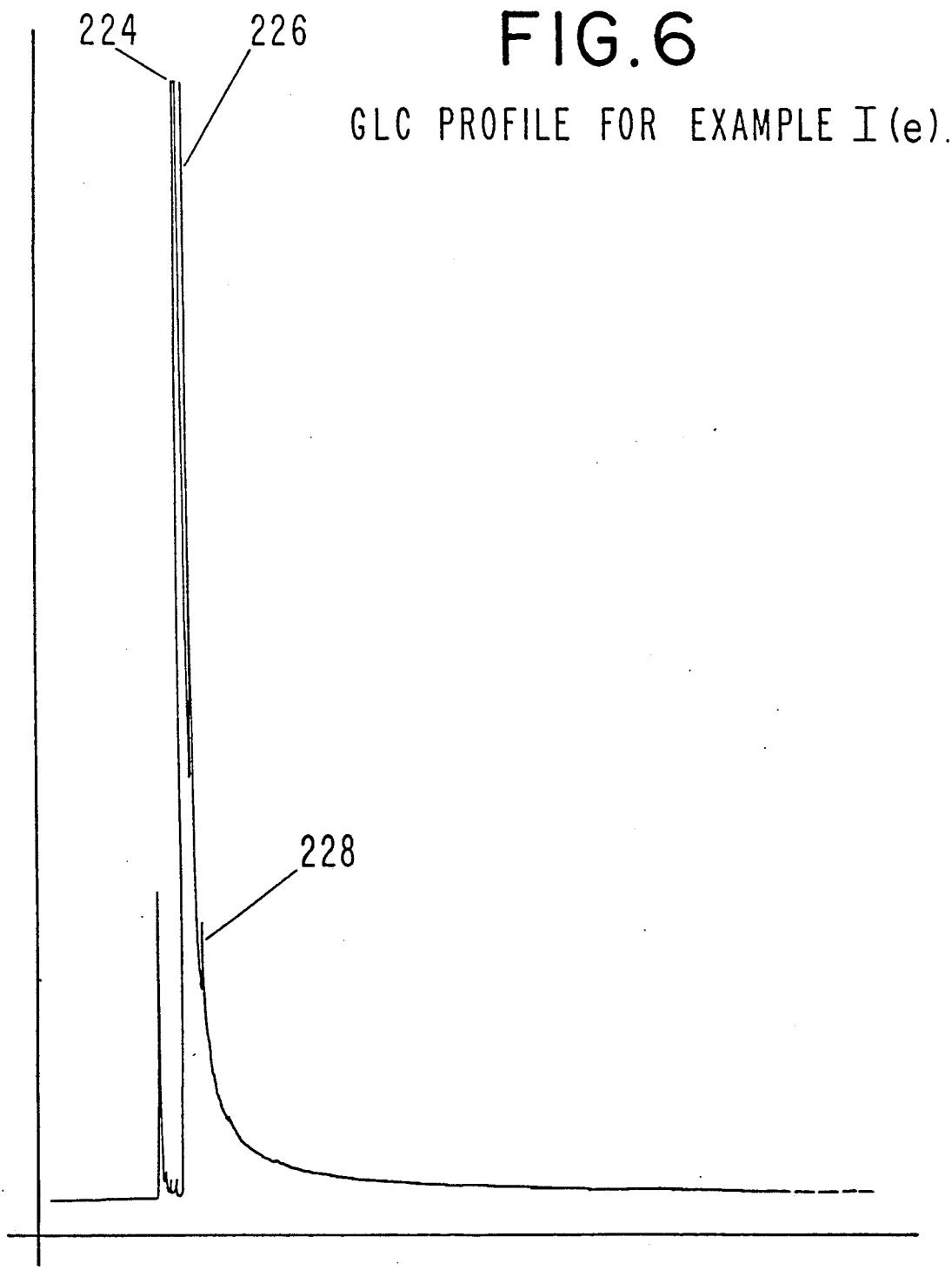

FIG. 6 is the GLC profile for the reaction product of Example I (e) containing the compound having the structure:

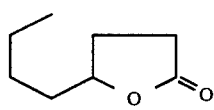

(Conditions: 50 m×0.31 mm OV-1 column programmed from 75°-225° C. at 2.0° C. per minute).

Figure 7:
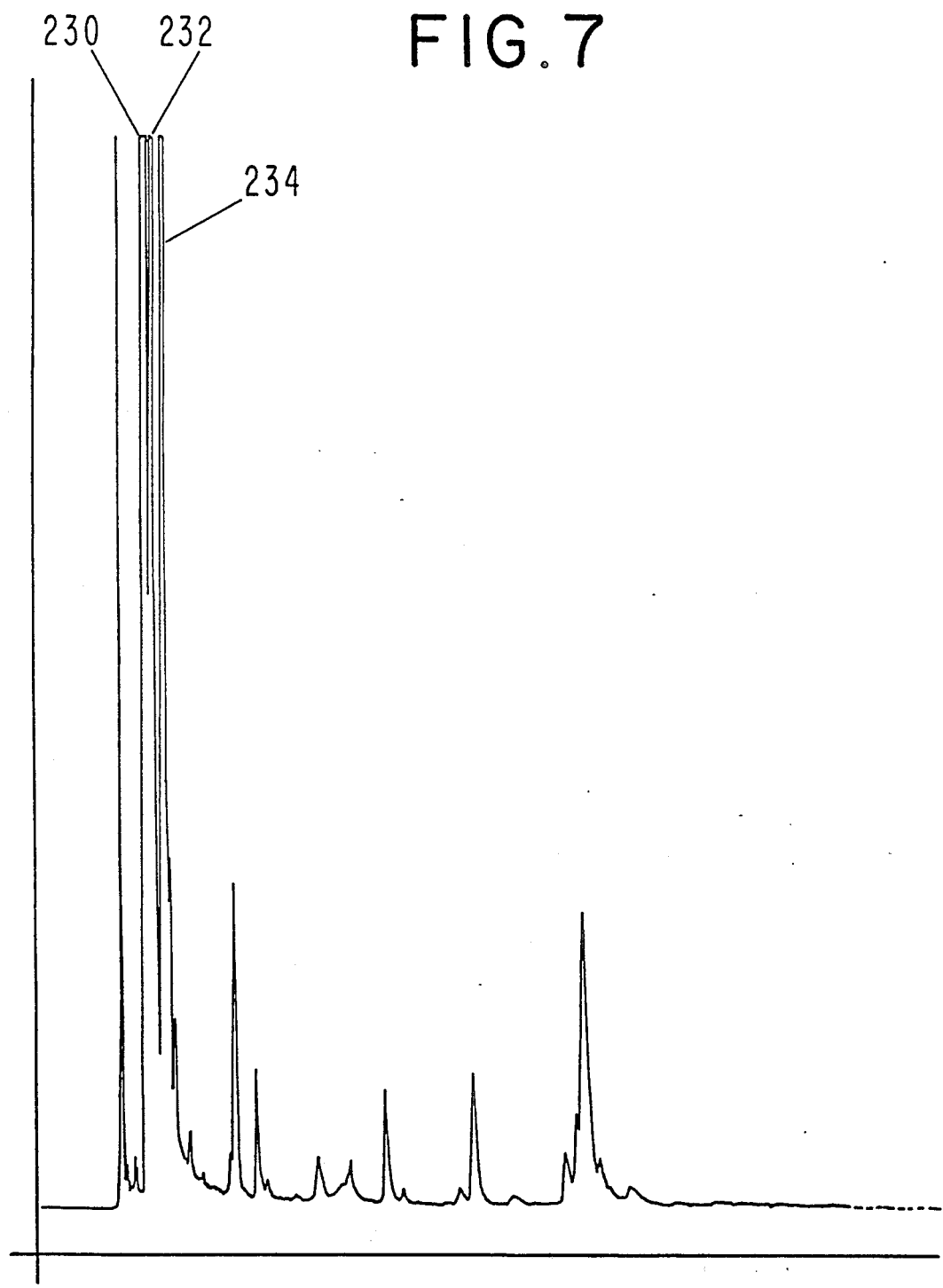

FIG. 7 is the GLC profile for the reaction product of Example I (f) containing the compound having the structure:

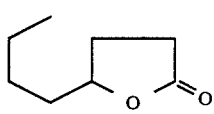

(Conditions: 50 m×0.31 mm OV-1 column programmed from 75°-225° C. at 2.0° C. per minute).

Figure 8:
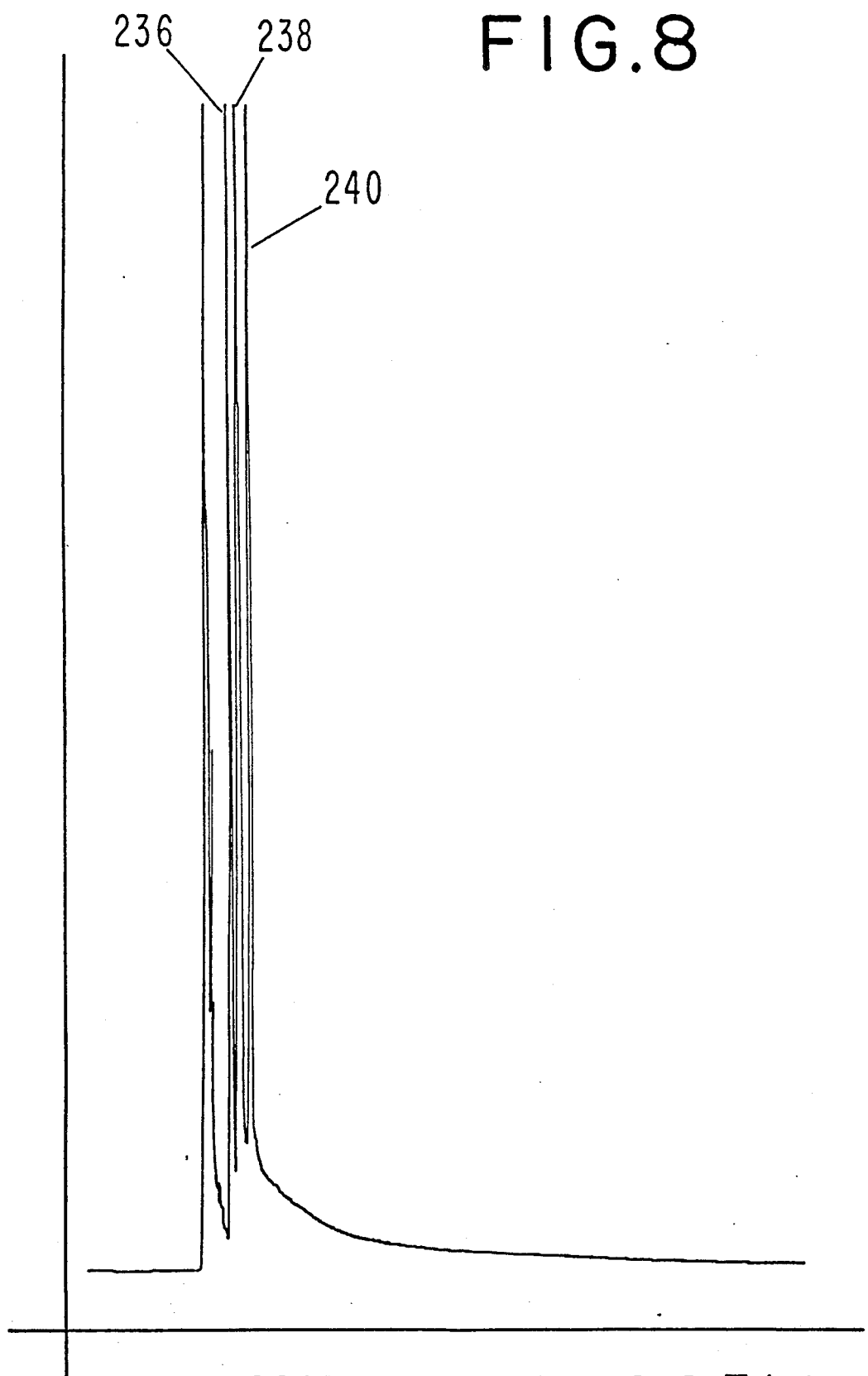

FIG. 8 is the GLC profile for the reaction product of Example I (g) containing the compound having the structure:

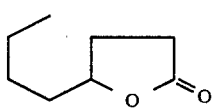

(Conditions: 50 m×0.31 mm OV-1 column programmed from 75°-225° C. at 2.0° C. per minute).

Figure 9:
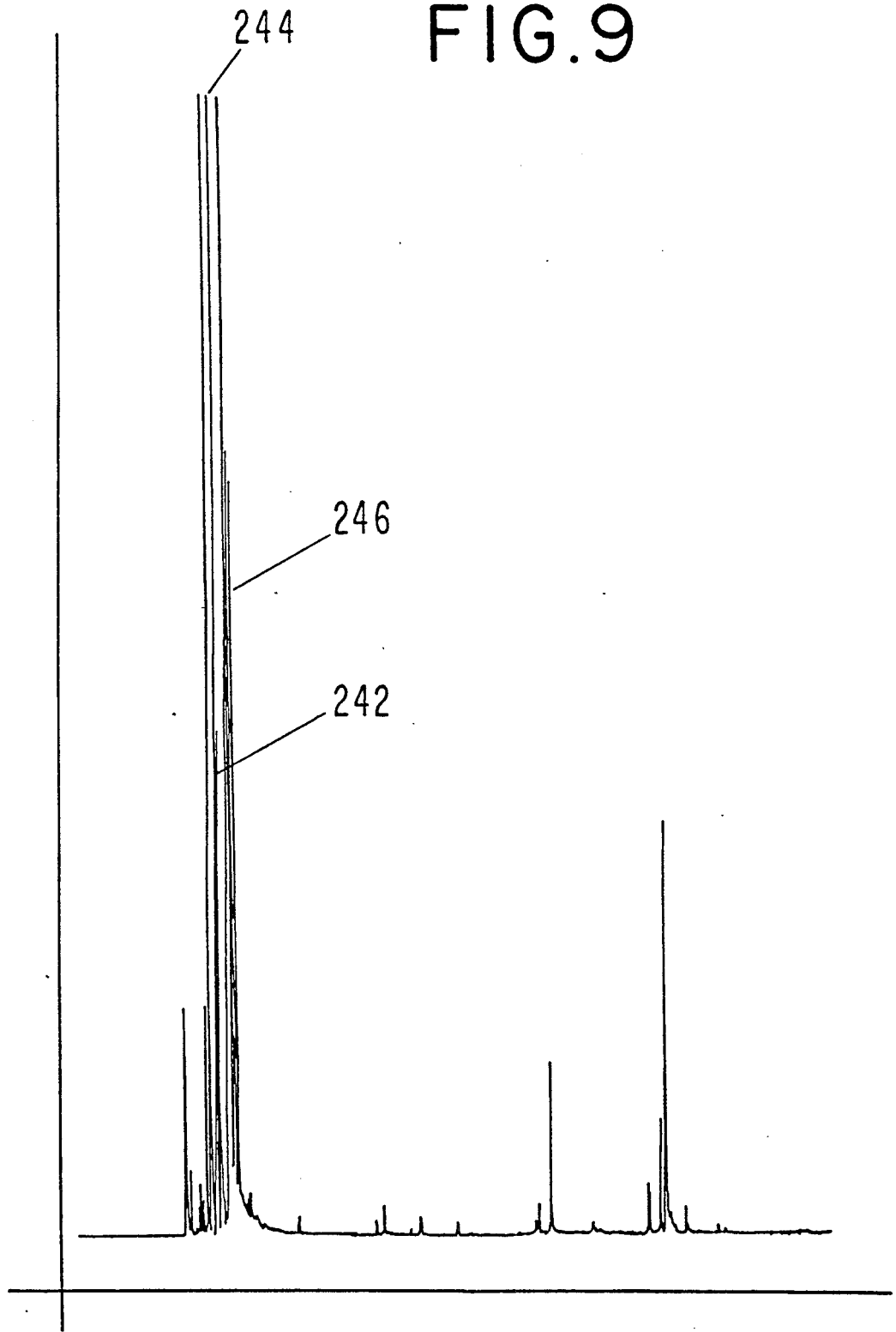

FIG. 9 is the GLC profile for the reaction product of Example III containing the compound having the structure:

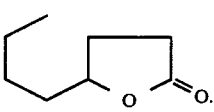

Figure 10:
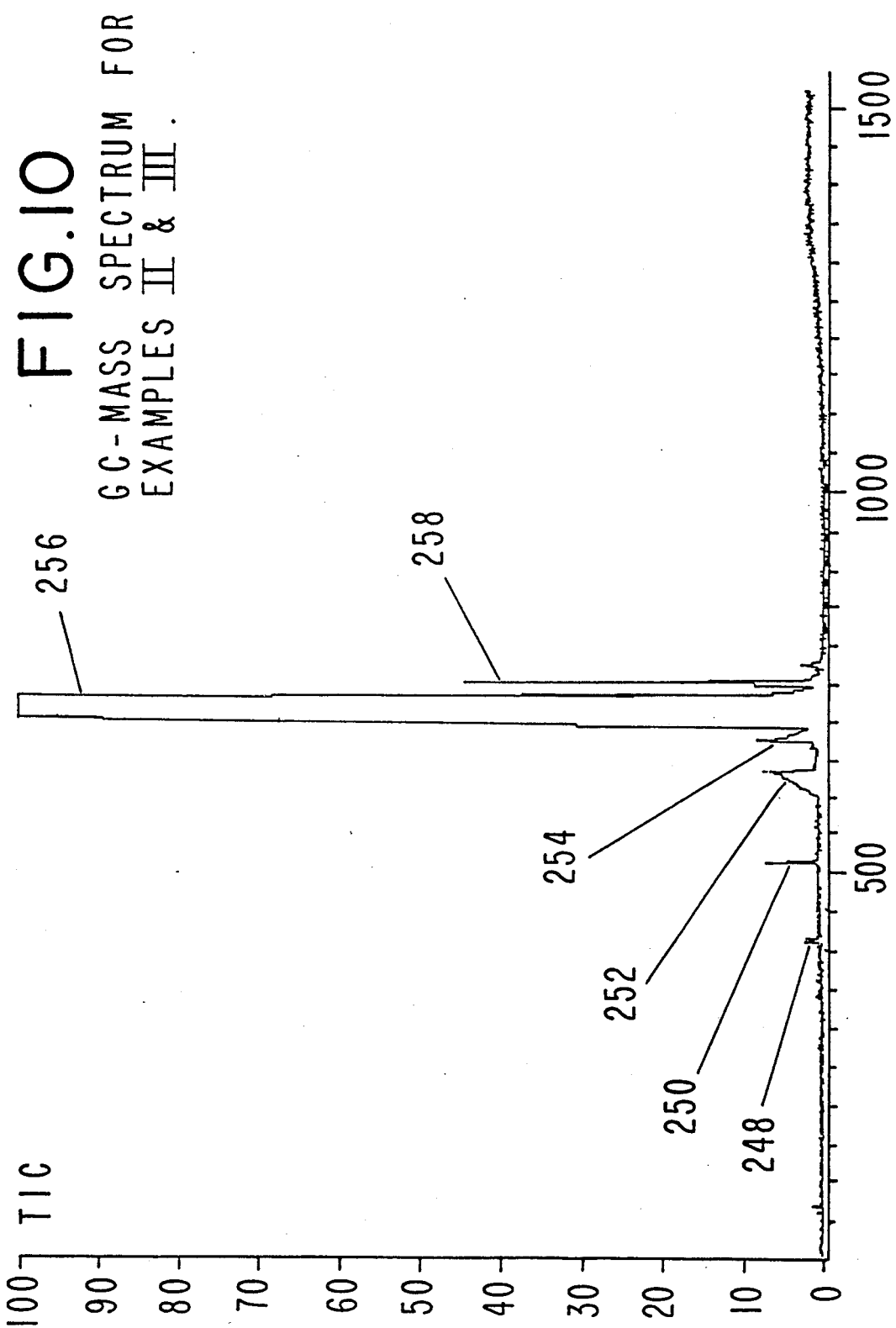

FIG. 10 is the GC mass spectrum for the combined product of Examples II and III containing the compound having the structure:

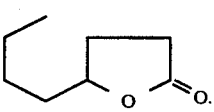

Figure 11:
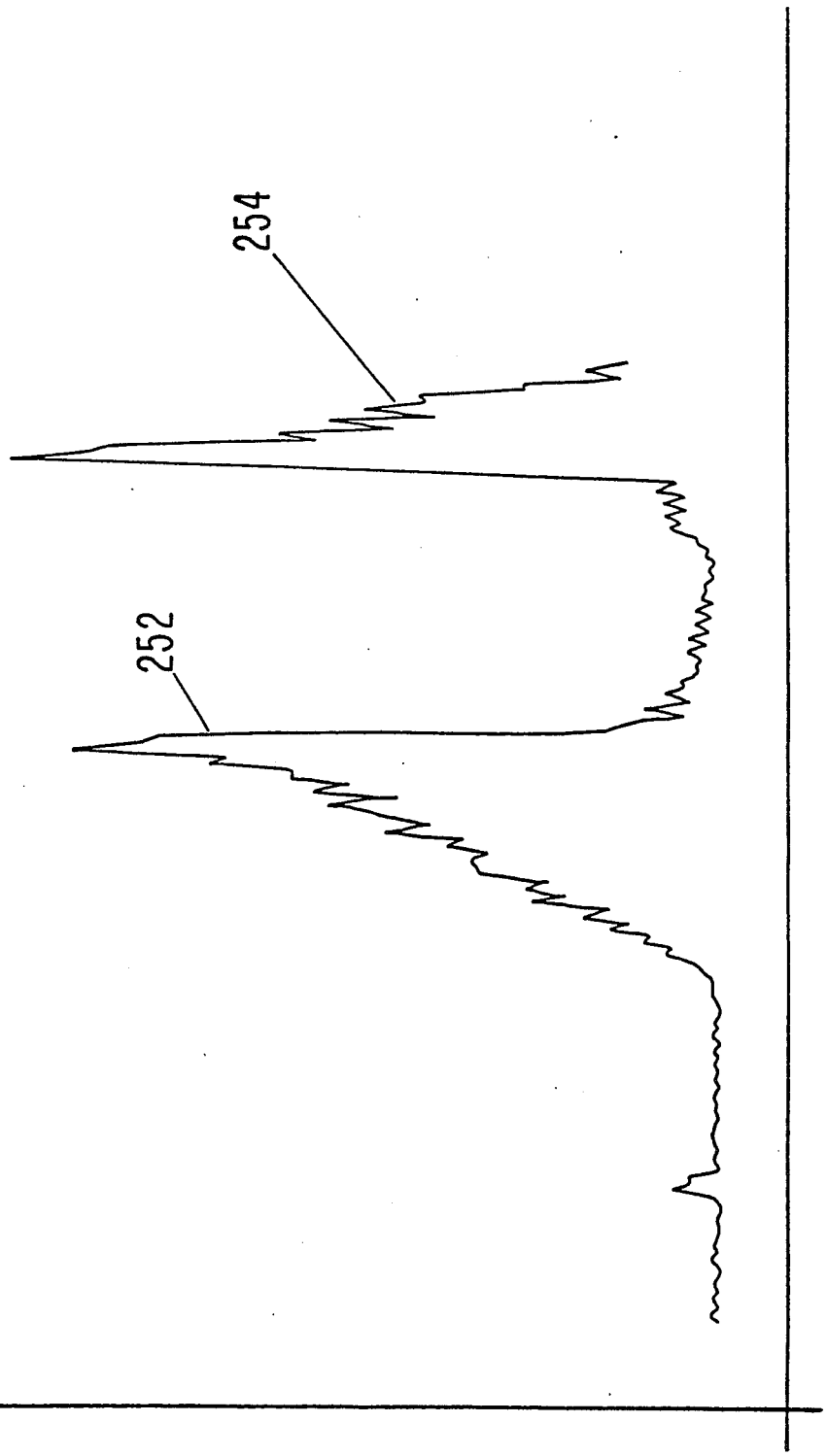

FIG. 11 shows in detail the peaks indicated by reference numerals 252 and 254 of the GC mass spectrum of FIG. 10.

Figure 12:
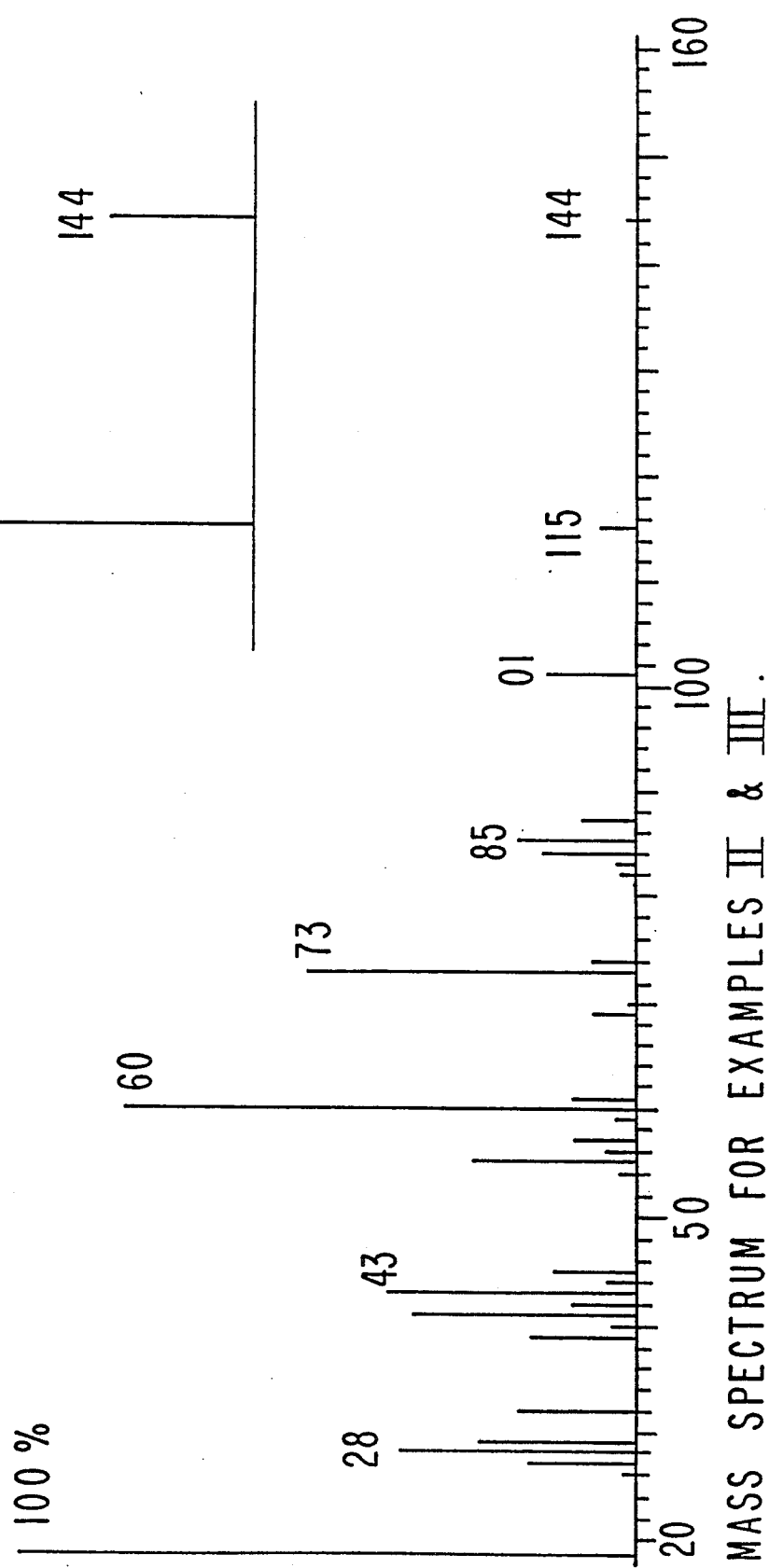

FIG. 12 is a mass spectrum for the combined product of Examples II and III.

FIG. 12a is a detailed section of the mass spectrum of FIG. 12.

Figure 13:
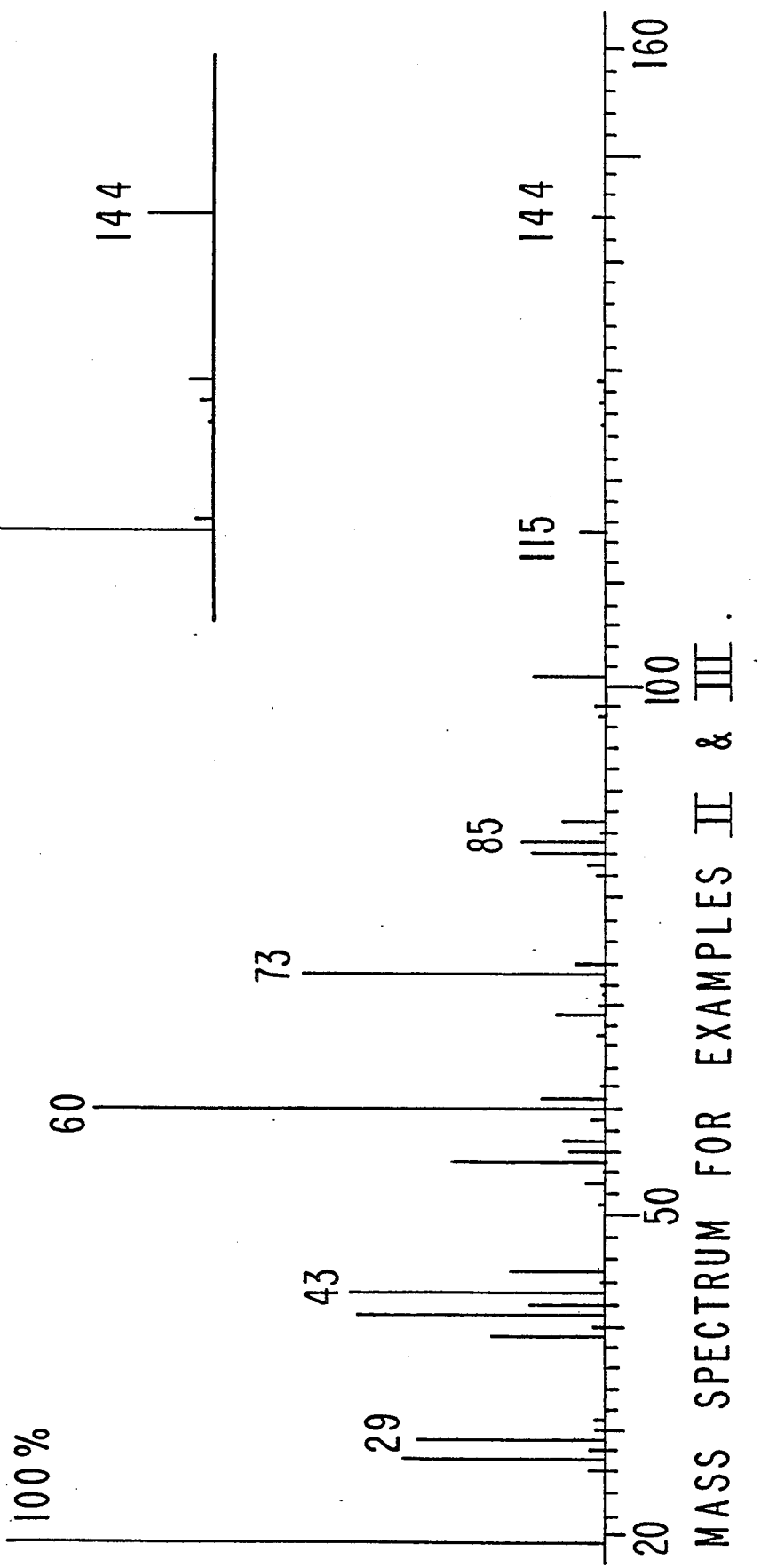

FIG. 13 is a mass spectrum of the combined product of Examples II and III.

FIG. 13a is a detailed section of the mass spectrum of FIG. 13.

Figure 14:
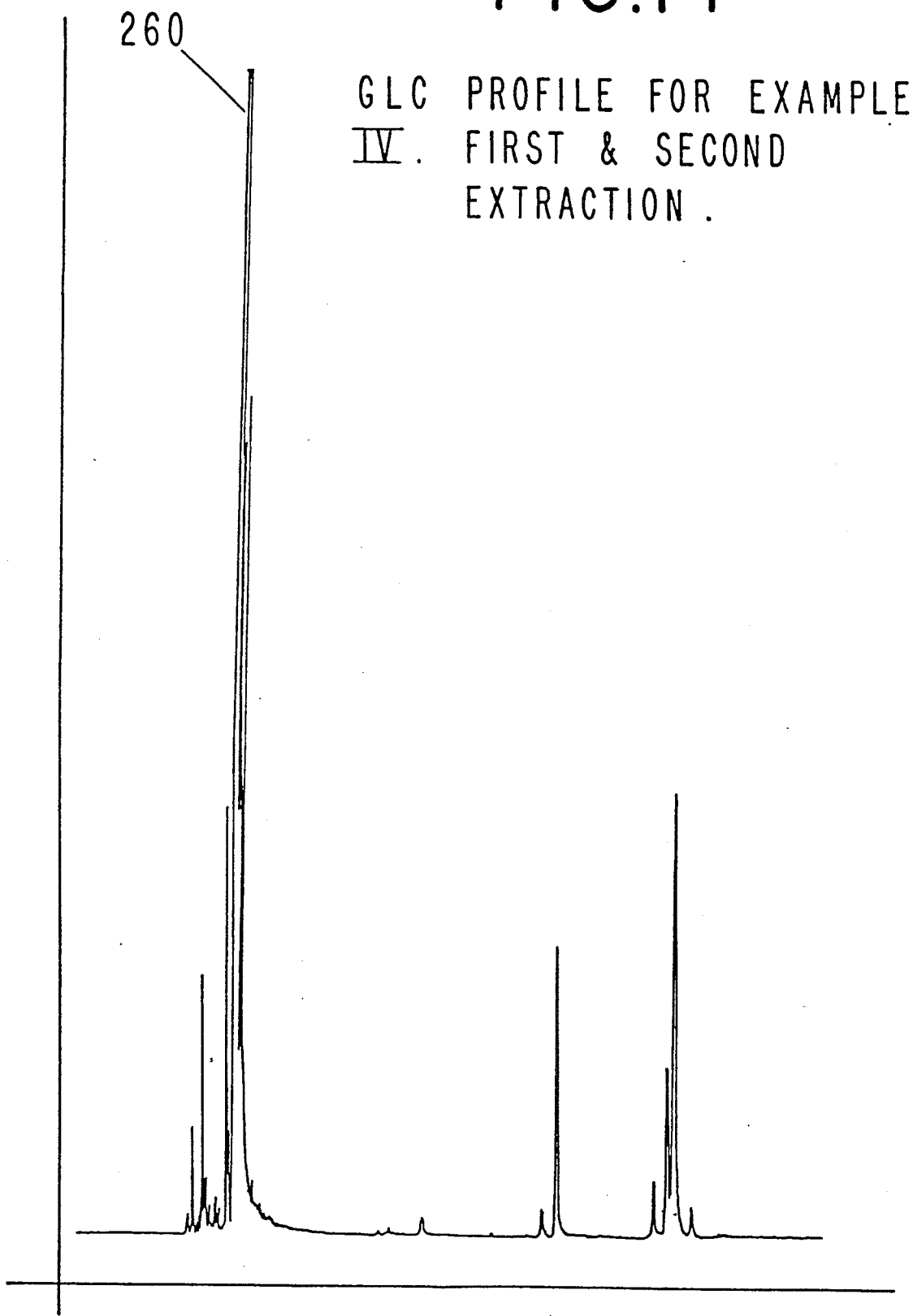

FIG. 14 is the GLC profile for the first and second extraction of the reaction product of Example IV containing the compound having the structure:

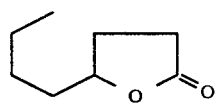

(Conditions: 50 m×0.31 mm OV-1 column programmed from 75°-225° C. at 2.0° C. per minute).

Figure 15:
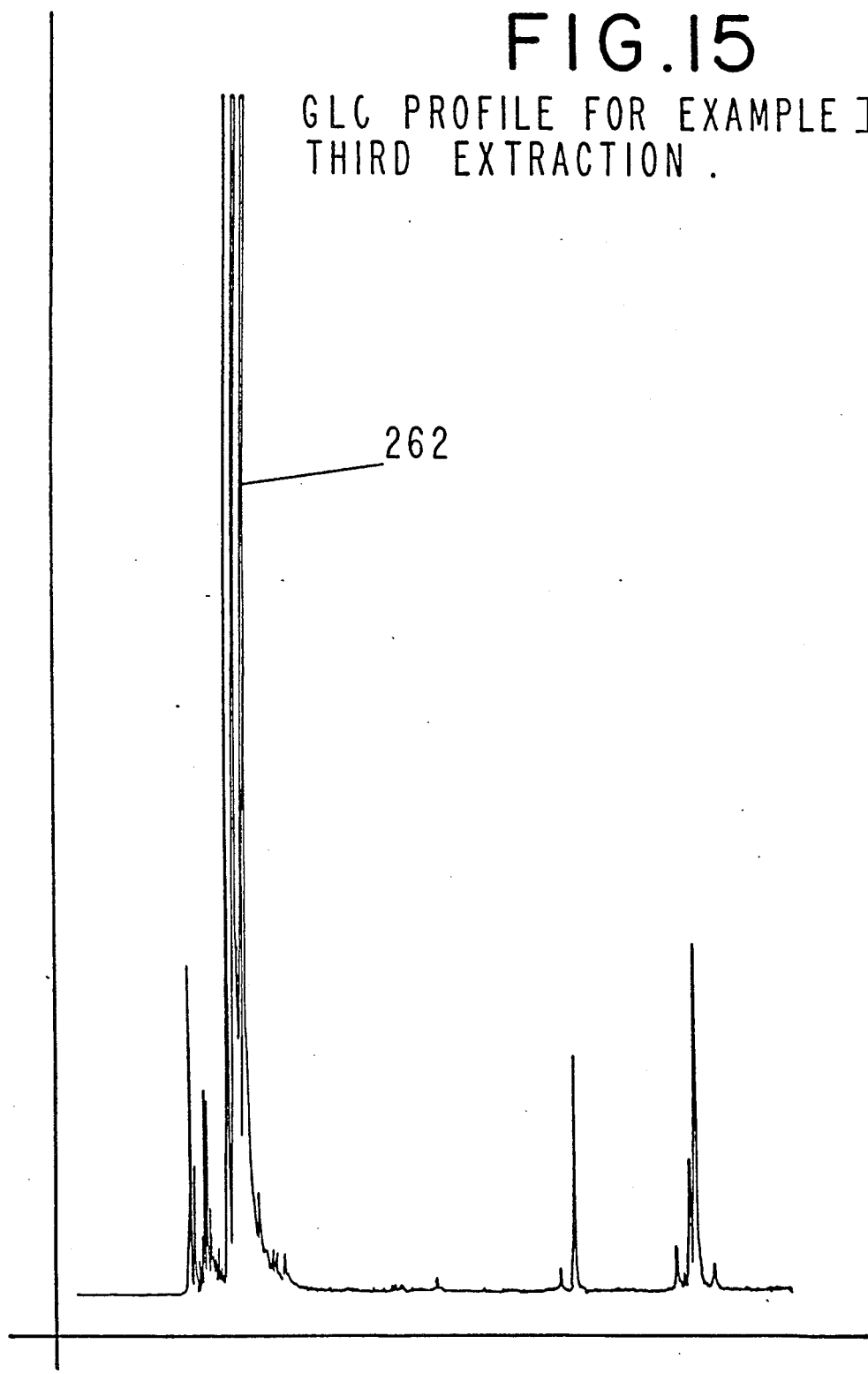

FIG. 15 is the GLC profile for the third extraction of the reaction product of Example IV containing the compound having the structure:

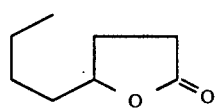

(Conditions: 50 m×0.31 mm OV-1 column programmed at 200° C. isothermal; and from 200°-250° C. at 10° C. per minute after a ten minute period).

FIG. 16(a) is the GLC profile for distillation Fraction 2 of the reaction product of Example VI.

Figure 16B:
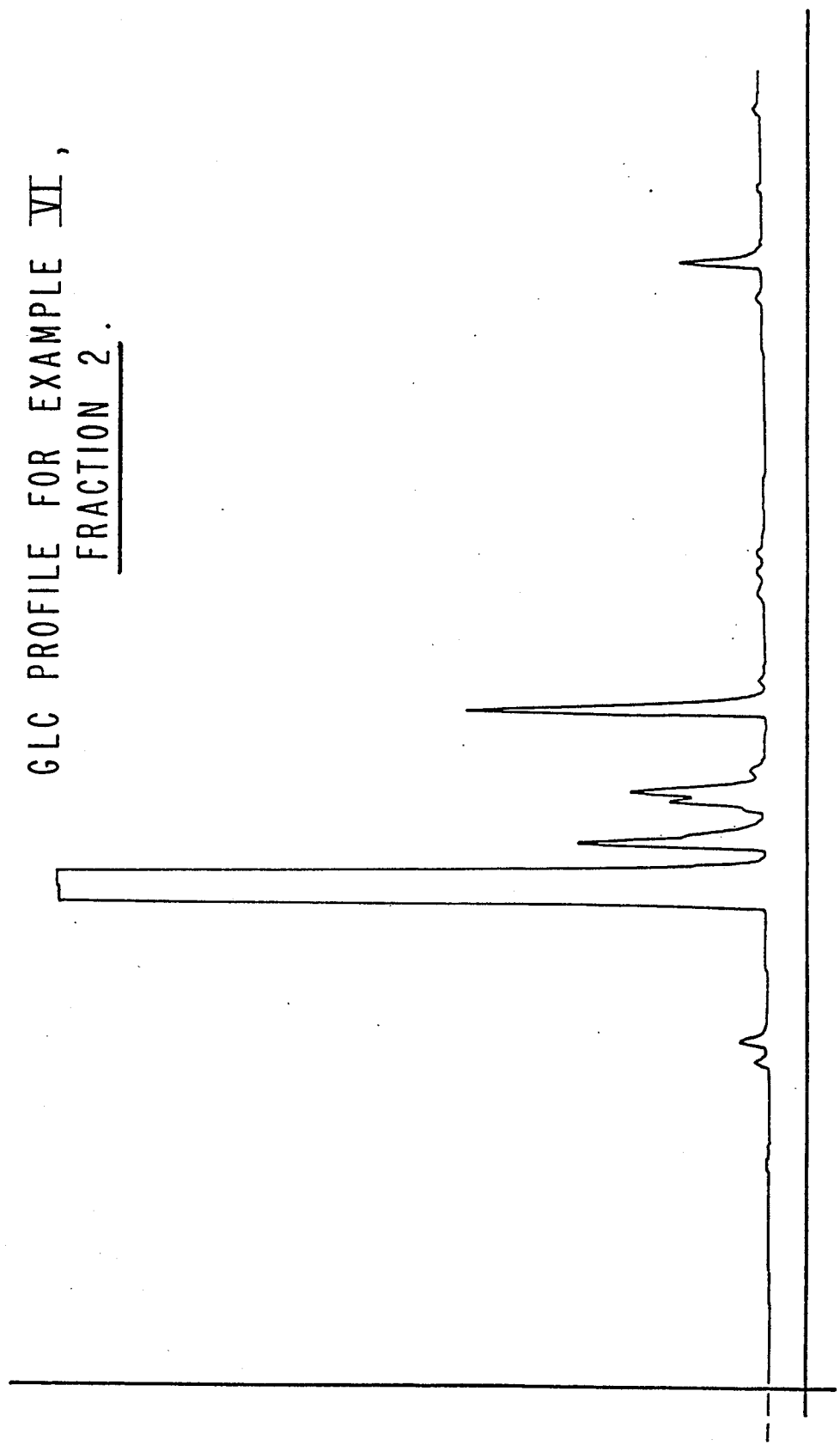

FIG. 16(b) is another GLC profile for distillation Fraction 2 of the reaction product of Example VI.

FIG. 17 is the GC mass spectrum for distillation Fraction 2 of Example VI containing the compound having the structure:

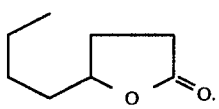

FIG. 18 is the mass spectrum for distillation Fraction 2 of Example VI.

Figure 19:
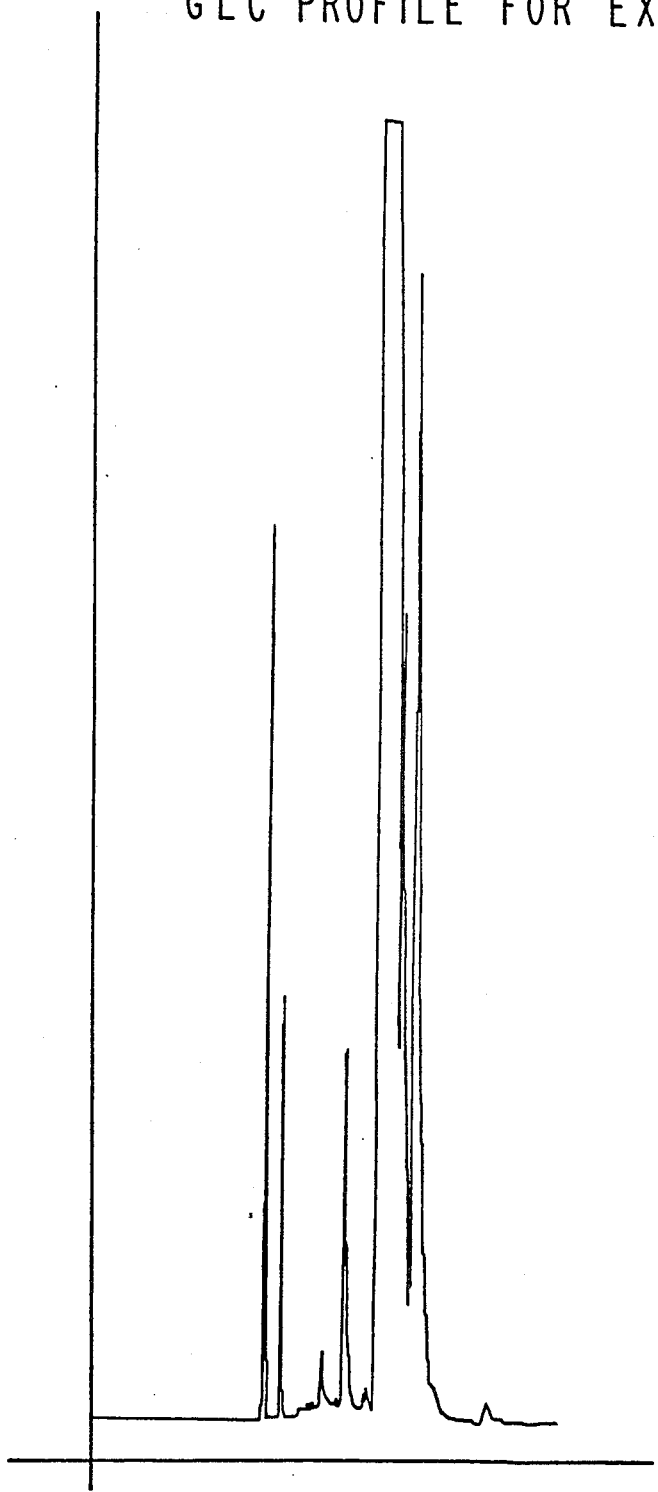

FIG. 19 is the GLC profile for distillation Fraction 4 of the reaction product of Example VI.

Figure 20:
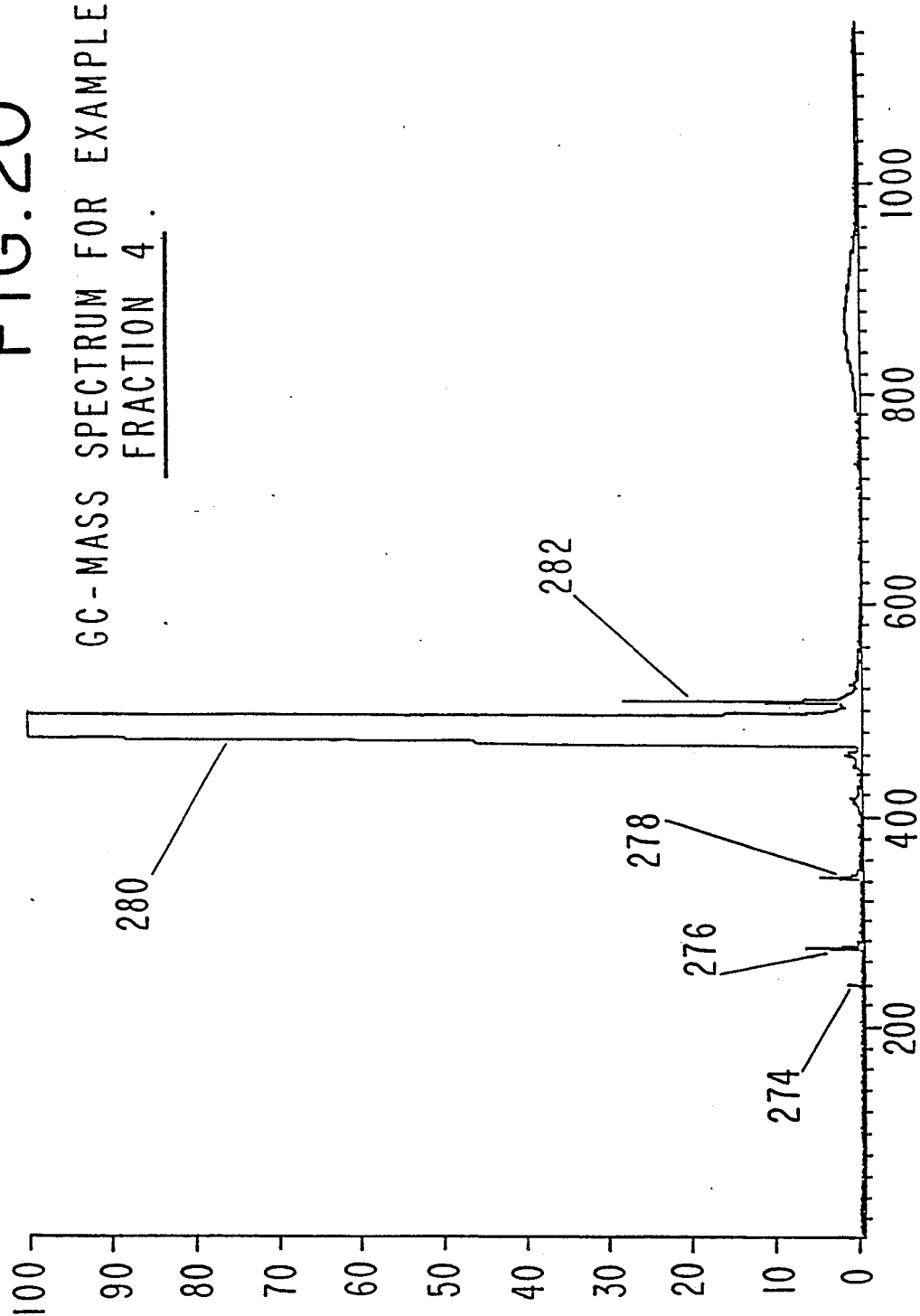

FIG. 20 is the GC mass spectrum of distillation Fraction 4 of the reaction product of Example VI containing the compound having the structure:

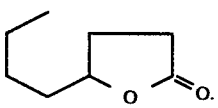

Figure 21:
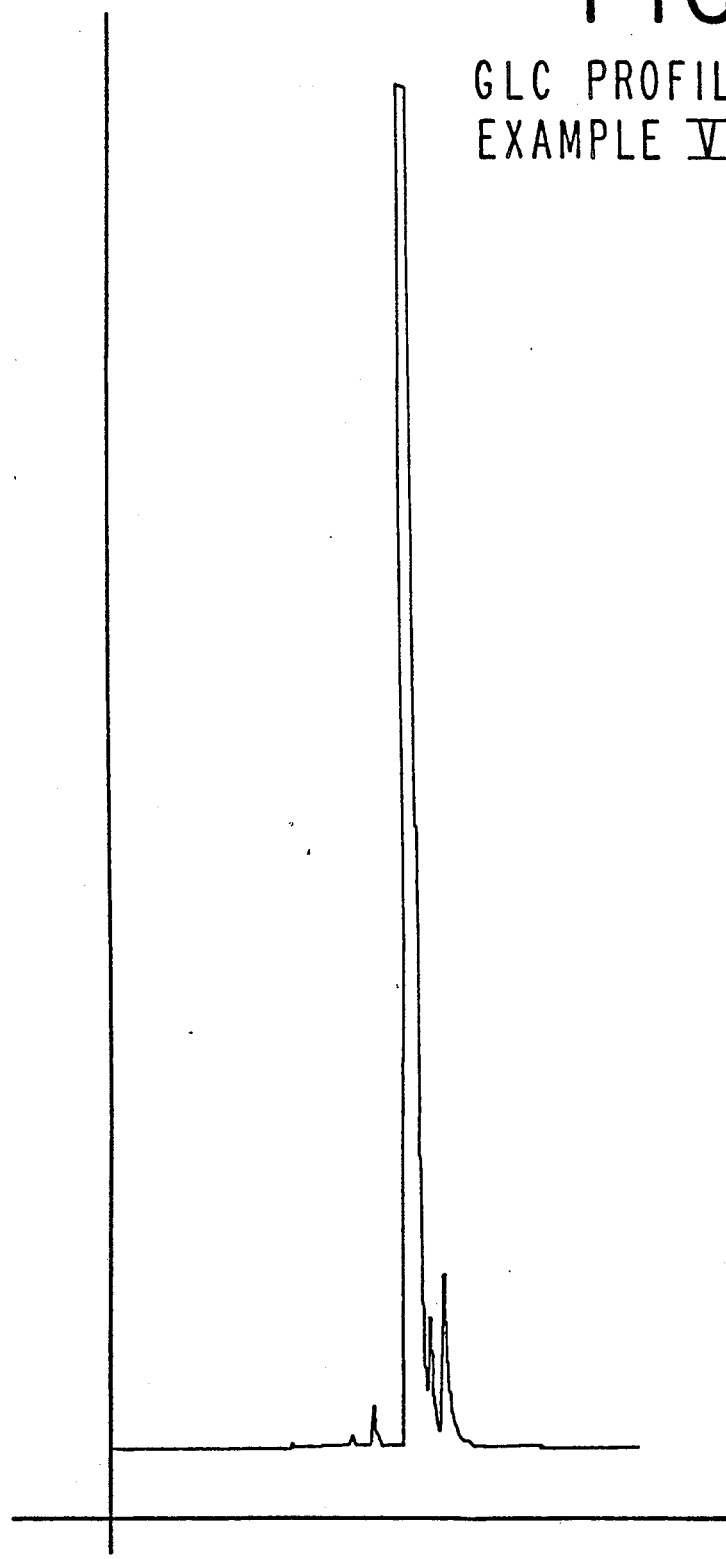

FIG. 21 is the GLC profile for distillation Fraction 5 of the reaction product of Example VI.

Figure 22:
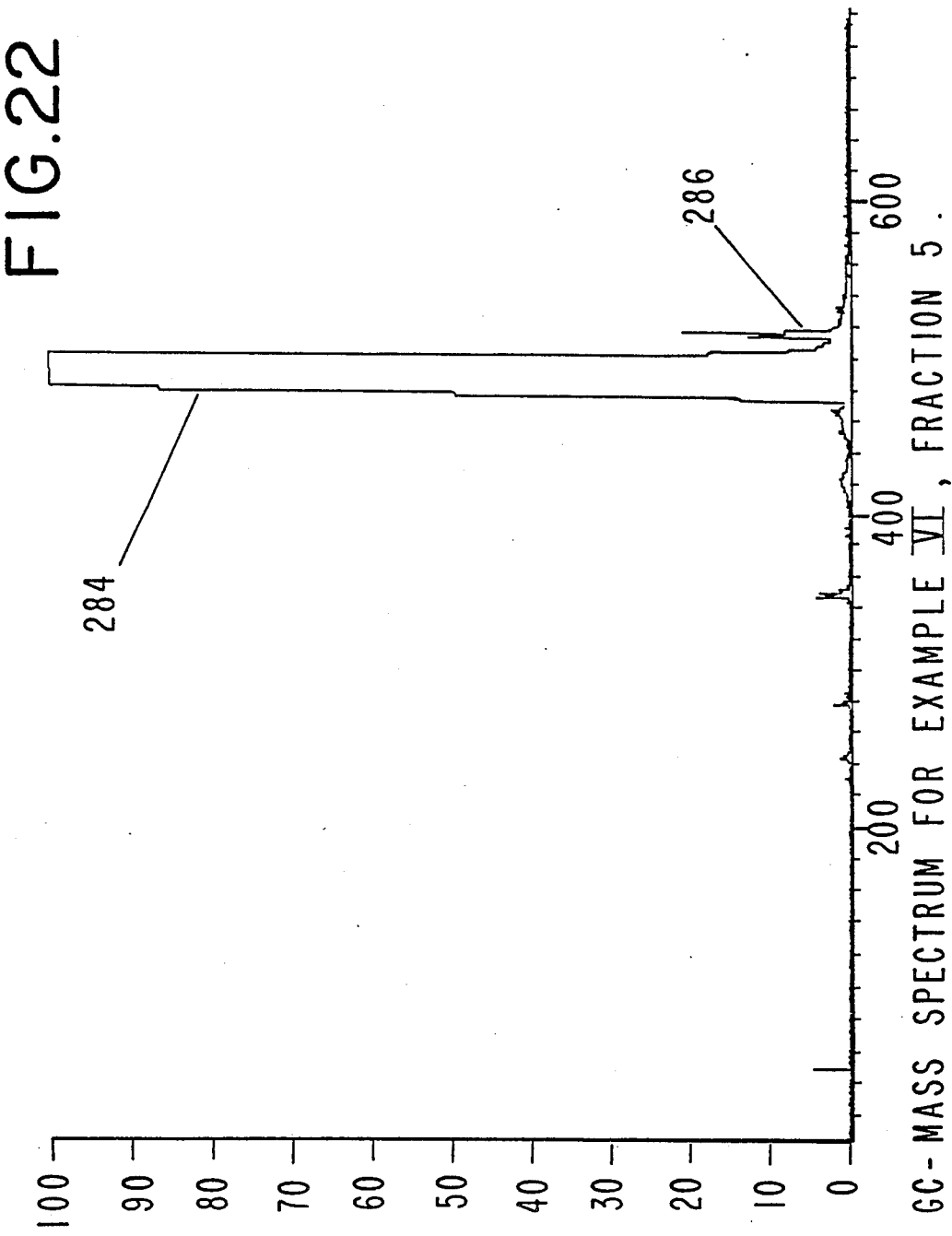
Figure 23:
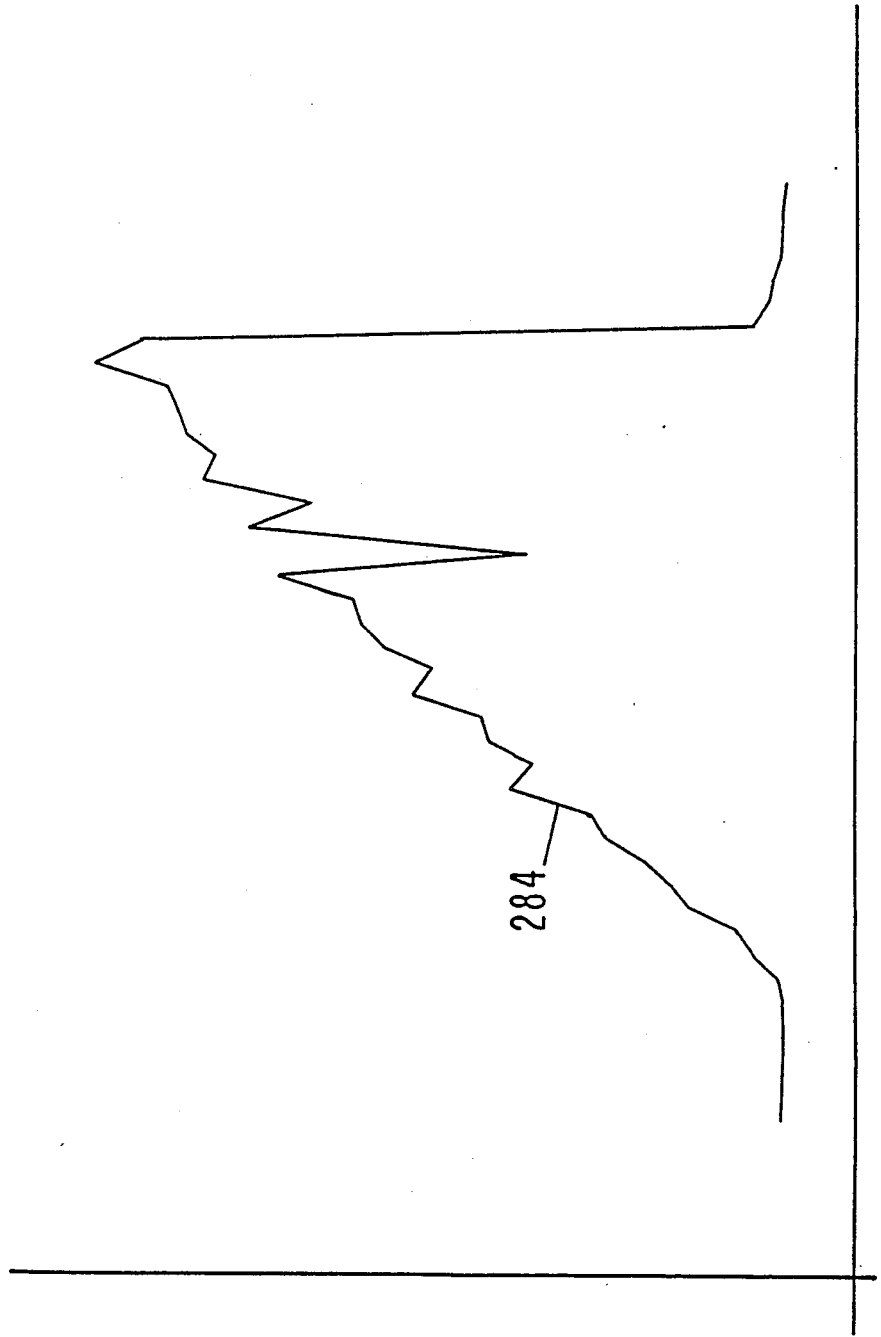

FIG. 22 is the GC mass spectrum of distillation Fraction 5 of the reaction product of Example VI containing the compound having the structure:

FIG. 23 is a detailed section of the peak indicated by reference numeral 284 of the GC mass spectrum of FIG. 22.

Figure 24:
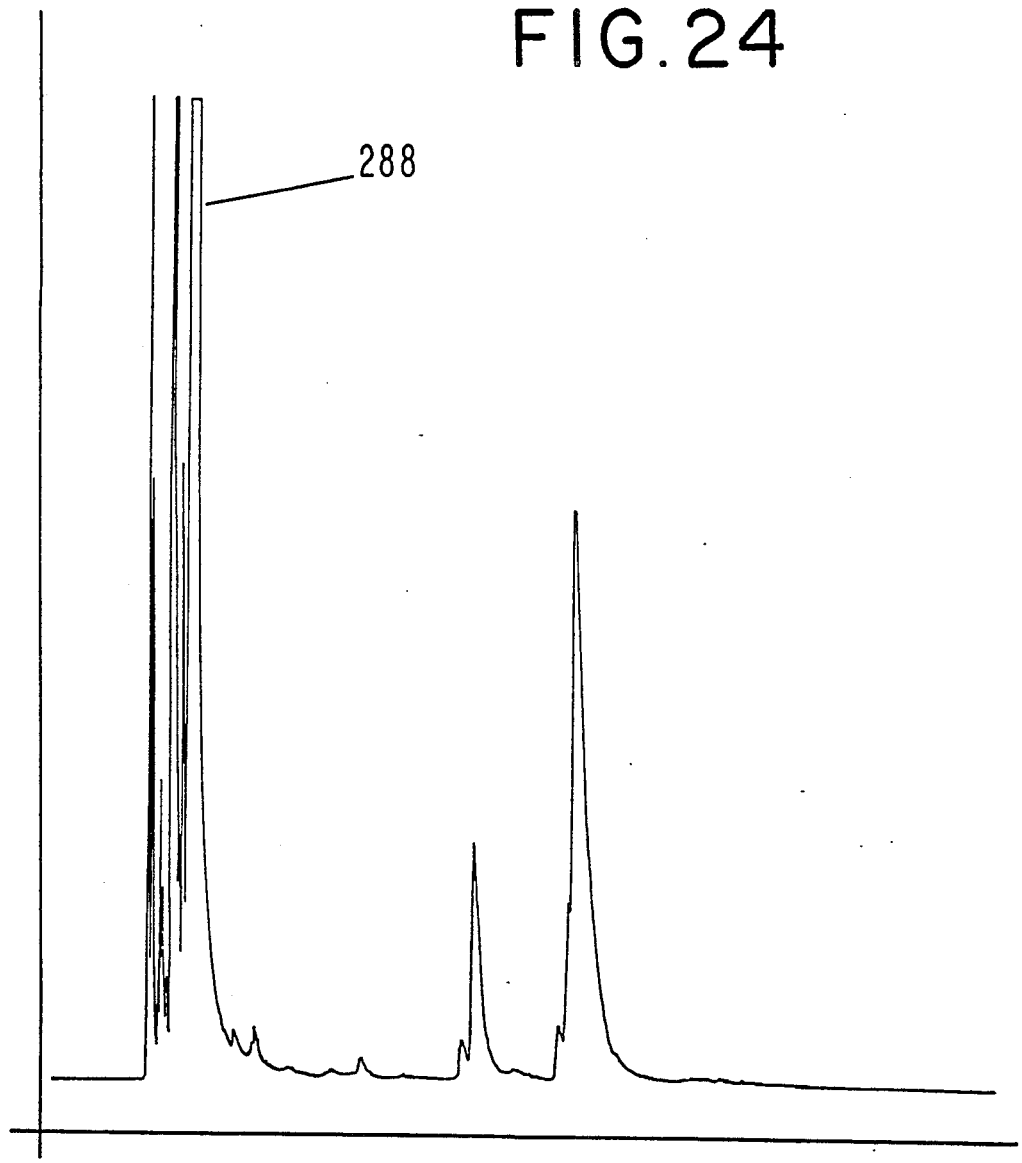

FIG. 24 is the GLC profile for the reaction product of Example VII(a) containing the compound having the structure:

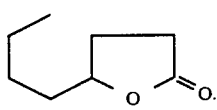

Figure 25:
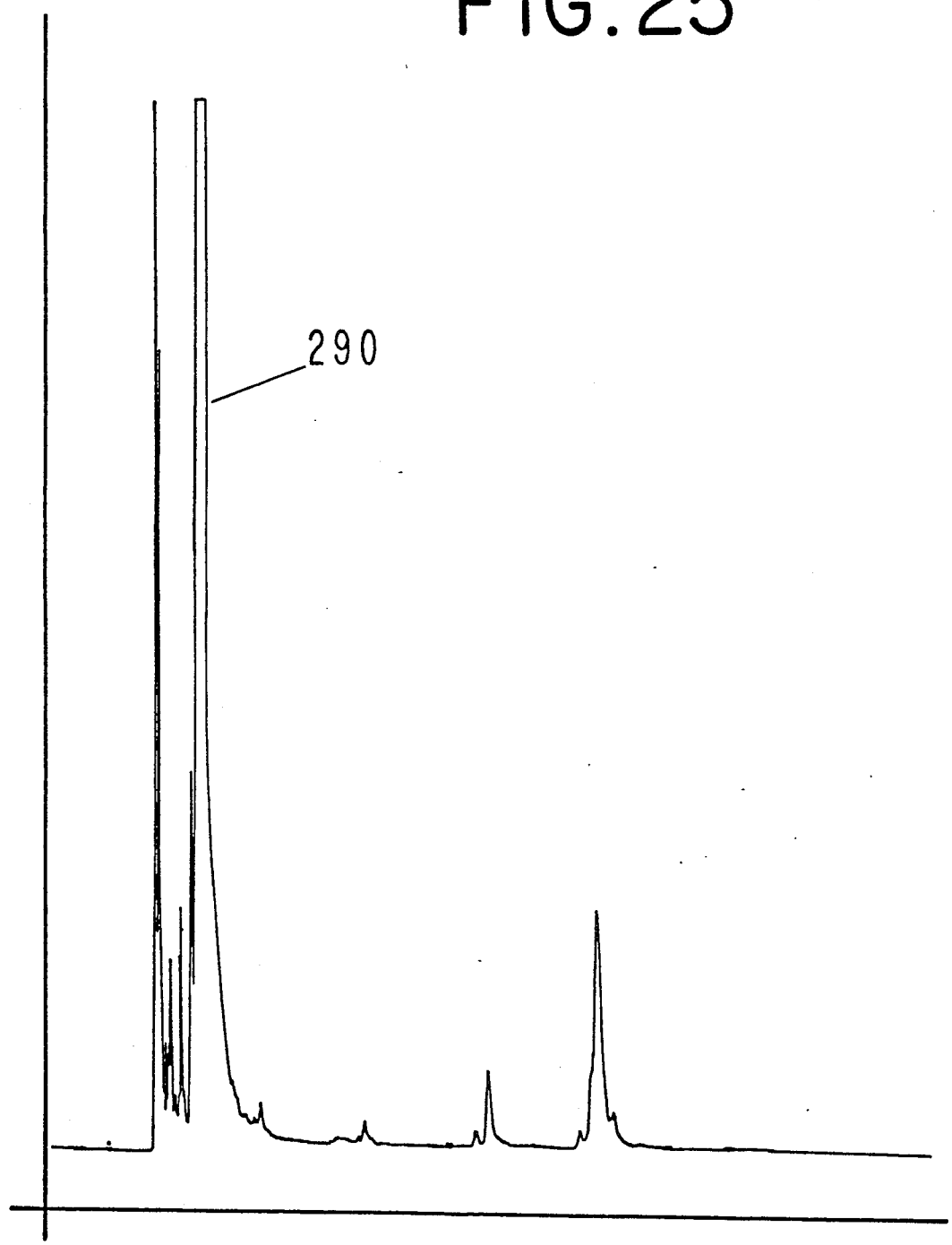

FIG. 25 is the GLC profile for the reaction product of Example VII(b) containing the compound having the structure:

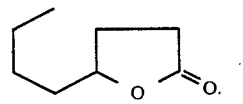

Figure 26:
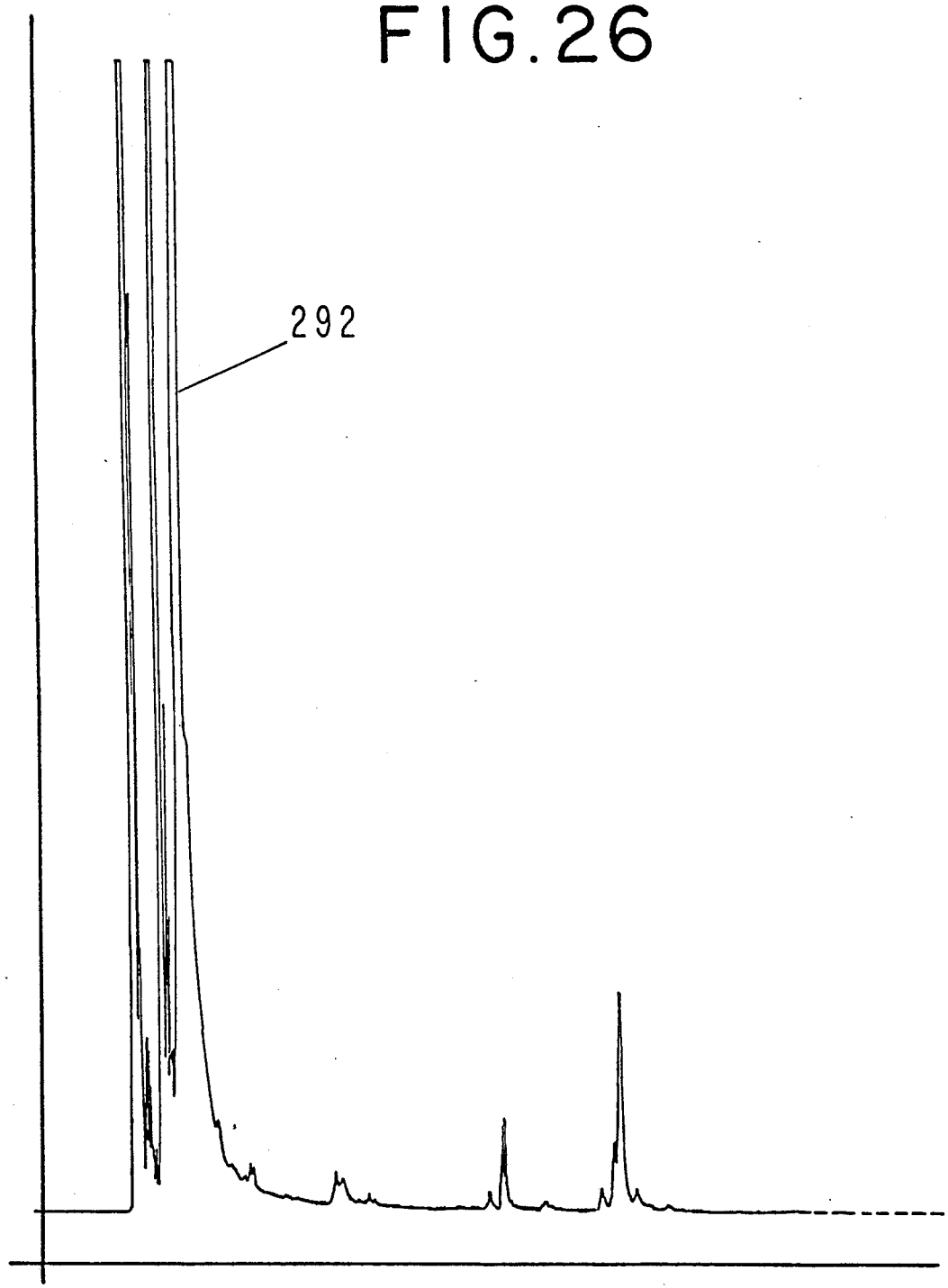

FIG. 26 is the GLC profile for the reaction product of Example VII(c) containing the compound having the structure:

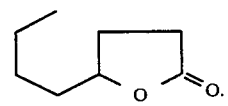

Figure 27:
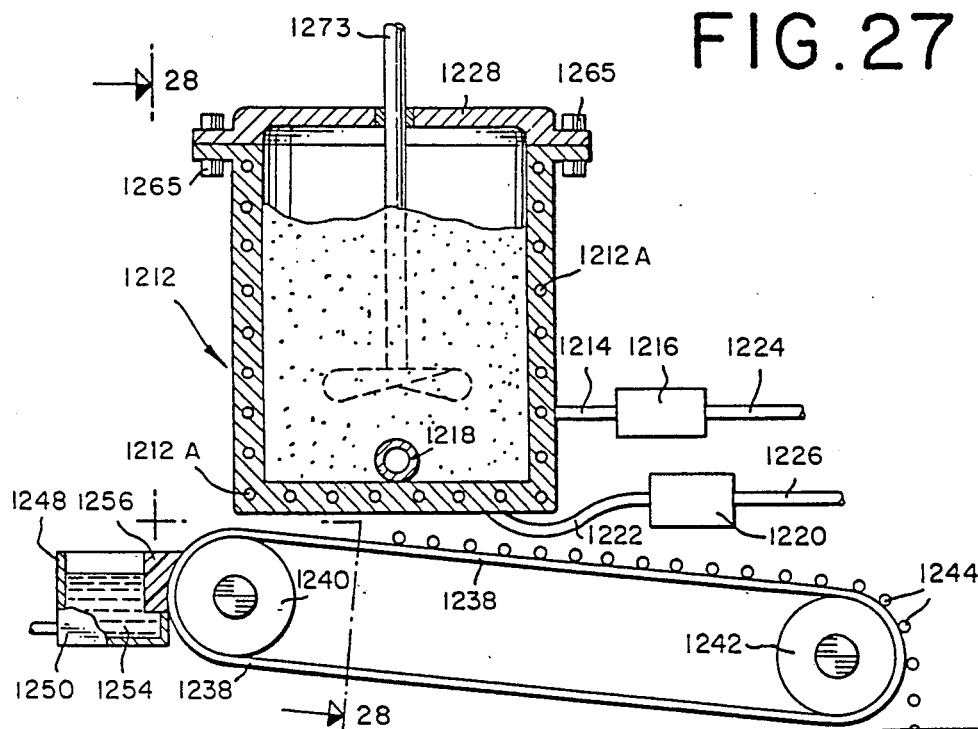

FIG. 27 represents a cut-away side elevation view of apparatus used in forming perfumed polymers which contain imbedded therein at least one of the lactone-containing compositions of our invention.

Figure 28:
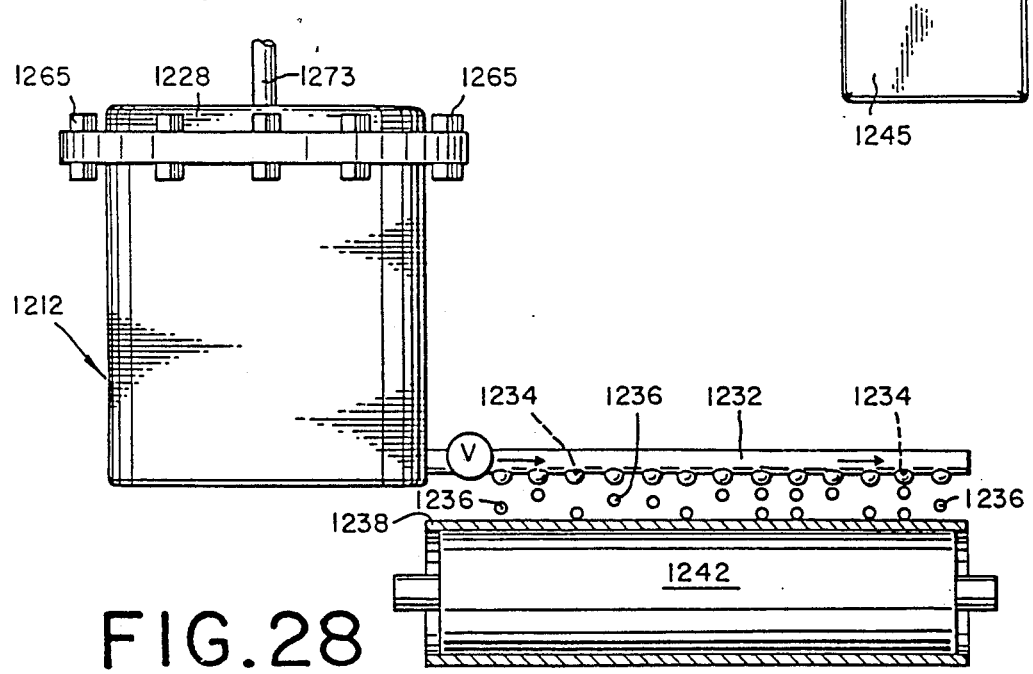

FIG. 28 is a front view of the apparatus of FIG. 27 looking in the direction of the arrows.

SUMMARY OF THE INVENTION

The present invention is directed to a microbiological process for the production of compositions containing a major proportion of gamma octalactone generically defined according to the structure:

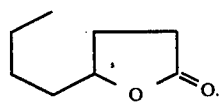

containing the stereoisomers having the structures:

and

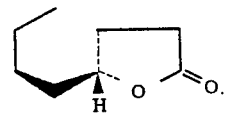

According to this process, a culture of one of the following fungi is incubated with a substrate, caprylic acid or ethyl caprylate defined according to the generic structure:

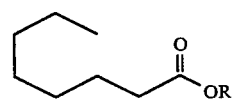

wherein R is ethyl or hydrogen to form the gamma hydroxy acid or ester defined according to the structure:

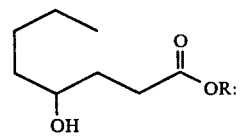

Mortierella isabellina, ATCC 44583;
Mortierella isabellina, ATCC 38063;
Syncephalastrum racemosum, NRRL A-5889;
Mortierella isabellina, IFO 7884;
Mortierella ramanniana var. angulispora, IFO 8187;
Mortierella isabellina, CBS 221.29;
Mortierella isabellina, IFO 7873;
according to the reaction:

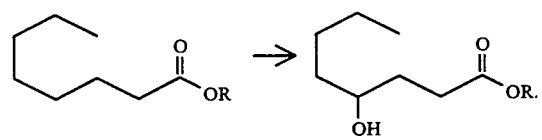

The resulting ester or carboxylic acid is then heated in the presence of acid (as by distillation and/or evaporation) to yield the desired lactone according to the reaction:

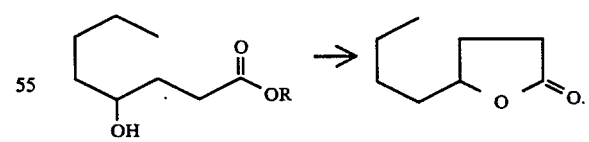

The resulting acid or ester is usually an optical isomer defined according to one of the generic structures:

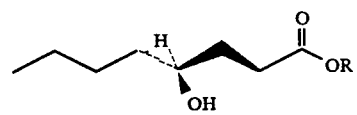

and/or

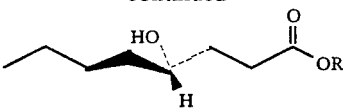

or a mixture of such isomers with either the dextro or laevo rotatory isomer being the predominant isomer. Such stereo isomers yields stereoisomers of the resulting octalactones defined according to the structures:

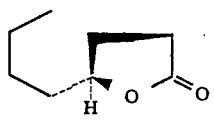

and

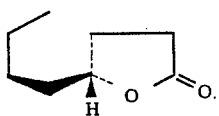

Along with the gamma octalactone, minor amounts of other products are also produced when using the above-mentioned organisms, to wit, the compounds having the structures:

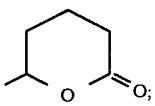

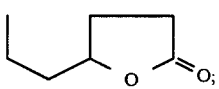

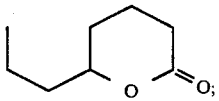

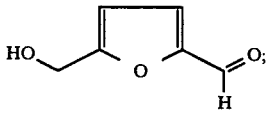

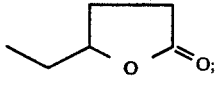

and

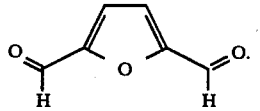

The neutrient broth used according to the process of this invention includes the usual sources of nitrogen, carbohydrates, minerals and oxygen. Incubative fermentation conditions used according to the process include any pH, temperature, substrate concentration and substrate feed rate which will maintain the viability of the culture.

The inventive process may be conducted in a batch or continuous mode of operation. In a batch fermentation, the nutrient broth, culture and substrate are combined and fermented until the lactone concentration becomes constant. In a continuous process, the substrate in the nutrient broth may be continuously recirculated through a fermentation reactor with the provision that substrate and product are respectively added and removed from the recirculating broth.

In carrying out the present invention, cultivation and fermentive incubation of the fungus are accomplished in an aqueous medium in the presence of the usual nutrient substances. A suitable medium is one which contains carbon sources, nitrogen sources, inorganic salts and growth factors. Among the suitable carbon sources are, for example, glucose, fructose, xylose, sucrose, maltose, lactose, mannitol, sorbitol, glycerol, corn syrup and corn syrup solids. Examples of suitable nitrogen sources include organic and inorganic nitrogen-containing substances such as peptone, corn steep liquor, meat extract, yeast extract, casein, urea, amino acids, ammonium salts, nitrates, enzymatic digest of soy, and mixtures thereof.

Examples of inorganic salts include the phosphate and sulfate salts of magnesium, sodium, calcium and potassium.

These nutrients may be supplemented with, for example, one or more vitamins of the "B" group and one or more trace minerals such as iron, manganese, cobalt and copper as desired.

For the nutrient broth, it is preferred to utilize dextrose at a concentration of from about 2 up to about 20 weight percent, preferably at about 10 weight percent. It is also preferred to employ "B" vitamins either as a separate supplement or in the form of a yeast extract. The kind and amounts of the above-mentioned additives can be determined by applying the general knowledge in the art for the cultivation of microorganisms.

In a typical procedure, one of the fungi as set forth below:

*Mortierella isabellina*, ATCC 44583;
*Mortierella isabellina*, ATCC 38063;
*Syncephalastrum racemosum*, NRRL A-5889;
*Mortierella isabellina*, IFO 7884;
*Mortierella ramanniana* var. angulispora, IFO 8187;
*Mortierella isabellina*, CBS 221.29;
*Mortierella isabellina*, IFO 7873;

is first cultivated in inoculum quantities to produce a mature culture in nutrient broth. The culture is inoculated into a fermentor nutrient broth and allowed to establish itself. The substrate is then added and fermentation continued until a steady concentration of lactone is present.

The cultivation and fermentative incubation of the fungus can be carried out as a stationary culture or as a submerged culture (e.g., shake-flask, fermentor), preferably under aerobic conditions. Cultivation and incubation may proceed in a pH range of from about 3 up to about 9, preferably in the range of about 5 to about 7. The pH may be regulated by the addition of an inorganic or organic acid or base such as hydrochloric acid, acetic acid, sodium hydroxide, calcium carbonate, ammonia, ion-exchange resins, or by the addition of a buffer such as a phosphate or phthalate. The incubation temperature is suitably maintained at between about 18° C. up to about 31° C., with a range of from about 26°-28° C. being preferred.

In accordance with another typical procedure of the present invention, the process is conveniently carried out by adding the substrate to the culture medium at the onset of cultivation, under aerobic conditions. Alternatively, the substrate may be added either alone or in combination with another carbon source, such as glucose, during fermentative incubation, or when cultivation is complete. It is preferable to add the substrate to the culture medium during the period of from 4 up to 24 hours after the growth of the culture in the fermentative broth has commenced. Desirable results can be obtained when the substrate is added continuously over the entire fermentation after an initial fungal cultivation period of from 3 up to 12 hours. A preferred feed rate for this continuous addition is from about 0.01 up to 1 grams per hour per liter with a preferred range of from 0.6 up to 0.8 grams per hour per liter. The concentration of the substrate in the medium may vary depending on the conditions employed. In practice, the concentration of the substrate in the medium may conveniently vary from 0.01% up to about 10% with a preferable concentration of about 1% by weight, consistent with the manner in which it is added to the culture.

Under the usual conditions, mixtures of optically active lactones having the structures:

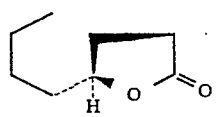

and

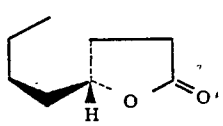

are produced.

Depending on the pH, oxygen flow rate, nutrients and whether R is ethyl or hydrogen, the concentrations of side products will vary, these side products being the compounds having the structures:

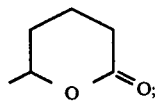

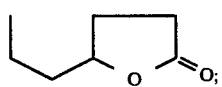

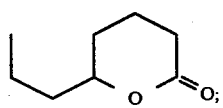

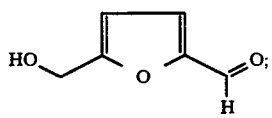

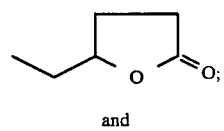

and

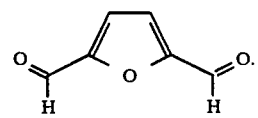

The reaction period for carrying out the reaction, to wit:

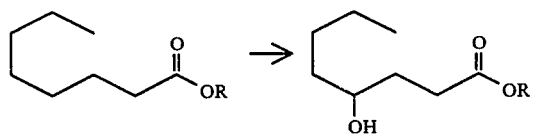

varies according to the specific incubation parameters, such as the strain of microorganism employed, the composition of the culture medium and whether the substrate used is the ethyl caprylate ester having the structure:

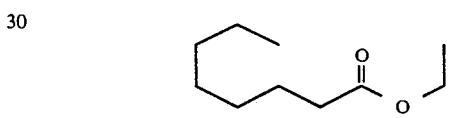

or caprylic acid having the structure:

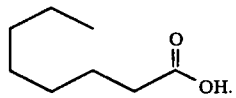

In general, shake flask cultures require between 100 and 200 hours, preferably between 120 and 150 hours, depending upon the microbial strain and the substrate utilized. However, when a fermentor is used, the fermentation period may be reduced to 40–50 hours.

The incubation is carried out under aerobic conditions, wherein the dissolved oxygen content in the incubation broth is from 20 to 100% by weight, preferably 30% to 80%. Also, preferably, the substrate is maintained in continuous contact with the aqueous phase and the microorganism. Generally, vigorous stirring or shaking is satisfactory, but if desired a surface active agent, such as TWEEN ®80, can be added to aid in the dispersion of the substrate. Conventional antifoam agents such as silicone oils, polyalkylene glycol derivatives, or soya oil can be used to control foaming.

The form in which the microorganisms are used for the fermentation is not critical. The fermentation may be carried out using the cells of the microorganism isolated from the culture solution, or with an enzyme extract isolated from the cells in a known manner. In the latter case, the reaction can be conveniently carried out in an aqueous solution, for example, in a buffer solution, in a physiological saline solution, in a fresh nutrient solution, or in water. The isolated cells or an enzyme extract thereof may be immobilized on a solid support and the desired transformation conducted separately. It will be convenient to employ the immobilized form of the enzyme extract in a continuous process. The fermentation of the substrate may also be effected by mutants of the fungus.

The progress of the fermentative production of the hydroxy-carboxylic acid or hydroxy carboxylic acid ester having one or both of the structures:

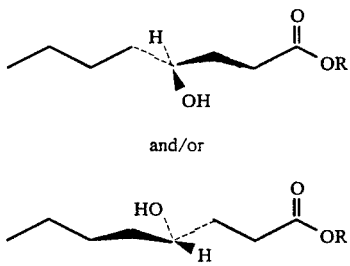

and/or can be monitored by assaying for hydroxy acid or hydroxy ester concentration using standard analytical techniques such as chromatography (gas-liquid, thin layer or high pressure liquid) and spectroscopy such as IR and NMR. The fermentation can also be followed by measuring consumption of substrate, glucose, oxygen or by measuring pH changes. The fermentation is generally terminated when all of the substrate has been consumed or when no further increase in the hydroxy acid or hydroxy ester concentration is observed.

When the resulting material is sterilized as by heating, the hydroxy acid or hydroxy ester is formed into one or both of the lactones defined according to the structures:

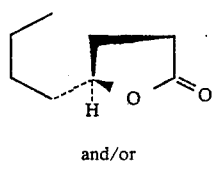

and/or

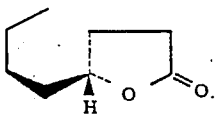

Necessarily, the reaction itself will cause in situ formation of lactones in a lower concentration. Resultant sterilization and subsequent distillation gives rise to complete conversion of the hydroxy acid and hydroxy ester to the lactones having the structures:

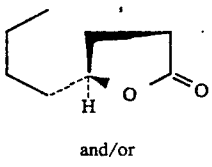

and/or

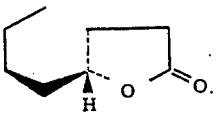

The present invention produces unexpectedly high yields of the octalactones defined according to the structures:

and/or

compared with prior art methods which yield products having a much lower yield.

Hereinafter, the term "lactone derivative(s)" will be understood to mean the reaction products subsequently purified containing substantially all of the compounds having the structures:

and/or

together with one or more of the side products having the structures:

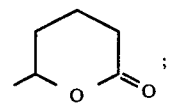

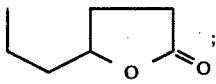

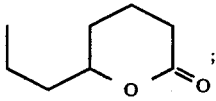

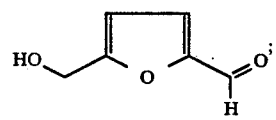

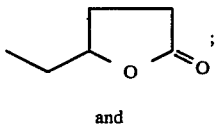

and

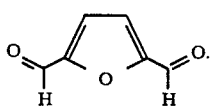

The lactone derivative(s) and one or more auxiliary perfume ingredients, including, for example, hydrocarbons, alcohols, ketones, aldehydes, nitriles, esters other than the lactone derivatives of our invention, ethers, synthetic essential oils, and natural essential oils may be admixed so that the combined odors of the individual components produce a pleasant and desired fragrance, particularly and preferably in the fruity area (e.g., peach and apricot aromas). Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh-smelling materials.

In perfume compositions, it is the individual compositions which contribute to their particular olfactory characteristics, however, the overall sensory effect of the perfume composition will be at least the sum total of the effects of each of the ingredients. Thus, one or more of the lactone derivative(s) of our invention can be used to alter, modify or enhance the aroma characteristics of a perfume composition, for example, by utilizing or moderating the olfactory reaction contributed by another ingredient in the composition.

The amount of lactone derivative(s) of our invention which will be effective in perfume compositions as well as in perfumed articles and colognes depends upon many factors including the other ingredients, their amounts and the side effects which are desired. It has been found that perfume compositions containing as little as 0.005% of lactone derivative(s) or even less (e.g., 0.002%) can be used to impart sweet, fruity (peach and apricot) aromas to soaps, cosmetics, detergents including anionic, cationic, nonionic and zwitterionic solid or liquid detergents, perfumed polymers and other products. The amount employed can range up to 70% of the fragrance components and will depend upon the consideration of cost, nature of the end product, the effect desired on the finished product and the particular fragrance sought.

The lactone derivative(s) of our invention are useful (taken alone or taken together with other ingredients in perfume compositions) in detergents, soaps, space odorants and deodorants, perfumes, colognes, toilet waters, bath preparations, hair preparations such as lacquers, brilliantines, pomades and shampoos; cosmetic preparations such as creams, deodorants, hand lotions and sun screens; powders such as talcs, dusting powders, face powders and the like.

As little as 0.25% of the lactone derivative(s) will suffice to impart an intense, sweet, fruity (peach and apricot) aroma to floral perfume formulations. Generally no more than 5% of the lactone derivative(s) based on the ultimate end product is required to be used in the perfume compositions.

Furthermore, as little as 0.25% of the lactone derivative(s) will suffice to impart such aromas to perfumed articles per se, whether in the presence of other perfume materials or whether used by themselves.

Thus, the range of use of the lactone derivative(s) of our invention in perfumed articles, e.g., perfumed polymers and solid or liquid anionic, cationic, nonionic or switterionic solid or liquid detergents, may vary from 0.25% up to about 5% by weight based on the total weight of the perfumed article.

In addition the perfume composition or fragrance composition of our invention can contain a vehicle or carrier for the lactone derivative(s). The vehicle can be a liquid such as a non-toxic alcohol, e.g., ethanol, a non-toxic glycol, e.g., propylene glycol, or the like. The carrier can also be an absorbent solid such as a gum (e.g., gum arabic or xanthan gum or guar gum) or components for encapsulating the composition by means of coacervation (such as by gelatin) or by means of formation of a polymer around a liquid center (as by using a urea formaldehyde prepolymer to form a polymeric capsule around a perfume composition center).

It will be appreciated from the present disclosure that the lactone derivative(s) according to the present invention can be used to alter, vary, fortify, modify, enhance or otherwise improve the flavor of a wide variety of materials which are ingested, consumed or otherwise organoleptically sensed.

The terms "alter" and "modify" in their various forms will be understood herein to mean the supplying or imparting of a flavor character or note to an otherwise bland, relatively tasteless substance, or augmenting an existing flavor characteristic where the natural flavor is deficient in some regard or supplementing the existing flavor impression to modify its organoleptic character.

The term "enhance" is intended herein to mean the intensification (by use of the lactone derivative of our invention) of a flavor or aroma note or nuance in a tobacco flavor or foodstuff or perfume composition or perfumed article without changing the quality of said note or nuance.

A "flavoring composition" is taken to mean one which contributes a part of the overall flavor impression by supplementing or fortifying a natural or artificial flavor in a material or one which supplies substantially all the flavor and/or aroma character to a consumable article.

The term "foodstuff" as used herein includes both solid and liquid ingestible materials for man or animals which materials usually do, but need not, have nutritional value. Thus, foodstuffs include meats, gravies, soups, convenience foods, malt, alcoholic and other beverages, milk and dairy products, seafoods, including fish, crustaceans, mollusks and the like, candies, vegetables, cereals, soft drinks, snacks, dog and cat foods, other veterinary products, and the like. The lactone derivative(s) of our invention are also useful in tobacco flavorants and flavor enhancers.

The term "tobacco" will be understood herein to mean natural products such as, for example, burley, Turkish tobacco, Maryland tobacco, flue-cured tobacco and the like including tobacco-like or tobacco-based products such as reconstituted or homogenized leaf and the like as well as toacco substitutes intended to replace natural tobacco such as lettuce and cabbage leaves and the like. The tobaccos and tobacco products in which the lactone derivative(s) of our invention are useful including those designed or used for smoking such as in cigarettes, cigar and pipe toacco, as well as products such as snuff, chewing tobacco and the like.

When the lactone derivative(s) of this invention are used in a flavoring composition, they can be combined with conventional flavoring materials or adjuvants. Such co-ingredients or flavor adjuvants are well known in the art for such and have been extensively described in the literature. Requirements of such adjuvant materials are: (1) that they be non-reactive with the lactone derivative(s) of our invention; (2) that they be organoleptically compatible with the lactone derivative(s) of our invention whereby the flavor of the ultimate consumable material to which the lactone derivative(s) are added is not detrimentally affected by the use of the adjuvant; (3) that they be ingestibly acceptable and thus non-toxic or otherwise non-deleterious. Apart from these requirements, conventional materials can be used and broadly include other flavor materials, vehicles, stabilizers, thickeners, surface active agents, conditioners, and flavor intensifers.

Such conventional flavoring materials include saturated fatty acids, unsaturated fatty acids and amino acids; alcohols including primary and secondary alcohols, esters, carbonyl compounds including ketones and aldehydes; lactones; other cyclic organic materials including benzene derivates, allicyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate; magnesium glutamate, calcium glutamate, guanylates and inosinates; natural flavoring materials such as cocoa, vanilla and caramel; essential oils and extracts such as anise oil, clove oil and the like and artificial flavoring materials such as vanillin and the like.

Specific preferred flavor adjuvants are as follows:
anise oil;
ethyl-2-methyl butyrate;
vanillin;
cis-3-heptenol;
cis-3-hexenol;
trans-2-heptenol;
cis-3-heptenal;
butyl valerate;
2,3-diethyl pyrazine;
methyl cyclopentenolone;
benzaldehyde;
valerian oil;
3,4-dimethoxyphenol;
amyl acetate;
amyl cinnamate;
gamma butyryl lactone;
furfural;
trimethyl pyrazine;
phenyl acetic acid;
isovaleraldehyde;
ethyl maltol;
ethyl vanillin;
ethyl valerate;
ethyl butyrate;
cocoa extract;
coffee extract;
peppermint oil;
spearmint oil;
clove oil;
anethol;
cardamom oil;
wintergreen oil;
cinnamic aldehyde;
ethyl-2-methyl valerate;
gamma hexenyl lactone;
2,4-decadienal;
2,4-heptadienal; and
butylidene phthalide.

According to another aspect of our invention, an organoleptically improved smoking tobacco product and additives therefor as well as methods of making the same which overcome specific problems heretofore encountered in which specific Turkish, oriental-like aromas prior to smoking and improved Turkish, oriental aromas on smoking in the main stream and the side stream are created or enhanced or modified or augmented and may be readily controlled and maintained at the desired uniform level regardless of variations in the tobacco components of the blend. In particular, low grade Virginia-type tobaccos may be upgraded using the lactone derivative(s) of our invention.

This invention further provides improved tobacco additives and methods whereby various desirable natural aromatic Turkish tobacco flavoring characteristics with oriental notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient one or more of the lactone derivative(s) of our invention.

In addition to the lactone derivative(s) of our invention, other flavoring and aroma additives may be added to the smoking tobacco material or substitute therefor either separately or in admixture with the lactone derivative(s) of our invention as follows:

I. Synthetic Materials

Beta-ethyl-cinnamaldehyde;
Eugenol;
Dipentene;
Beta-damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-1,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethyl naphtho(2,1-b) furan;
4-Hydroxy hexanoic acid, gamma lactone; and
Polyisoprenoid hydrocarbons defined in Example V of U.S. Pat. No. 3,589,372 issued on Jun. 29, 1971.

II. Natural Oils

Celery seed oi:
Coffee extract;
Bergamot oil;
Cocoa extract;;
Nutmeg oil; and
Origanum oil.

An aroma and flavoring concentrate containing one or more of the lactone derivative(s) of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of oriental and/or Turkish tobacco notes, we have found that satisfactory results are obtained if the proportion by weight of the sum total of lactone derivative(s) to smoking tobacco material is between 50 ppm and 1,500 ppm (0.005%–0.15%) of the active ingredients to the smoking tobacco material. We have further found that satisfactory results are obtained if the proportion by weight of the sum total of lactone derivative(s) used to flavoring material is between 500 and 15,000 ppm (0.05%–1.5%).

Any convenient method for incorporating the lactone derivative(s) into the tobacco product may be employed. Thus, the lactone derivative(s) taken alone or along with other flavoring additives may be dissolved in a suitable solvent such as ethanol, diethylether, and/or volatile organic solvents and the resulting solution may either be spread onto the cured, cased, and blended tobacco material or the tobacco material may be dipped into such solution. Under certain circumstances, a solution of the lactone derivative(s) taken alone or taken further together with other flavoring additives as set forth above may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor nee be treated and the thus-treated tobacco may be blended with other tobaccos before the ultimate tobacco product is formed. In such cases, the tobacco treated may have the lactone derivative(s) in excess of the amounts or concentrations above indicated so that when blended with other tobaccos, the final product will have the percentage within the indicated range.

In accordance with one specific example of our invention, an aged, cured and shredded domestic Virginia tobacco is sprayed with a 20% alcohol solution of the compound having the structure:

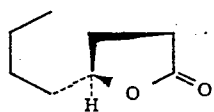

on a dry basis. Thereafter, the alcohol is removed by evaporation and the tobacco is manufactured into cigarettes by the usual techniques. The cigarette, when treated as indicated, has a desired and pleasing aroma which is detectable in the main stream and the side stream when the cigarette is smoked. The aroma is described as being sweeter, with pronounced Turkish/oriental characteristics and with improved body and enhanced tobacco character in the main stream and side stream. In addition, interesting amber nuances are imparted.

While our invention is particularly useful in the manufacture of smoking tobacco such as cigarette tobacco, cigar tobacco and pipe tobacco, othe tobacco products formed from sheeted tobacco dust or fines may also be used. Likewise the lactone derivative(s) of our invention can be incorporated with materials such as filter tip materials, seam paste, packaging materials and the like which are used along with tobacco to form a product adapted for smoking. Furthermore, the lactone derivative(s) can be added to certain tobacco substitutes of natural or synthetic origin (e.g., dried lettuce leaves) and, accordingly, by the term "tobacco" as used throughout this specification, is meant any composition intended for human consumption by smoking or otherwise when composed of tobacco plant parts or substitute material or both.

The lactone derivative(s) of our invention can be used to alter, vary, fortify, modify, enhance or otherwise improve the organoleptic properties, including flavor and/or aroma, of a wide variety of materials which are ingested, consumed, or otherwise organoleptically sensed.

The term "alter" in its various forms will be understood herein to mean the supplying or imparting of a flavor character or note to an otherwise bland, relatively tasteless substance, or augmenting the existing flavor characteristic where the natural flavor is deficient in some regard, or supplementing the existing flavor or aroma impression to modify the organoleptic character. The materials which are so altered are generally referred to herein as consumable materials.

The lactone derivative(s) of our invention are accordingly useful in flavoring compositions. Flavoring compositions are hereinafter taken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs include meats, gravies, soups, convenience foods, malt and other alcoholic or non-alcoholic beverages, milk and dairy products, (including but not limited to margarine and butter) nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

When the lactone derivative(s) produced according to this invention are used in a food flavoring composition, they can be combined with conventional flavoring materials or adjuvants. Such co-ingredients or flavoring adjuvants are well known in the art for such use and have been extensively described in the literature. Apart from the requirement that any such adjuvant material is ingestibly acceptable, and thus non-toxic or otherwise non-deleterious, conventional materials can be used and broadly include other flavor materials, vehicles, stabilizers, thickeners, surface active agents, conditioners and flavor intensifiers.

Examples of preferred co-flavoring adjuvants are:
Methyl thiazole alcohol (4-methyl-5-beta-hydroxyethyl thiazole;
2-Methyl butanethiol;
4-Mercapto-2-pentanone;

3-Mercapto-2-pentanone;
1-Mercapto-2-propanone;
Benzaldehyde;
Furfural;
Furfuryl alcohol;
2-Mercapto propionic acid;
Alkyl pyrazine;
Methyl pyrazine;
2-Ethyl-3-methyl pyrazine;
Tetramethyl pyrazine;
Polysulfides;
Dipropyl disulfide;
Methyl benzyl disulfide;
Alkyl thiophenes;
2-Butyl thiophene;
2,3-Dimethyl thiophene;
5-Methyl furfural;
Acetyl furan;
2,4-Decadienal;
Guiacol;
Phenyl acetaldehyde;
β-Decalactone;
d-Limonene;
Acetoin;
Amyl acetate;
Maltol;
Ethyl butyrate;
Luvulinic acid;
Piperonal;
Ethyl acetate;
n-Octanal;
n-Pentanal;
n-Hexanal;
Diacetyl;
Monosodium glutamate;
Monopotassium glutamate;
Sulfur-containing amino acids, e.g., Cysteine;
Hydrolyzed vegetable protein;
2-Methylfuran-3-thiol;
2-Methyldihydrofuran-3-thiol;
2,5-Dimethylfuran-3-thiol;
Hydrolyzed fish protein;
Tetramethyl pyrazine;
Propylpropenyl disulfide;
Propylpropenyl trisulfide;
Diallyl disulfide;
Diallyl trisulfide;
Dipropenyl disulfide;
Dipropenyl trisulfide;
4-Methyl-2-[methylthio)-ethyl]-1,3-dithiolane;
4,5-Dimethyl-2-[methylthio)ethyl]-1,3-dithiolane;
4,5-Dimethyl-2-(methylthiomethyl)-1,3-dithiolane; and
4-Methyl-2-(methylthiomethyl)-1,3-dithiolane.

The lactone derivative(s) of our invention or compositions incorporating them, as mentioned above, can be combined with one or more vehicles or carriers for adding them to the particular product. Vehicles can be edible or otherwise suitable materials such as ethyl alcohol, propylene glycol, water and the like. Carriers include materials such as gum arabic, carrageenan, xanthan gum, guar gum and the like.

The lactone derivative(s) prepared according to this invention can be incorporated with the carriers by conventional means such as spray-drying, drum-drying and the like. Such carriers can also include materials for coacervating the lactone derivative(s) of our invention to provide encapsulated products. When the carrier is an emulsion the flavoring composition can also contain emulsifiers such as mono- and diglycerides or fatty acids and the like. With these carriers or vehicles, the desired physical form of the composition can be prepared.

The quantity of lactone derivative(s) utilized should be sufficient to impart the desired flavor characteristic to the product, but on the other hand, the use of an excessive amount of the lactone derivative(s) is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage if any to which the product will be subject; and the preconsumption treatment, such as baking, frying, and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate composition contain from about 0.1 parts per million (ppm) to about 500 ppm of the lactone derivative(s).

The lactone derivative(s) of our invention when utilized in flavoring compositions can be varied over a wide range depending upon the particular flavor nuances desired to be added to the foodstuff. Thus amounts of the lactone derivative(s) of our invention may be contained in flavoring materials from about 1 ppm up to about 50% by weight of the flavoring composition. Indeed, the compounds having the structures:

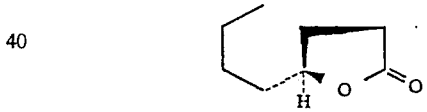

and

as well as the hydroxy esters having the structures:

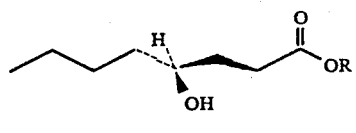

and

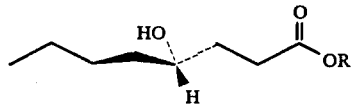

wherein R is ethyl or hydrogen may be utilized in margarine flavors at levels of between about 1% and about 50%.

DETAILED DESCRIPTION OF THE DRAWINGS

Figure 1:
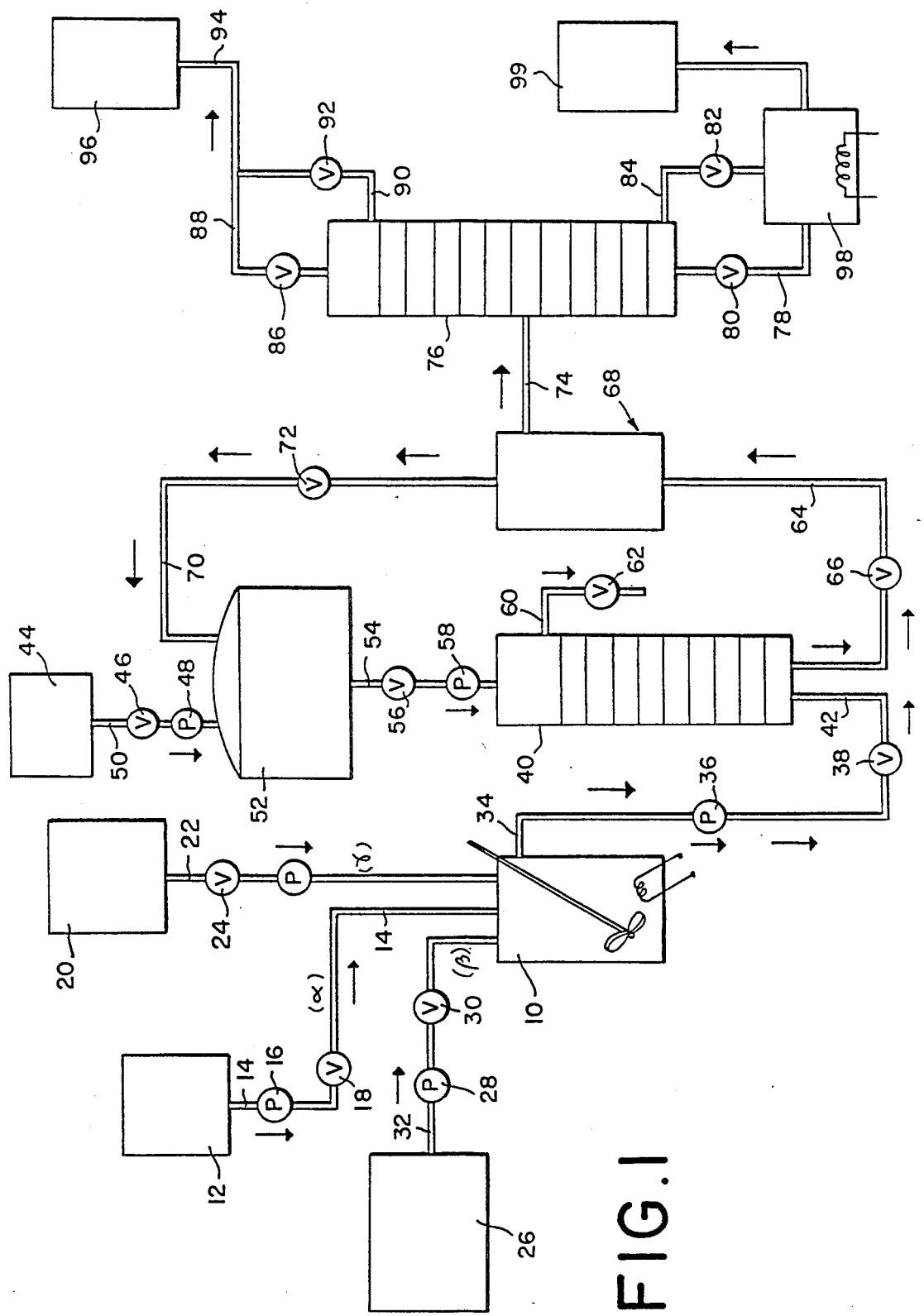
FIG. 1 is a block flow schematic diagram setting forth apparatus used in carrying out a process for the production of the novel compositions of matter of our invention including the lactone having the structure.

FIG. 1 is the block flow diagram setting forth in schematic form the apparatus used in carrying out the process for producing the lactone derivative(s) of our invention. Into fermentor 10, medium 12 is passed through line 14 using pump 16 and control valve 18. The addition of the medium into the fermentor 10 is followed by the addition of prepared culture from location 26 through line 32 past pump 28 using control valve 30. The addition of the prepared culture to the medium is followed by the addition of the substrate from location 20 through line 22 using control valve 24.

The fermentation is carried out for a period of, for example, 48 hours.

The fermentation broth is then passed through line 34 using pump 36 past control valve 38 through line 42 into extractor 40 wherein extractant from location 44 and from feed tank 52 is passed through line 54 using pump 58 past control valve 56 into the extractor 40. The extraction takes place in extractor 40 and the lactone-containing extraction solvent is evaporated in evaportor 68 after being fed into the evaporator through line 64 using control valve 66. The extraction solvent from location 44 is passed through line 50 using pump 48 past control valve 46 into feed tank 52. Solvent evaporated from the evaporator 68 passes through line 70 past control valve 72 into the feed tank 52 recycled and original extraction solvent from feed tank 52 passes through line 54 using pump 58 past control valve 56 into the extractor 40.

The resulting product containing a high proportion of gamma octalactone having the structure:

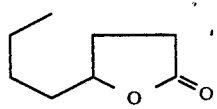

is passed through line 74 into distillation column 76 wherein the octalactone is distilled overhead using reflux head 88 having therein control valve 86 and 92 and recycle line 90. The octalactone passes through line 94 into holding tank 96 where it may further be distilled or extracted and used for its organoleptic properties. The bottoms from distillation column 76 passes through line 78 using control valve 80 into reboiler 98 where reboiled product passes through line 84 using control valve 82. The bottoms from the distillation column 76 are held in holding tank 99.

FIG. 2 is the GLC profile for the reaction product of Example I(a). The peak indicated by reference numeral 200 is the peak for methyl caprylate having the structure:

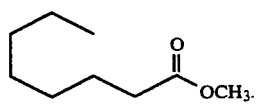

The peak indicated by reference numeral 202 is the peak for ethyl caprylate having the structure:

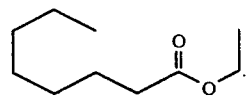

The peak indicated by reference numeral 204 is the peak for gamma octalactone having the structure:

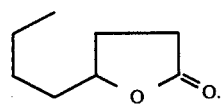

(Conditions: 50 m×0.31 mm OV-1 column programmed from 75°-225° C. at 2.0° C. per minute).

FIG. 3 is the GLC profile for the reaction product of Example I(b). The peak indicated by reference numeral 206 is the peak for methyl caprylate having the structure:

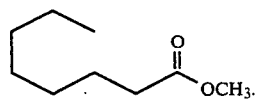

The peak indicated by reference numeral 208 is the peak for ethyl caprylate having the structure:

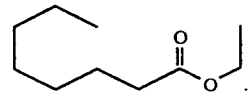

The peak indicated by reference numeral 210 is the peak for gamma octalactone having the structure:

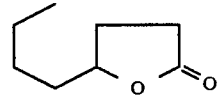

(Conditions: 50 m×0.31 mm OV-1 column programmed from 75°-225° C. at 2.0° C. per minute).

FIG. 4 is the GLC profile for the reaction product of Example I(c). The peak indicated by reference numeral 214 is the peak for ethyl caprylate having the structure:

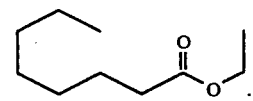

The peak indicated by reference numeral 212 is the peak for methyl caprylate having the structure:

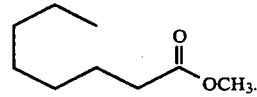

The peak indicated by reference numeral 216 is the peak for gamma octalactone having the structure:

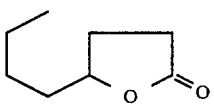

(Conditions: 50 m×0.31 mm OV-1 column programmed from 75°-225° C. at 2.0° C. per minute).

FIG. 5 is the GLC profile for the reaction product of Example I(d). The peak indicated by reference numeral 218 is the peak for methyl caprylate. The peak indicated by reference numeral 220 is the peak for ethyl caprylate. The peak indicated by reference numeral 222 is the peak for gamma octalactone. (Conditions: 50 m×0.31 mm OV-1 column programmed from 75°-225° C. at 2.0° C. per minute).

FIG. 6 is the GLC profile for the reaction product of Example I(e). The peak indicated by reference numeral 224 is the peak for methyl caprolate. The peak indicated by reference numeral 226 is the peak for ethyl caprylate. The peak indicated by reference numeral 228 is the peak for gamma octalactone. (Conditions: 50 m×0.31 mm OV-1 column programmed from 75°-225° C. at 2.0° C. per minute).

FIG. 7 is the GLC profile for the reaction product of Example I(f). The peak indicated by reference numeral 230 is the peak for methyl caprylate. The peak indicated by reference numeral 232 is the peak for ethyl caprylate. The peak indicated by reference numeral 234 is the peak for gamma octalactone. (Conditions: 50 m×0.31 mm OV-1 column programmed from 75°-225° C. at 2.0° C. per minute).

FIG. 8 is the GLC profile for the reaction product of Example I(g). The peak indicated by reference numeral 236 is the peak for methyl caprylate. The peak indicated by reference numeral 238 is the peak for ethyl caprylate. The peak indicated by reference numeral 240 is the peak for gamma octalactone. (Conditions: 50 m×0.31 mm OV-1 column programmed from 75°-225° C. at 2.0° C. per minute).

FIG. 9 is the GLC profile for the reaction product of Example III. The peak indicated by reference numeral 242 is the peak for methyl caprylate. The peak indicated by reference numeral 244 is the peak for ethyl caprylate. The peak indicated by reference numeral 246 is the peak for gamma octalactone.

FIG. 10 is the GC-mass spectrum for the reaction products of Examples II and III, combined. The peak indicated by reference numeral 248 is the peak for the compound having the structure:

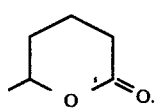

The peak indicated by reference numeral 250 is the peak for the compound having the structure:

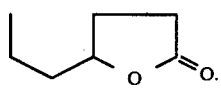

The peak indicated by reference numeral 252 is the peak for caprylic acid having the structure:

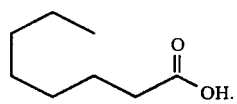

The peak indicated by reference numeral 254 is the peak for the compound having the structure:

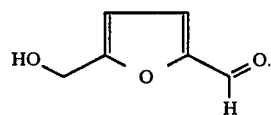

The peak indicated by reference numeral 256 is for gamma octalactone having the structure:

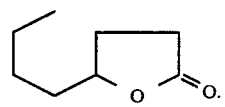

The peak indicated by reference numeral 258 is for the compound having the structure:

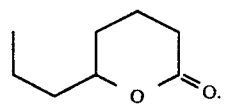

FIG. 11 is an enlargement of peaks 252 and 254 of FIG. 10. The peak indicated by reference numeral 252 is for caprylic acid having the structure:

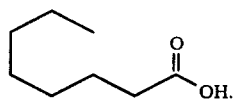

The peak indicated by reference numeral 254 is for the compound having the structure:

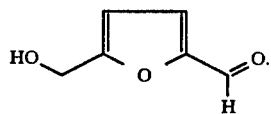

hydroxy methyl furfural.

FIG. 14 is the GLC profile for the first and second extraction of the reaction product of Example IV. The peak indicated by reference numeral 260 is the peak for gamma octalactone.

FIG. 15 is the GLC profile for the third extraction of the reaction product of Example IV. The peak indicated by reference numeral 262 is for gamma octalactone. (Conditions: 50 m×0.31 mm OV-1 column programmed at 200° C. isothermal for 10 minutes followed by 200°-225° C. at 10° C. per minute).

FIG. 17 is the GC-mass spectrum for distillation Fraction 2 of the distillation product of the reaction product of Example VI. The peak indicated by reference numeral 264 is the peak for the compound having the structure:

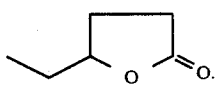

The peak indicated by reference numeral 266 is for the compound having the structure:

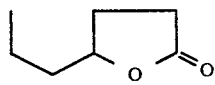

The peak indicated by reference numeral 268 is the peak for the compounds having the structures:

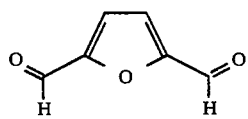

and

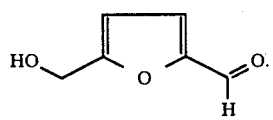

The peak indicated by reference numeral 270 is the peak for gamma octalactone having the structure:

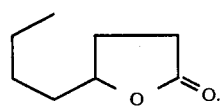

The peak indicated by reference numeral 272 is for the compound having the structure:

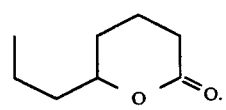

FIG. 20 is the GC-mass spectrum for distillation Fraction 4 of the distillation product of the reaction product of Example VI. The peak indicated by reference numeral 274 is the peak for the compound having the structure:

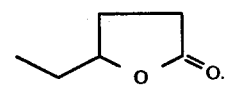

The peak indicated by reference numeral 276 is the peak for the compound having the structure:

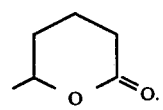

The peak indicated by reference numeral 278 is the peak for the compound having the structure:

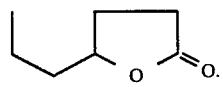

The peak indicated by reference numeral 280 is the peak for gamma octalactone having the structure:

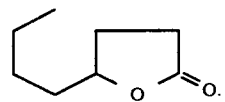

The peak indicated by reference numeral 282 is the peak for the compound having the structure:

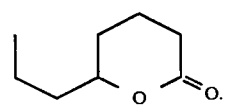

FIG. 22 is the GC-mass spectrum for distillation Fraction 5 of the distillation product of the reaction product of Example VI. The peak indicated by reference numeral 284 is for gamma octalactone having the structure:

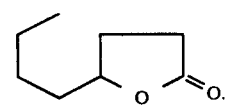

The peak indicated by reference numeral 286 is for the compound having the structure:

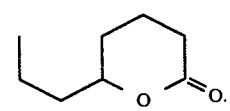

FIG. 23 is an enlargement of peak 284 of FIG. 22. Peak 284 is for gamma octalactone having the structure:

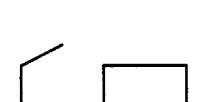

FIG. 24 is the GLC profile for the reaction product of Example VII(a). The peak indicated by reference numeral 288 is the peak for gamma octalactone having the structure:

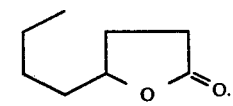

FIG. 25 is the GLC profile for the reaction product of Example VII(b). The peak indicated by reference numeral 290 is the peak for gamma octalactone having the structure:

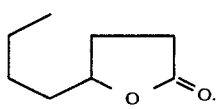

FIG. 26 is the GLC profile for the reaction product of Example VII(c). The peak indicated by reference numeral 292 is the peak for gamma octalactone having the structure:

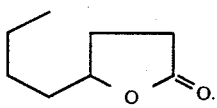

Referring to FIGS. 27 and 28, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 27 and 28, in particular, the apparatus used in producing such elements comprises a device for forming the polymer containing perfume, e.g., polyethylene or polyethylene-polyvinyl acetate of mixtures of same or polypropylene, which comprises a vat or container 1212 into which the polymer taken alone or in admixture with other copolymers and the perfuming substance which is at least one of the lactones of our invention or mixtures of lactones and other compatible perfumes is placed. The container is closed by means of an air-tight lid 1228 and clamped to the container by bolts 1265. A stirrer 1273 traverses the lid or cover 1228 in an air-tight manner and is rotatable in a suitable manner. A surrounding cylinder 1212A having heating coils which are supplied with electric current through cable 1214 from a rheostat or control 1216 is operated to maintain the temperature inside the container 1212 such that the polymer in the container will be maintained in the molten or liquid state. It has been found advantageous to employ polymers at such a temperature that the viscosity will be in the range of 90–100 sayboldt seconds. The heater 1218 is operated to maintain the upper portion of the container 1212 within a temperature range of, for example, 220°–270° C. in the case of low density polyethylene. The bottom portion of the container 1212 is heated by means of heating coils 1212A regulated through the control 1220 connected thereto through a connecting wire 1222 to maintain the lower portion of the container 1212 within a temperature range of 220°–270° C.

Thus, the polymer or mixture of polymers added to the container 1212 is heated from 10–12 hours, whereafter the perfume composition or perfume material which contains one or more of the lactones of our invention is quickly added to the melt. Generally, about 10–45 percent by weight of the resulting mixture of the perfumery substance is added to the polymer.

After the perfume material is added to the container 1212, the mixture is stirred for a few minutes, for example, 5–15 minutes and maintained within the temperature ranges indicated previously by the heating coil 1212A. The controls 1216 and 1220 are connected through cables 1224 and 1226 to a suitable supply of electric current for supplying the power for heating purposes.

Thereafter, the valve "V" is opened permitting the mass to flow outwardly through conduit 1232 having a multiplicity of orifices 1234 adjacent to the lower side thereof. The outer end of the conduit 1232 is closed so that the liquid polymer in intimate admixture with one or more of the lactones of our invention or mixture of perfume substance and one or more of the lactones of our invention, will continuously drop through the orifices 1234 downwardly from the conduit 1232. During this time, the temperature of the polymer intimately admixed with the perfumery substance in the container 1212 is accurately controlled so that a temperature in the range of from about 240°–250° C., for example, (in the case of low density polyethylene) will exist in the conduit 1232. The regulation of the temperature through the controls 1216 and 1220 is essential in order to insure temperature balance to provide for the continuous dropping or dripping of molten polymer intimately admixed with the perfume substance which is all or which contains one or more of the lactones of our invention, through the orifices 1234 at a rate which will insure the formation of droplets 1236 which will fall downwardly onto a moving conveyor belt 1238 caused to run between conveyor wheels 1240 and 1242 beneath the conduit 1232.

When the droplets 1236 fall onto the conveyor 1238, they form pellets 1244 which harden almost instantaneously and fall off the end of the conveyor 1238 into a container 1250 which is advantageously filled with water or some other suitable cooling liquid to insure the rapid cooling of each of the pellets 1244. The pellets 1244 are then collected from the container 1250 and utilized for the formation of other functional products, e.g., garbage bags and the like.

The following examples are given to illustrate embodiments of the invention as it is preferred to practice it. It will be understood that these examples are illustrative and the invention is not to be considered as restrictive thereto except as indicated in the appended claims.

All parts, proportions, percentages and ratios hereinafter referred to are by weight unless otherwise indicated.

EXAMPLE I

Production of Gamma Octalactone in Shake Flasks

Reactions:

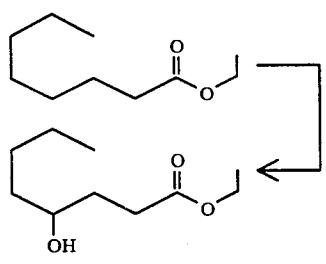

and

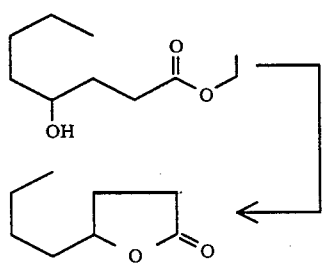

100 ml Shake flasks operating at 25° C. and 150 rpm (starting pH 4.5) are filled with medium and substrate as set forth below.

Each of the flasks is inoculated with a different organism as is shown for Examples I(a), I(b), I(c), I(d), I(e), I(f) and I(g):

EXAMPLE II

Preparation of Gamma Octalactone using *Mortierella Isabellina* IFO 7873

Reactions:

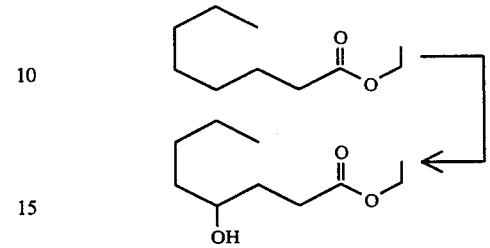

and

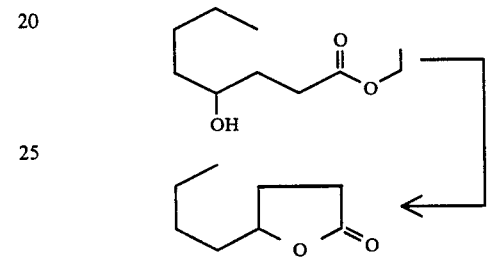

The following medium is prepared:
1% : Peptone
0.5%: Yeast extract
0.05%: TWEEN ®80
10.0%: Dextrose

*Mortierella isabellina*, IFO 7873 is placed into 100 ml of the above medium and a culture is produced. 500 ml of the above-medium is then inoculated with 2% of the above-formed culture.

A production medium is prepared as follows:
1%: Peptone
0.5%: Yeast extract
0.05% TWEEN ®80

| Medium: | Substrate: | Shake Flask Conditions: |
|---|---|---|
| 1.0% Peptone<br>0.5% Yeast extract<br>0.05% TWEEN ® 80<br>10.0% Dextrose | 1% Ethyl Caprylate | 100 ml volume<br>Temperature = 25° C.<br>Agitation = 150 rpm<br>Starting pH = 4.5 |

The results for each of the Examples are set forth below:

| Example | Organism | Time At Which Substrate Added After Commencement of Shaking | Crude Wt. of Product | %-Octalactone In Reaction Product At End of 6 Days After Addition Of Substrate |
|---|---|---|---|---|
| I(a) | *Mortierella isabellina*, ATCC 44583 | 24 hours | 0.372 grams | 1.4 |
| I(b) | *Mortierella isabellina*, ATCC 38063 | 24 hours | 0.147 grams | 8.4 |
| I(c) | *Syncephalastrum racemosum*, NRRL A-5889 | 24 hours | 0.702 grams | 4.1 |
| I(d) | *Mortierella isabellina*, IFO 7884; | 24 hours | 0.289 grams | 21.15 |
| I(e) | *Mortierella ramanniana* var. *angulispora*, IFO 8187; | 48 hours | 0.465 grams | 1.28 |
| I(f) | *Mortierella isabellina*, CBS 221.29; | 24 hours | 0.311 grams | 10.15 |
| I(g) | *Mortierella isabellina*, IFO 7873; | 24 hours | 0.441 grams | 24.56 |

All flasks were analyzed 6 days after addition of substrate.

10.0%: Dextrose.

The production medium is placed into a 9 liter fermentor equipped with a 500 rpm agitator and operating at an aeration rate of 0.5 v/v/m and a pH of 4.5. The production medium is sterilized at 121° C. for 30 minutes.

The fermentor is inoculated with 0.5 liters of the prepared inoculum. 25 Hours after the fermentor is inoculated, ethyl caprylate having the structure:

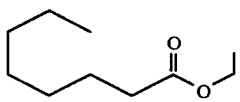

addition is commenced. The pumping of the ethyl caprylate is carried out at a rate of 0.22 grams/hour/liter. The pumping of the ethyl caprylate is carried on for a period of 48 hours.

At the end of the fermentation the pH of the broth is adjusted to between 2 and 3 using 85% phosphoric acid, and then sterilized for 15 minutes at 121° C. The broth is extracted 3 times with ⅓ volume of ethyl acetate. The combined extracts are washed twice with saturated sodium chloroite solution (aqueous) and the solvent is evaporated. The crude is analyzed as methyl esters and is then distilled on a 12″ Goodloe column at a vapor temperature of 92° C. and a vacuum of 1 mm/Hg. The yield is 1.72 grams per liter of gamma octalactone. The percent octalactone recovered is 15.64. The crude weight of the gamma octalactone is 11 grams per liter.

EXAMPLE III

Preparation of Gamma Octalactone Fermentation using *Mortierella Isabellina*, IFO 7873

Reactions:

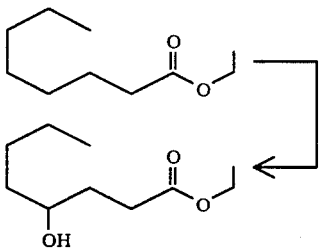

and

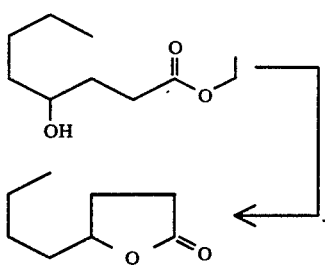

A medium is prepared containing the following the ingredients:
1%: Peptone
0.5%: Yeast extract
0.05%: TWEEN ®80
10.0%: Dextrose A slant of *Mortierella isabellina*, IFO 7873 is placed into 100 ml of the above medium. The inoculum is cultured for a period of 3 days. Two Percent of the thus-obtained culture is placed into 500 ml of the above medium and the inoculum is prepared by growing the culture in the medium at a pH of 4.5 for a period of 24 hours.

A production medium is prepared in a 9 liter fermentor as follows:
1%: Peptone
0.5%: Yeast extract
0.05%: TWEEN ®80
10.0%: Dextrose
and maintained at 27° C. with agitation of 500 rpm, aeration of 0.5 v/v/m and maintained at a pH of 4.5.

The fermentor medium is sterilized at a 121° C. for 30 minutes. The fermentor is then inoculated with 0.5 liters of the above-prepared culture. The fermentor is maintained at 27° C. and operated at 500 rpm for a period of 5 hours after the inoculation.

At the 5 hour time interval, addition of the substrate, the compound having the structure:

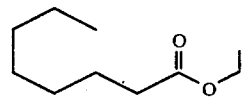

is commenced at the rate of 0.25 g/hr/L.

The ethyl caprylate addition continued for a period of 48 hours.

At the end of the 48 hour period, addition of ethyl caprylate ceases. The pH of the fermentation broth is adjusted to between 2 and 3 using 85% phosphoric acid. The broth is then extracted three times with one-third volume of ethyl acetate each time and the solvent is evaporated.

The crude extract is then fractionally distilled at a vapor temperature of 92° C. and a pressure of 1 mm/Hg. yielding the product having the structure:

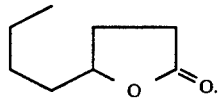

The reaction product contained 34.72% gamma octalactone and the yield was 2.62 grams per liter. The crude weight of the gamma octalactone was 7.56 grams per liter.

EXAMPLE IV

Preparation of Gamma Octalactone using Mortierella Isabellina, IFO 7873

Reactions:

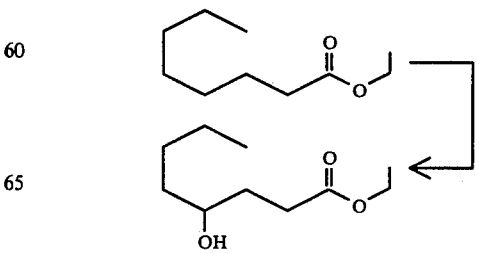

Reactions:

-continued and

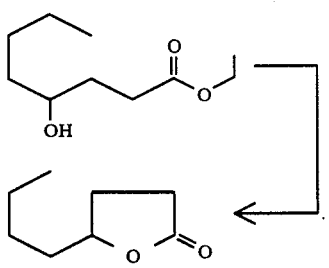

The following medium is prepared:
1.0%: Peptone
0.5%: Yeast extract
0.05%: TWEEN ®80
10.0%: Dextrose.

To 100 ml of the above medium, a slant of *Mortierella isabellina*, IPO 7873 is added. An inoculum is cultured for a period of 3 days. At the end of the 3 day period, the resulting culture is added to 500 ml of the above medium at the rate of 2%. A culture is grown in the 500 ml batch for a period of 24 hours at a pH of 4.5.

The medium:
1.0%: Peptone
0.05%: Yeast extract
0.05%: TWEEN ®80
10.0%: Dextrose
is added to a 9 liter fermentor operating at 27° C., 500 rpm agitation; an aeration rate of 0.5 v/v/m and a pH of 6.5.

The above 500 ml of culture is then inoculated into the medium in the fermentor with stirring and aeration.

Five hours after inoculation, pumping of ethyl caprylate having the structure:

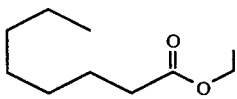

is commenced into the fermentor at the rate of 0.25 g/hr/L. The pumping of the ethyl caprylate is continued over a period of 3 days while maintaining the above conditions in the fermentor.

At the end of the pumping of the ethyl caprylate, the pH of the broth is adjusted to between 2 and 3 using 85% phosphoric acid and the broth is then sterilized for 15 minutes at 121° C. The broth is extracted three times with one-third volume of ethyl acetate. The combined extracts are washed twice with saturated aqueous sodium chloride solution and the solvent is evaporated.

The crude broth is then distilled at a vapor temperature of 92° C. and a pressure of 1 mm/Hg. yielding gamma octalactone having the structure:

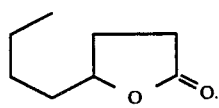

The yield of gamma octalactone is 7.56 grams per liter; the percentage of gamma octalactone is 58.96%; and the crude weight is 12.88 grams per liter.

EXAMPLE V

Preparation of Gamma Octalactone using Mortierella Isabellina, IFO 7873

Reactions:

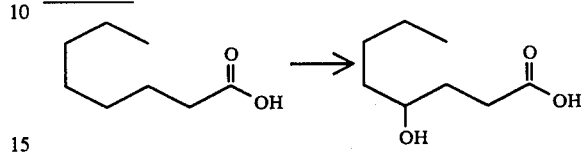

and

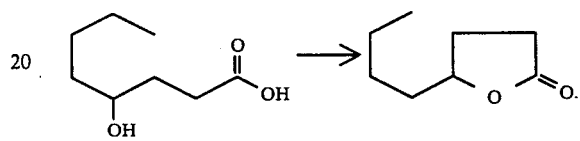

A medium is prepared containing the following ingredients:
1.0%: Peptone
0.05%: Yeast extract
0.05%: TWEEN ®80
10.0%: Dextrose.

Into 100 ml of the above medium, a slant of *Mortierella isabellina*, IFO 7873 is added. The inoculum of the *Mortierella isabellina*, IFO 7873 is cultured for a period of 3 days. At the end of the 3 day period, the culture of the *Mortierella isabellina*, IFO 7873 is added to 500 ml of the medium:
1.0%: Peptone
0.5%: Yeast extract
0.05%: TWEEN ® 80
50.0%: Dextrose.
50 ml. Of the above culture is grown for a period of 24 hours at a pH of 4.5.

Into a 9 liter fermentor operated at 27° C., 500 rpm (agitation), an aeration rate of 0.5 v/v/m and a pH of 6.5 is added the medium:
1.0%: Peptone
0.5%: Yeast extract
0.05%: TWEEN ® 80
10.0%: Dextrose.
500 ml of the *Mortierella isabellina*, IFO 7873 culture prepared above is added to the fermentor medium with stirring and aeration as set forth above.

Five hours after inoculation of the *Mortierella isabellina*, IFO 7873 inoculation, caprylic acid having the structure:

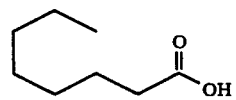

is pumped into the fermentor batch at the rate of 0.27 g/hr/L. The pumping of the caprylic acid is continued for a period of 48 hours.

At the end of the 48 hour period, the pH of the broth is adjusted to between 2 and 3 using 85% phosphoric acid and then sterilized for 15 minutes at 121° C. The broth is extracted three times with one-third volume of ethyl acetate. The combined extracts are washed twice with aqueous saturated sodium chloride solution and the solvent is evaporated. The crude product is then fractionally distilled on a 12" Goodloe column at a vapor temperature of 92° C., a liquid temperature of 104° C. and a pressure of 1 mm/Hg. yielding gamma octalactone having the structure:

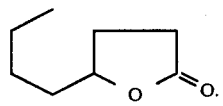

The yield of gamma octalactone is 31.44%; 4.82 grams per liter. The crude weight of the gamma octalactone is 15.32 grams per liter.

EXAMPLE VI

Preparation of Gamma Octalactone using Mortierella Isabellina, IFO 7873

Reactions:

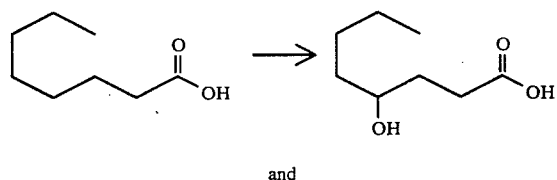

and

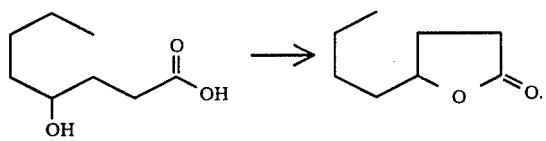

The following medium is prepared:
1.0%: Peptone
0.5%: Yeast extract
0.05%: TWEEN®80
10.0%: Dextrose.

To 100 ml of the above medium, a slant of *Mortierella isabellina*, IFO 7873 is added and an inoculum is grown for a period of 3 days. At the end of the 3 day period, 5% of the medium:
1.0%: Peptone
0.5%: Yeast extract
0.05%: TWEEN®80
10.0%: Dextrose
is inoculated with 2% of the above culture.

The 500 ml culture is grown for a period of 24 hours at a pH of 4.5.

Into a 9 liter fermentor operated at 27° C., an agitation of 500 rpm, an aeration rate of 0.5 v/v/m and a pH of 6.5, the medium:
1.0%: Peptone
0.5%: Yeast extract
0.05%: TWEEN®80
10.0%: Dextrose
is added. With stirring, agitation and aeration, the medium in the fermentor is inoculated with the 500 ml of the above culture containing the *Mortierella isabellina*, IFO 7873 (500 ml).

Twenty four hours after inoculation, pumping of the substrate, the caprylic acid having the structure:

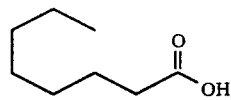

is commenced at the rate of 0.32 g/hr/L (grams per hour per liter). The pumping of the caprylic acid into the fermentor is continued for a period of 72 hours.

At the end of the 72 hour period, the pumping ceases and the pH of the broth is adjusted to between 2 and 3 using 85% phosphoric acid; and then the broth is sterilized for 15 minutes at 121° c. The broth is extracted 3 times with one-third volume of ethyl acetate. The combined extracts are washed twice with saturated sodium chloride solution (aqueous) and the solvent is evaporated.

The crude product is then fractionally distilled on a 12" Goodloe column yielding the following fractions:

| Fraction No. | Vapor Temp. (°C.) | Liquid Temp. (°C.) | Vacuum mm/Hg. Pressure |
|---|---|---|---|
| 1 | 98/ | 101/ | 3.0 |
| 2 | 98 | 105 | 3.0 |
| 3 | 91 | 103 | 1.0 |
| 4 | 92 | 104 | 1.0 |
| 5 | 92 | 104 | 1.0 |
| 6 | 102 | 115 | 1.0. |

The distillation product has a percentage of gamma octalactone of 55./76%; and a yield of 7.81 grams per liter. The crude weight of the gamma octalactone is 14 grams per liter.

The gamma octalactone, containing a mixture of the isomers having the structures:

and

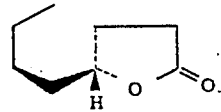

has an optical rotation of minus 28.22 degrees.

EXAMPLE VII

Production of Gamma Octalactone using Mortierella Isabellina, IFO 7873

Reactions:

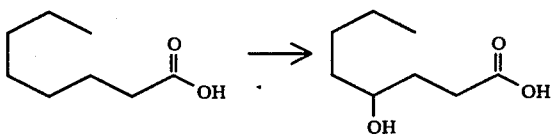

and

Reactions:

[structure: 4-hydroxy carboxylic acid → gamma octalactone]

The following medium is prepared:
1.0%: Enzymatic digest of soy
0.5%: TASTONE ®90
0.05%: TWEEN ®80
10.0%: Dextrose.

The enzymatic digest of soy is obtained from the Deltown Chemurgic Corporation and is identified as SE-50 BT and contains:
5.1%: moisture
10.59%: ash
235%: amino nitrogen
8.83%: total nitrogen
.55.21%: protein
7.10: pH.

The TASTONE ®90 is a brand of bakers yeast extract, spray-dried; a high clarity water soluable bakers yeast extract, spray-dried to a fine yellow tan spray-dried powder having the following analysis:
65-70%: protein
3-6%: moisture
6.4-7.0: pH.
It is manufactured by the Universal Food Corporation, Fermentation Division, Milwaukee, Wis.

100 ml of the above medium is admixed with a slant of *Mortierella isabellina*, IFO 7873 and an inoculum is grown for a period of three days. The resulting iooculum is then added to 500 ml of the above medium at a rate of 2% and the resulting inoculum is grown for a period of 24 hours at a pH of 4.5.

The following medium is added to a 9 liter fermentor operated at 27° C., agitation rate: 500 rpm and a aeration rate: 0.5 v/v/m at a pH of 6.5:
1.0%: enzymatic digest of soy
0.5%: TASTEONE ®90
0.05%: TWEEN ®80
10.0%: Dextrose.
With agitation and aeration, 500 ml of the above inoculum, grown for a period of 24 hours at a pH 4.5, is added to the fermentor. The fermentor is then operated for a period of 5 hours after which time inoculation of caprylic acid having the structure:

[structure: caprylic acid]

is commenced at the rate of 0.32 g/hr/L. The pumping of the caprylic acid is continued for a period of 48 hours.

At the end of the 48 hour period, the pH of the broth is adjusted to between 2 and 3 using 85% phosphoric acid. The broth is then extracted three times with one-third volume ethyl acetate and the solvent evaporated. The crude product is then fractionally distilled at a vapor temperature of 92° C. and a pressure of 1 mm/Hg. yielding a composition of matter containing gamma octalactone having the structure:

[structure: gamma octalactone]

Examples VII(a), VII(b) and VII(c) are repeat runs of the same experiment. The following table shows the example, crude weight, percent gamma octalactone and the distillation product and yield:

| Example | Crude Wt. | % g-Octalactone | Yield |
| --- | --- | --- | --- |
| VII (a) | 12.44 g/L | 59.97 | 07.46 g/L |
| VII (b) | 11.76 g/L | 86.92 | 10.22 g/L |
| VII (c) | 17.04 g/L | 61.14 | 10.42 g/L. |

EXAMPLE VIII

Preparation of Gamma Octalactone using *Mortierella Isabellina*, IFO 7884

Reactions:

[structure: methyl ester of caprylic acid type]

[structure: hydroxy methyl ester]

and

[structure: 4-hydroxy methyl ester → gamma octalactone]

The following medium is prepared:
1.0%: Peptone
0.5%: Yeast extract
0.05%: TWEEN ®80
10%: Dextrose.

A slant of *Mortierella isabellina*, IFO 7884 is added to 100 ml of this medium and the medium is cultured for a period of three days. The resulting culture is added to 500 ml of the above medium at the rate of 2%. The *Mortierella isabellina*, IFO 7884 is then cultured for a period of 24 hours at a pH of 4.5.

The medium:
1.0%: Peptone
0.5%: Yeast extract
0.05%: TWEEN ®80
10%: Dextrose
is placed in a 9 liter fermentor operated at 27° C. with an agitation rate of 500 rpm and an aeration rate of 0.5 v/v/m while being maintained at a pH of 6.5. To this medium is added 500 ml of the above inoculum of *Mortierella isabellina*, IFO 7884.

Five hours after inoculation, pumping of ethyl caprylate having the structure:

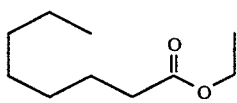

is commenced. The pumping of the ethyl caprylate is carried out at a rate of 0.31 g/hr/L and is continued for a period of 72 hours.

At the end of the 72 hour period, the pumping of the ethyl caprylate ceases.

The pH of the fermentation broth is adjusted to between 2 and 3 using 85% phosphoric acid and the broth is then sterilized for 15 minutes at 121° C. The fermentation broth is extracted three times with one-third volume of ethyl acetate. The combined extracts are washed twice with saturated aqueous sodium chloride solution and the solvent is then evaporated. The crude product is then distilled on a 12" Goodloe column yielding a product rich in gamma octalactone having the structure:

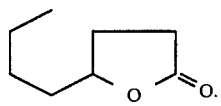

The distillation is carried out at a vapor temperature of 92° C. and a pressure of 1 mm/Hg. The yield of gamma octalactone is 11.7%; the crude weight is 8.08 grams per liter and the yield is 0.95 grams per liter.

EXAMPLE IX

Preparation of Gamma Octalactone using Mortierella Isabellina, IFO 7884

Reactions:

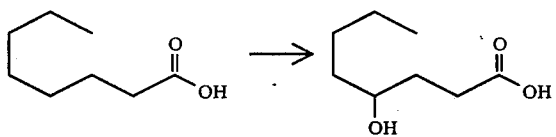

and

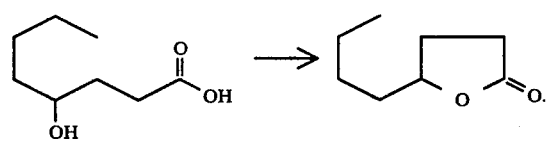

The following medium is prepared:
1.0%: Peptone
0.5%: Yeast extract
0.05%: TWEEN ®80
10%: Dextrose.

A slant of *Mortierella isabellina*, IFO 7884 is placed into 100 ml of the above medium and the resulting mixture is cultured for a period of 3 days. At the end of the 3 day period, the resulting culture is added to 500 ml of the above medium at a rate of 2%. The resulting inoculum is cultured for a period of 24 hours at a pH of 4.5.

The resulting inoculum is then added to a 9 liter fermentor which also contains the medium:
1.0%: Peptone
0.5%: Yeast Extract
0.05%: TWEEN ®80
10%: Dextrose.

The fermentor is operated at a temperature of 27° C., an agitation rate of 500 rpm and an aeration rate of 0.5 v/v/m and is operated at a pH of 6.5.

Five hours after inoculation with the *Mortierella isabellina*, IFO 7884, pumping of caprylic acid having the structure:

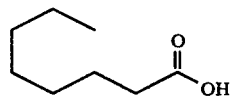

is commenced at the rate of 0.32 g/hr/L. Pumping of the caprylic acid into the fermentor continues at the rate of 0.31 g/hr/L for a period 48 hours.

At the end of the 48 hour period, the pH of the broth is adjusted to between 2 and 3 using 85% phosphoric acid. The broth is then extracted three times with one-third volume ethyl acetate (each time) and the solvent is evaporated. The crude product is then fractionally distilled at a temperature of 92° C. (vapor) and a pressure of 1 mm/Hg. to yield gamma octalactone.

The yield of gamma octalactone is 33.97% and 2.63 grams per liter. The crude weight is 7.75 grams per liter.

EXAMPLE X

In a churn or premixer 900 kilograms of fat mixture were mixed with the aqueous phase described below. The fat mixture consisted of 25% rape seed oil, 45% coconut oil, 20% hardened whale oil having a melting point of 40°–42° C. and 10% hardened rape seed oil having a melting point of 40°–42° C. In the fat mixture was dissolved 4 kilograms of monoglyceride and 3 kilograms of lecithin. The temperature of the fat mixture when introduced into the churn was about 45° C.

The aqueous phase had a temperature of about 15° C. and consisted of 115 kilograms of pasteurized and cultured milk, 55 kilograms of water, 17 kilograms of salt (2.8 kilograms of potato meal), 1.1 kilograms of sodium benzoate, 0.150 kilograms of sodium bicarbonate. 1.0 grams of diacetyl, and 0.350 kilograms of the gamma octalactone composition of bulked distillation Fractions 2-5 of Example VI, supra, containing gamma octalactone.

After completion of the mixing there was added 0.750 kilograms of vitamin oil containing 40,000 I.U. of vitamin A and 2,300 I.U. of vitamin $D_2$ per gram, and 0.560 kilograms of carotin oil containing 7,000 I.U. of carotin per gram. After mixing there was added an aroma preparation consisting of 2.5 grams of decalactone and 10 grams of stearolactone dissolved in 200 grams of oil. The mixing was continued for a few minutes and the batch was then pumped to a chilled roll. The chilled emulsion was then supplied to a complector and then put up in packets.

The result was a product having excellent taste and flavor similar to that of butter. The flavor developed only after a few days.

EXAMPLE XI

The procedure described in Example X was repeated except that as aromatizing substances were used 0.9 grams of nonyllactone, 3.0 grams of gamma octalactone, bulked distillation Fractions 2-5 of Example VI, supra, 1.2 grams of undecalactone, and 12 grams of stearolactone, per ton of the finished product.

EXAMPLE XII

The procedure described in Example X was repeated except that as aromatizing substances were used 1.5 grams of decalactone, 3.5 grams of the gamma lactone composition of Example IX (distilled), 1.0 grams of dodecalactone, and 10 grams of stearolactone, per ton of finished product.

EXAMPLE XIII

The procedure described in Example X was repeated except that as aromatizing substances were used 0.25 grams of nonyllactone, 3.5 grams of the composition of Example VII(b) containing gamma nonyllactone, 1.6 grams of decalactone, 0.50 grams of undecalactone, and 10 grams of stearolactone per ton of the finished product.

EXAMPLE XIV

The procedure described in Example X was repeated except that as aromatizing substances were used 12 grams of stearolactone, and 8 grams of the gamma octalactone containing composition of Example IV, supra, per ton of finished product. The taste was excellent and the frying flavor agreeable. As in the preceding examples it was found that pastry made with this margarine had an agreeable butter flavor and retained this flavor also after storing.

EXAMPLE XV

Artificial cream was made in the following way.

One kilogram of margarine, to which had been added emulsifying agents for cream whipping, was molten and had added thereto 0–0.25 milligrams of nonyllactone, 2.5 milligrams of decalactone, 3.5 grams of the gamma octalactone-containing composition of Example III, supra, 0.5 milligrams of undecalactone and 10 milligrams of stearolactone. Two liters of milk were then added and mixed with the margarine and the mixture was then passed through a homogenizer. The artificial cream thus obtained had good taste and was free from the extraneous taste characteristic of the ordinary artificial cream.

EXAMPLE XVI

Patchouli Perfume Formulation

The following mixture is prepared:

| Ingredients | Parts by Weight |
|---|---|
| Orange oil | 50 |
| Bergamot oil | 20 |
| Lime oil | 100 |
| Neroli oil | 5 |
| LYRAL ® (registered trademark of International Flavors & Fragrances Inc.) | 100 |
| GALAXOLIDE ® (registered trademark of International Flavors & Fragrances Inc.) | |
| Gamma methyl ionone | 20 |
| 1-Acetyl-2,5,5-trimethyl-cycloheptane | 150 |
| Gamma octalactone prepared according to Example VI (bulked distillation Fractions 2-5) | 150 |

Bulked distillation Fractions 2-5 imparts to this patchouli formulation a sophisticated coconut topnote and tonka bean-like undertone. Accordingly, the perfume composition of Example XVI can be described as "patchouli, with coconut-like topnote and tonka bean-like undertone".

EXAMPLE XVII

Preparation of Soap Compositions

One hundred grams of soap chips are produced according to Example V of U.S. Pat. No. 4,058,487 issued on Nov. 5, 1977, the specification for which is incorporated herein by reference, as follows:

The sodium salt of an equal mixture of $C_{10}$–$C_{14}$ alkane sulfonate (95% active), 40 pounds, is dissolved in a mixture of 80 pounds of anhydrous isopropanol and 125 pounds of deionized water at 150° F. In this mixture is dissolved 10 pounds of partially hydrogenated coconut oil fatty acids and 15 pounds of sodium mono-$C_{14}$ alkyl maleate, and the pH of this solution is adjusted to 6.0 by the addition of a small amount of 50% aqueous solution of sodium hydroxide. The isopropanol is distilled off and the remaining aqueous solution is drum dried. The resulting solid actives are then blended in a chip mixture with 10 pounds of water, 0.2 pounds of titanium hydroxide and 0.7 pounds of one of the perfume ingredients set forth in Table I below. The chips are then plodded into logs, cut to size and finally stamped into bars having a pH of approximately 6.9.

Each of the perfumed soaps produced by means of the foregoing procedure manifests an excellent aroma as set forth in Table I, infra.

TABLE I

| Ingredient | Fragrance Profile |
|---|---|
| Mixture of compounds produced according to Example VI, bulked distillation Fractions 2-5. | A coconut aroma with Tonka bean-life undertones. |
| Perfume composition of Example XVI. | Patchouli, with coconut-like topnote and Tonka bean-like undertone. |

EXAMPLE XVIII

Preparation of Detergent Composition

A total of 100 grams of a detergent powder prepared according to U.S. Pat. No. 4,058,472 (the specification for which is incorporated by reference herein) and containing 5% by weight of the soldium salts of a mixture of sulfonated $C_{14}$–$C_{18}$ alkyl catechol as a surface active component, the mixture being 60 parts by weight of mono-$C_{14}$–$C_{18}$ alkyl catechol and 40 parts by weight of di-$C_{14}$–$C_{18}$ catecho, 35% sodium tetrapyrophosphate, 30% sodium silicate, 20% of sodium carbonate, 3% of sodium carboxymethyl cellulose and 7% of starch is mixed with 0.15 grams individually with each of the aroma ingredients set forth in Table I of Example XVII until a substantially homogeneous composition is obtained. Each of the compositions has an excellent aroma as set forth in Table I of Example XVII.

EXAMPLE XIX

Preparation of a Cosmetic Powder Composition

A cosmetic powder is prepared by mixing in a ball mill, 100 grams of talcum powder with 0.25 grams of each of the perfume materials of Table I of Example XVII. Each of the powders has an excellent aroma as set forth in Table I of Example XVII.

EXAMPLE XX

Perfumed Liquid Detergent

Concentrated liquid detergents with aromas as set forth in Table I of Example XVII are prepared by adding 0.10%, 0.15% and 0.20% of each of the ingredients set forth in Table I of Example XVII. They are prepared by adding and homogeneously mixing the appropriate quantity of perfume substance of Table I of Example XVII in the liquid detergent. The detergents individually possess aromas as set forth in Table I of Example XVII, the intensity increasing with greater concentrations of perfume substance set forth in Table I of Example XVII.

EXAMPLE XXI

Preparation of a Cologne and Handkerchief Perfume

Each of the ingredients of Table I of Example XVII is incorporated individually into colognes of several strengths at concentrations of 2.0%, 2.5%, 3.0%, 3.5%, 4.0% and 5.0% in 75%, 80%, 85%, 90% and 95% aqueous ethanol; and into several concentrations of handkerchief perfumes at the rate of 15%, 20% and 25% (in 80%%, 85%, 90% and 95% aqueous ethanol). Distinct and definite aromas as set forth in Table I of Example XVII are imparted to the colognes and to the handkerchief perfumes at the several concentrations set forth above.

EXAMPLE XXII

Preparation of Soap Compositions

One hundred grams of soap chips (IVORY ® produced by the Proctor & Gamble Company of Cincinnati, Ohio) are admixed with one gram of each of the substances set forth in Table I of Example XVII, supra, until homogeneous compositions are obtained. In each of the cases, the homogeneous compositions are heated under 3 atmospheres pressure at 180° C. for a period of three hours and the resulting liquids are placed into soap molds. The resulting soap cakes, on cooling, manifest excellent aromas as set forth in Table I of Example XVII.

EXAMPLE XXIII

Preparation of Solid Detergent Compositions

Detergents are prepared from the following ingredients according to Example I of Canadian Patent No. 1,007,948, the specification for which is incorporated by reference herein:

| Ingredients | Parts by Weight |
| --- | --- |
| NEODOL ® 45-11 | 12 |
| (a $C_{14}$-$C_{15}$ alcohol ethoxylated with 11 moles of ethylene oxide) | |
| Sodium carbonate | 55 |
| Sodium citrate | 20 |
| Sodium sulfate, water brighteners | q.s. |

This detergent is "phosphate-free" detergent. A total of 100 grams of said detergent is admixed with 0.10, 0.15, 0.20 and 0.25 grams of each of the substances set forth in Table I of Example XVII, supra. Each of the detergent samples has an excellent aroma as indicated in Table I of Example XVII.

EXAMPLE XXIV

Preparation of Drier-Added Fabric Softener Article

Utilizing the procedure of Example I at column 15 of U.S. Pat. No. 3,632,396 the specification for which is incorporated by reference herein, a non-woven cloth substrate useful as a drier-added fabric softening article of manufacture is prepared wherein the substrate, substrate coating and outer coating and the perfume material are as follows:

1. a water "dissolvable" paper ("Dissolvo Paper") as the substrate;
2. ADOGEN ®448 (melting point about 140° F.) as the first substrate coating; and
3. an outer coating having the following formulation (melting point about 150° F.);
   57% $C_{20}$-$C_{22}$ HAPS;
   22% isopropyl alcohol;
   20% antistatic agent; and
   1% of one of the perfumery substances set forth in Table I of Example XVII, supra.

Fabric softening compositions containing the substances as set forth in Table I of Example XVII, supra, essentially consist of a substrate having a weight of about 3 grams per 100 square inches; a substrate coating weighing about 1.85 grams per 100 square inches of substrate; and an outer coating weighing about 1.5 grams per 100 square inches of substrate are prepared thereby providing a total aromatized substrate and outer coating weight ratio of about 1:1 by weight of the substrate.

The aromas as set forth in Table I of Example XVII, supra, are imparted in a pleasant manner to the head space in a drier on operation thereof using the said drier-added fabric softening non-woven fabric by adding to the drying cycle.

As stated above in the case of fabric softener articles, the entire U.S. Pat. No. 3,632,396 is incorporated by reference herein. Thus, all of the articles of U.S. Pat. No. 3,632,396 acting as fabric softening articles in said U.S. Patent may be perfumed in their outer coating with from 0.25% up to 5% by weight of each of the perfuming substances of Table I of Example XVII, supra.

EXAMPLE XXV

Hair Preparation

A "soft-feel, good-hold" hair spray is produced containing the following ingredients:

| Ingredients | Parts by Weight |
| --- | --- |
| Polyvinylpyrollidone/vinyl | 4.00 |

| Ingredients | Parts by Weight |
| --- | --- |
| acetate "E-735 Copolymer" manufactured by the GAF Corporation of New York, N.Y. | |
| Anhydrous ethanol | 70.90 |
| Dioctyl sebecate | 0.05 |
| Benzyl alcohol | 0.05 |
| "Propellant A-46" manufactured by the GAF Corporation of New York, N.Y. | 24.95 |
| Fragrance ingredient as set forth in Table I of Example XVII, supra. | 0.05 |

The PVP/VA copolymers are first dissolved in alcohol and all other ingredients are added until uniform. The propellant is then pressurized and used as an aerosol. The resulting hair sprays each have pleasant aromas as et forth in Table I of Example XVII, supra.

EXAMPLE XXVI

Scouring Cleanser Composition

A scouring cleanser composition is prepared in accordance with Example I at columns 11 and 12 of U.S. Pat. No. 4,193,888 issued on Mar. 18, 1980, the specification for which is incorporated by reference herein. To this composition, the substances set forth in Table I of Example XVII, supra, are added at the level of 0.25% as set forth in the table in said Example I of U.S. Pat. No. 4,193,888 yielding an aroma on using said cleanser in ordinary circumstances which is quite pleasant and described in Table I of Example XVII, supra.

EXAMPLE XXVII

A fabric softening article prepared substantially as set forth in Example VIII of Canadian Patent No. 1,069,260, the specification for which is incorporated by reference herein, is prepared containing 0.21% by weight of a perfuming substance as set forth in Table I of Example XVII, supra, and yielding on use in a drier, a faint aroma as set forth in Table I of Example XVII, supra.

EXAMPLE XXVIII

Tobacco Flavor Formulations

Cigarettes are produced using the following tobacco formulations:

| Ingredients | Parts by Weight |
| --- | --- |
| Bright | 40.1 |
| Burley | 24.9 |
| Maryland | 1.1 |
| Turkish | 11.6 |
| Stem (flue cured) | 14.2 |
| Glycerine | 2.8 |
| H$_2$O | 5.3. |

At the rate of 0.2%, the following tobacco formulation is applied to all of the cigarettes produced with the above tobacco formulation:

| Ingredients | Parts by Weight |
| --- | --- |
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol (95%) | 20.00 |
| H$_2$O | 41.900. |

To portions of 50% of the cigarettes at levels of 10 and 20 ppm, the octalactone-containing composition of Example V (distilled) is added. These cigarettes are hereinafter called "experimental" cigarettes. The cigarettes without the octalactone composition are hereinafter called "control" cigarettes. The control and experimental cigarettes are then evaluated by paired comparison and the results are as follows:

(a) In aroma, the experimental cigarettes are all found to be more aromatic with Turkish tobacco-like nuances;

(b) In smoke flavor, the experimental cigarettes are all found to be more aromatic, more sweet with Turkish tobacco, oriental-like nuances than the control cigarettes.

The experimental cigarettes containing the mixture of lactones are found to be fruity and have pleasant aesthetically pleasing fruity notes in addition.

EXAMPLE XXIX

Pudding

At the rate of 0.8 ppm, the composition containing gamma octalactone of Example VI, bulked distillation Fractions 2-5 is added to a ROYAL ® butterscotch pudding composition. Pleasant aesthetically pleasing coconut nuances were added to the butterscotch pudding as a result of the use of the octalactone composition. Without the octalactone composition no such coconut nuances are added. A panel of 10 individuals prefers the octalactone-containing butterscotch pudding.

What is claimed is:

1. A process for preparing a composition containing a significant amount of optically active gamma octalactones having the structure:

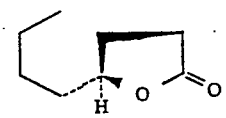

and

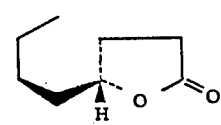

and in addition a mixture of compounds having the structures:

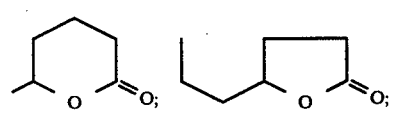

-continued

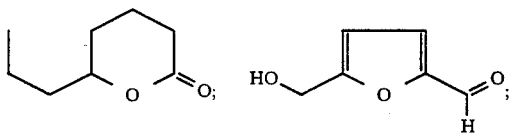

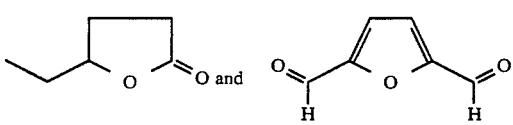

comprising the sequential steps of:
(i) carrying out a fermentation of a compound having the structure:

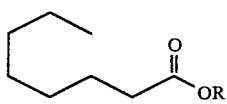

in the presence of an organism selected from the group consisting of:
*Mortierella isabellina*, ATCC 44583;
*Mortierella isabellina*, ATCC 38063;
*Syncephalastrum racemosum*, NRRL A-5889
*Mortierella isabellina*, IFO 7884;
*Mortierella ramanniana* var.angulispora, IFO 8187;
*Mortierella isabellina*, CBS 221.29; and
*Mortierella isabellina*, IFO 7873; in aqueous media, for a period of time of from 40-200 hours under aerobic conditions, maintaining the dissolved oxygen content from 20% and 100% by weight, whereby compounds defined according to the structure:

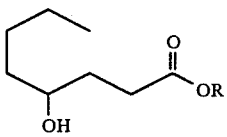

are produced wherein R represents hydrogen or ethyl, according to the reaction:

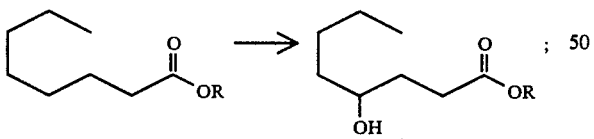

(ii) effecting lactonization of the resulting gamma hydroxy octanoic acid derivative by heating the said acid derivative according to the reaction;

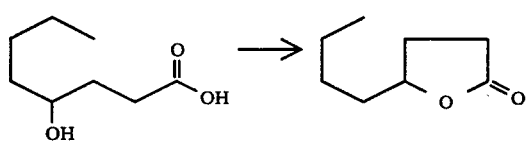

and
(iii) distilling the resulting mixture at a vapor temperature of 91°-98° C. and a pressure of 1-3 mm Hg to yield a mixture of compounds having the structures:

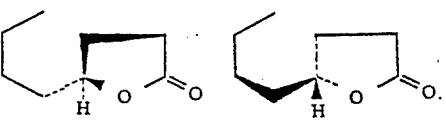

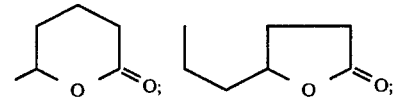

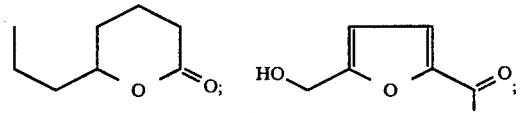

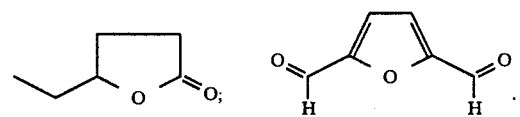

2. The process of claim 1 wherein R is hydrogen.
3. The process of claim 1 wherein R is ethyl.
4. The process of claim 1 wherein the hydroxy octanoic acid produced has a structure selected from the group consisting of:

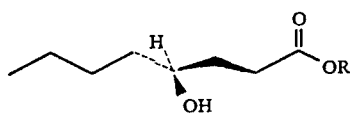

and

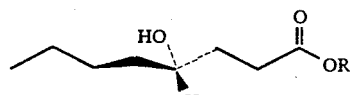

5. The process of claim 1 wherein the resulting hydroxy octanoic acid has a structure selected from the group consisting of:

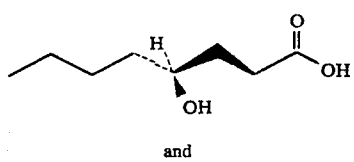

and

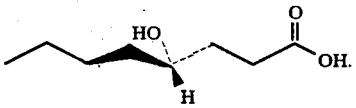

6. The product produced according to the process of claim 1.
7. The product produced according to the process of claim 2.
8. The product produced according to the process of claim 3.
9. The product produced according to the process of claim 4.

10. The product produced according to the process of claim 5.

11. The process of claim 1 wherein process step (i) is carried out at 25°-27° C. for a period of time of from 48-74 hours at a pH of from 4.5-6.5 and process step (ii) is carried out at a temperature of 121° C. for a period of time of 15 minutes at a pH of from 2-3.

* * * * *